(12) United States Patent
Radka et al.

(10) Patent No.: US 7,521,184 B2
(45) Date of Patent: Apr. 21, 2009

(54) DETECTION AND QUANTITATION OF NUCLEIC ACID MOLECULES IN BIOLOGICAL SAMPLES

(75) Inventors: Susan Radka, Arvada, CO (US); Zinnen Shawn, Denver, CO (US); Vasant Jadhav, Boulder, CO (US); James McSwiggen, Boulder, CO (US); Narendra Vaish, Denver, CO (US)

(73) Assignee: Sirna Therapeutics, Inc., San Francisco, CA (US)

( * ) Notice: Subject to any disclaimer, the term of this patent is extended or adjusted under 35 U.S.C. 154(b) by 7 days.

(21) Appl. No.: 10/568,134

(22) PCT Filed: Aug. 17, 2004 (Under 37 CFR 1.47)

(86) PCT No.: PCT/US2004/026857
§ 371 (c)(1), (2), (4) Date: Apr. 12, 2007

(87) PCT Pub. No.: WO2005/021800
PCT Pub. Date: Mar. 10, 2005

(65) Prior Publication Data
US 2008/0050721 A1    Feb. 28, 2008

Related U.S. Application Data

(60) Provisional application No. 60/543,784, filed on Feb. 11, 2004, provisional application No. 60/497,222, filed on Aug. 22, 2003.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3

(58) Field of Classification Search .............. 435/6; 536/23.1, 24.3
See application file for complete search history.

(56) References Cited

U.S. PATENT DOCUMENTS

| | | | | |
|---|---|---|---|---|
| 4,787,963 A | * | 11/1988 | MacConnell | 204/450 |
| 5,116,734 A | * | 5/1992 | Higgs et al. | 435/28 |
| 5,354,657 A | * | 10/1994 | Holtke et al. | 435/6 |
| 5,474,895 A | * | 12/1995 | Ishii et al. | 435/6 |
| 5,766,889 A | * | 6/1998 | Atwood | 435/91.2 |
| 6,541,205 B1 | * | 4/2003 | Yokoyama et al. | 435/6 |
| 2007/0224610 A1 | * | 9/2007 | Kato | 435/6 |

OTHER PUBLICATIONS

Ishii et al., Bead-based sandwich hybridization characteristics of oligonucleotide-alkaline phosphatase conjugates and tyheir potential of quantitating target RNA sequences. Bioconjugate Chemistry 4 : 34-41 (1993).*
Balaguer et al., Quantification of DNA sequences obtained by polymerase chain reaction using a bioluminescent adsorbent. Analytical Biochemistry 195 (1) : 105-110 (1991).*
Teare et al., Measurement of nucleic acid concentrations using the DyNA Quant and the GeneQuant. BioTechniques 22 (6) : 1170-1174 (1997).*

* cited by examiner

*Primary Examiner*—Ethan Whisenant

(57) ABSTRACT

The present invention concerns processes for the detection and quantitation of nucleic acid molecules, polynucleotides, and/or oligonucleotides in a sample using hybridizationdetection assays, antibody-mediated recognition assays, nucleic acid sensor molecules, chromatographic assays, and/or electrophoresis assays. The present invention specifically concerns processes for the detection and quantitation of double stranded nucleic acid molecules, polynucleotides, and/or oligonucleotides in a sample using hybridization-detection assays. The nucleic acid molecules, polynucleotides, and/or oligonucleotides can include molecules that mediate RNA interference, such as short interfering nucleic acid (siNA), short interfering RNA (siRNA), double-stranded RNA (dsRNA), micro-RNA (miRNA), and short hairpin RNA (shRNA) molecules. The nucleic acid molecules, polynucleotides, and/or oligonucleotides can include nucleic acid aptamers, enzymatic nucleic acid molecules, decoys, antisense, 2',5'-oligoadenylate molecules, triplex forming oligonucleotides or any other nucleic acid molecule of interest. The present invention also concerns kits that allow for the detection and quantitation of nucleic acid molecules, polynucleotides, and/or oligonucleotides in a sample.

20 Claims, 27 Drawing Sheets

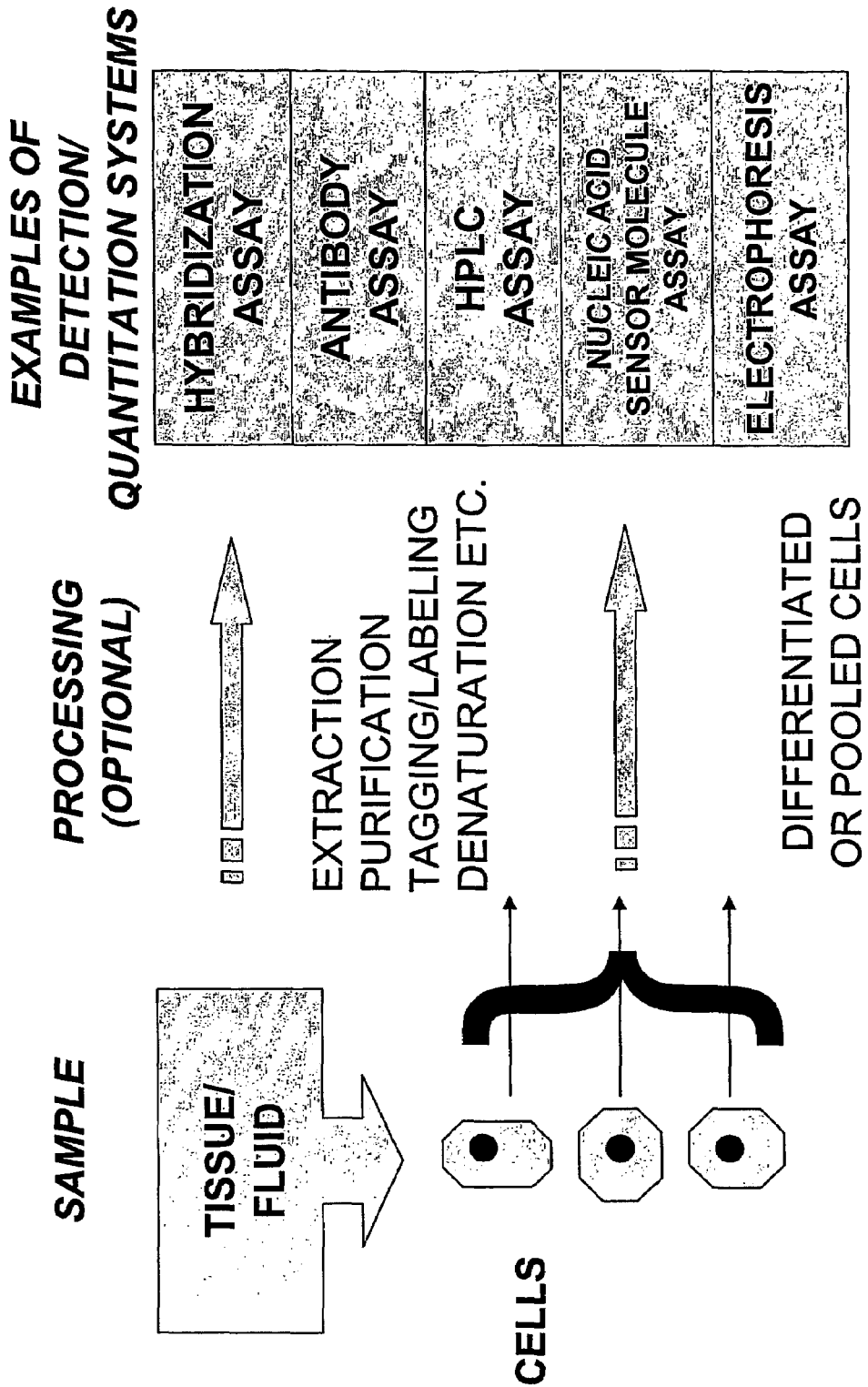
Figure 1A: Detection and Quantitation of siNA in a Sample

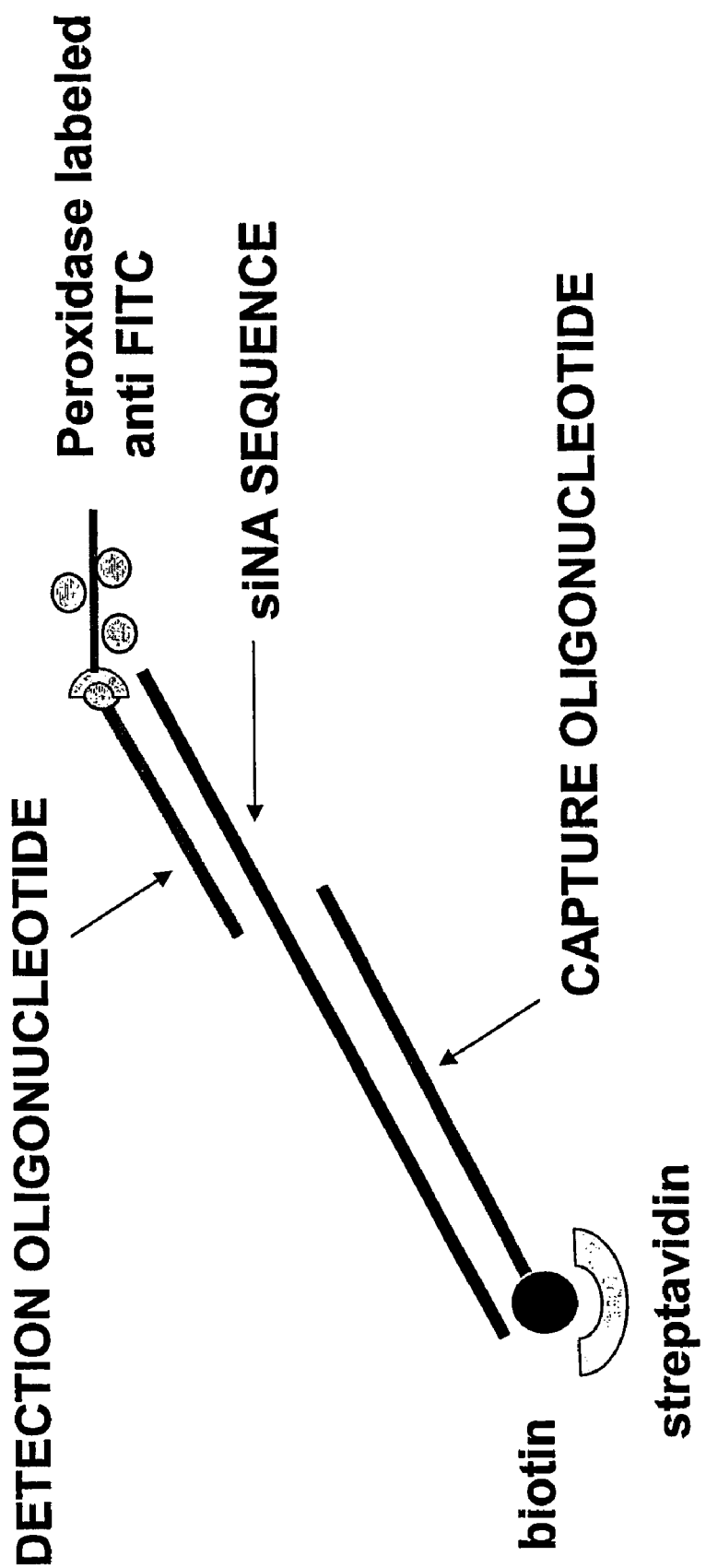
Figure 1B: siNA Hybridization Assay

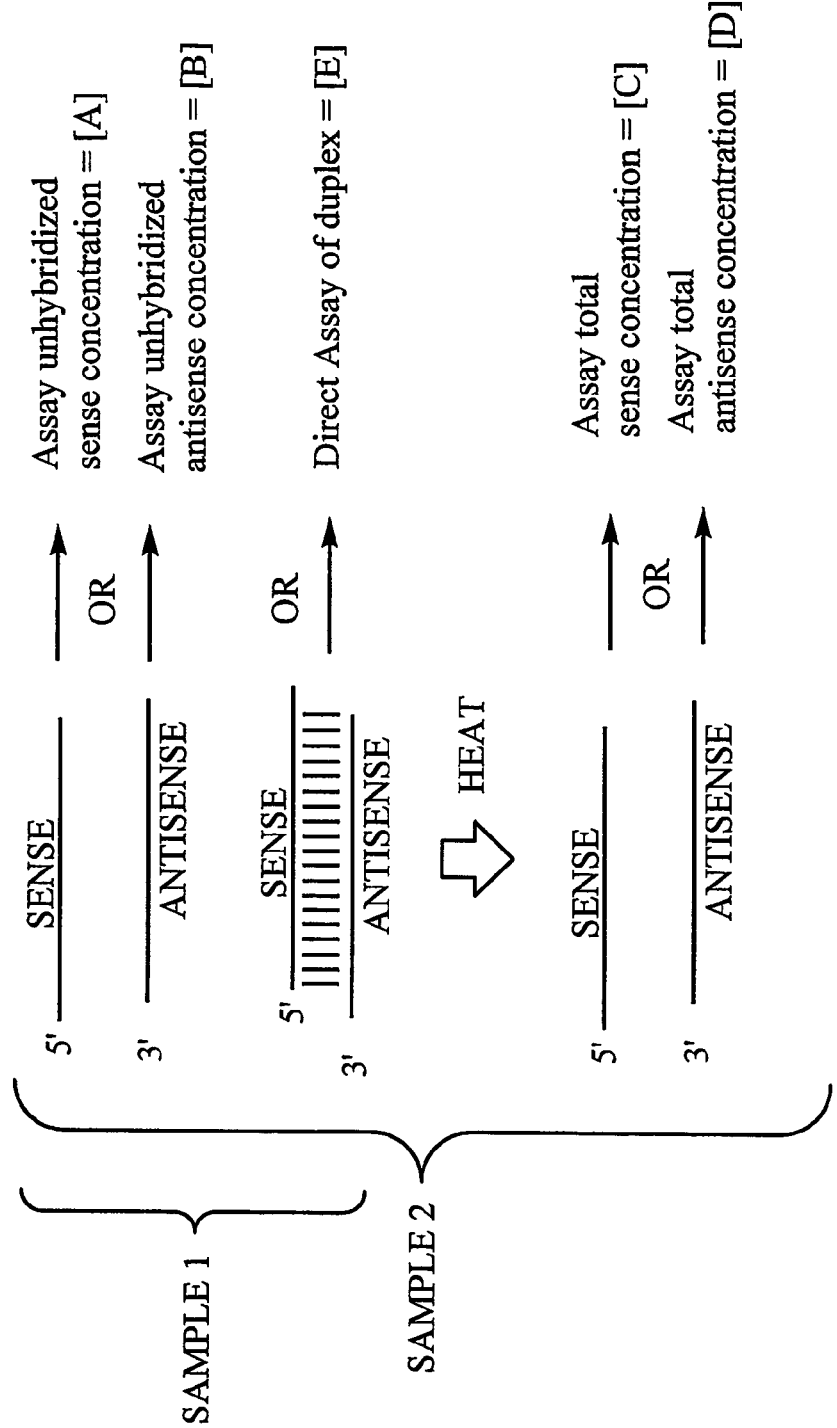
Figure 1C: Principle of siNA detection/quantitation Assays

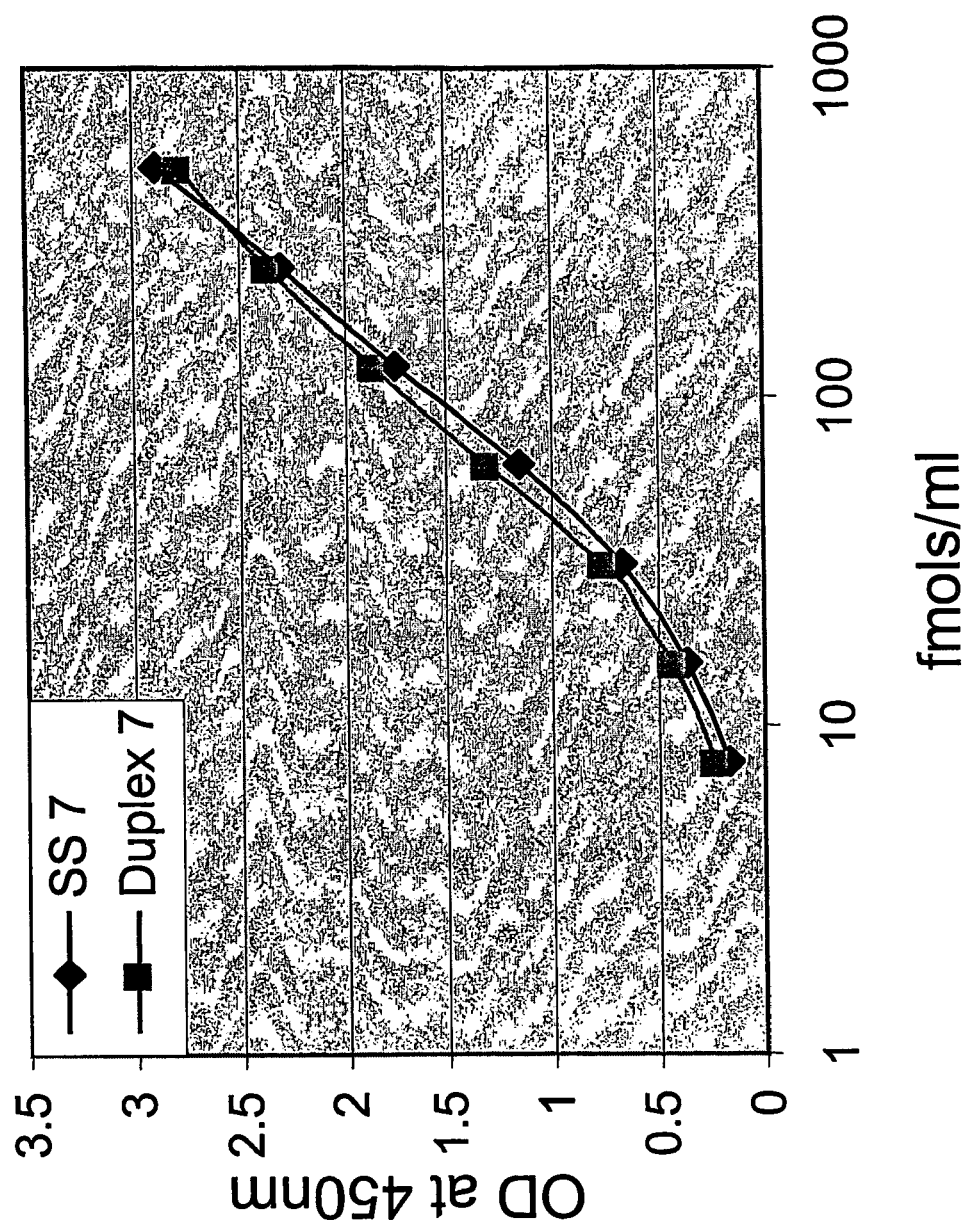
Figure 2A: siNA Stab 7 Sense Strand Standard Curve

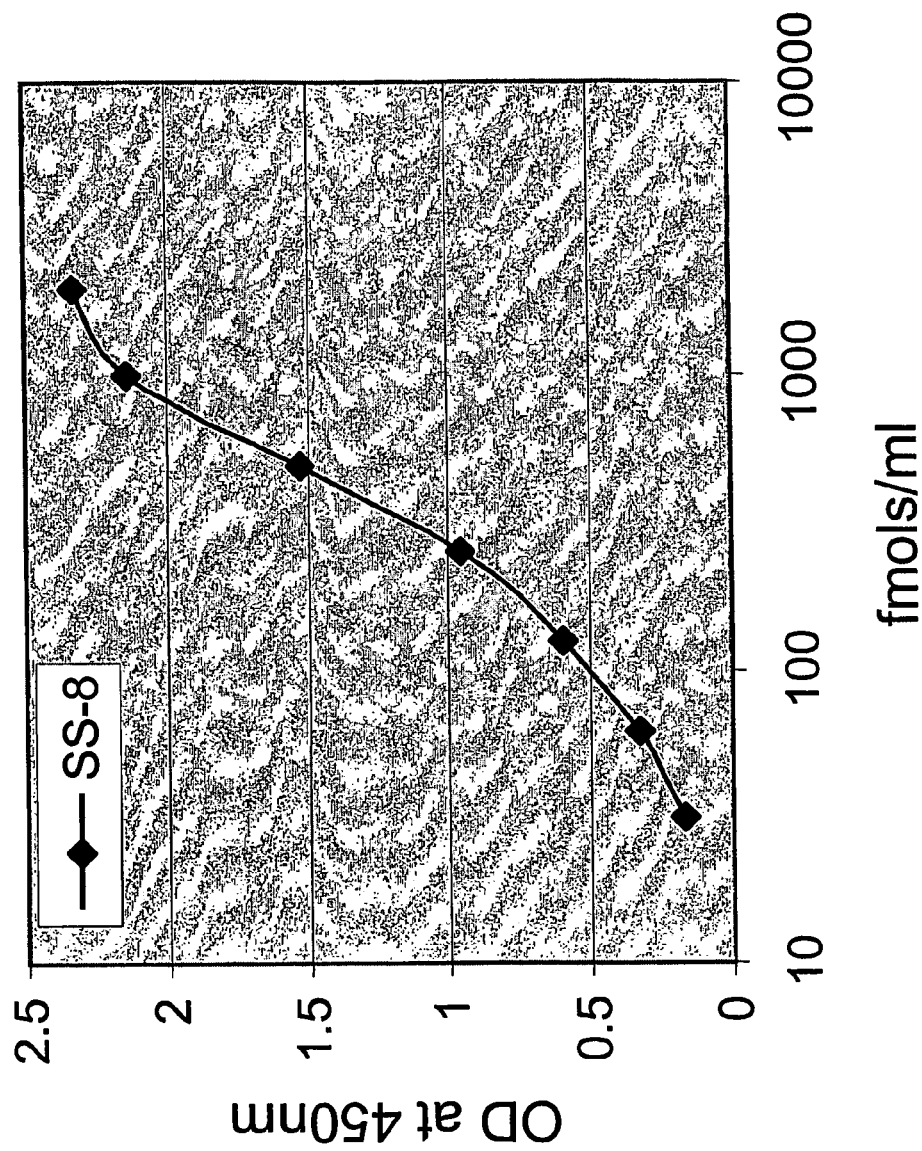
Figure 2B: siNA Stab 8 Antisense Strand Standard Curve

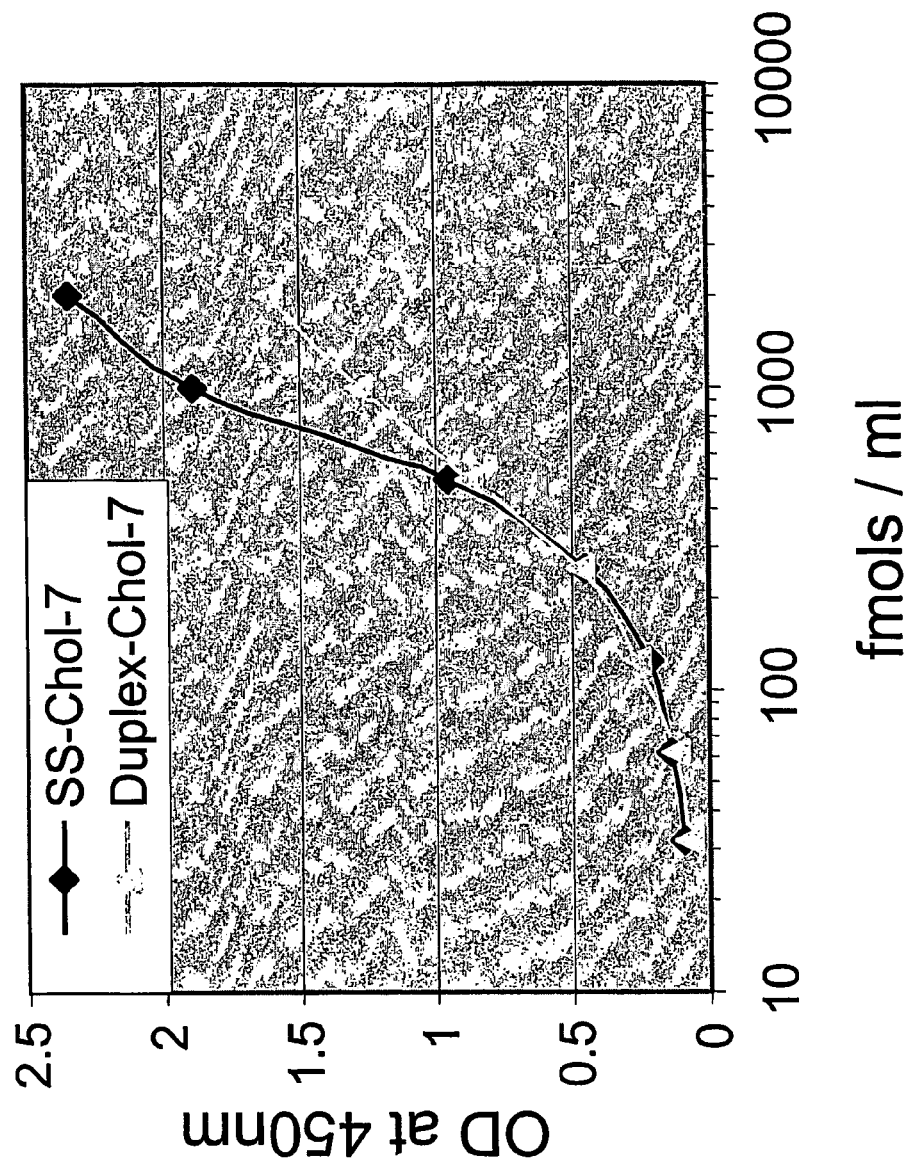
Figure 2C: siNA Stab 7 Cholesterol Conjugate Sense Strand Standard Curve

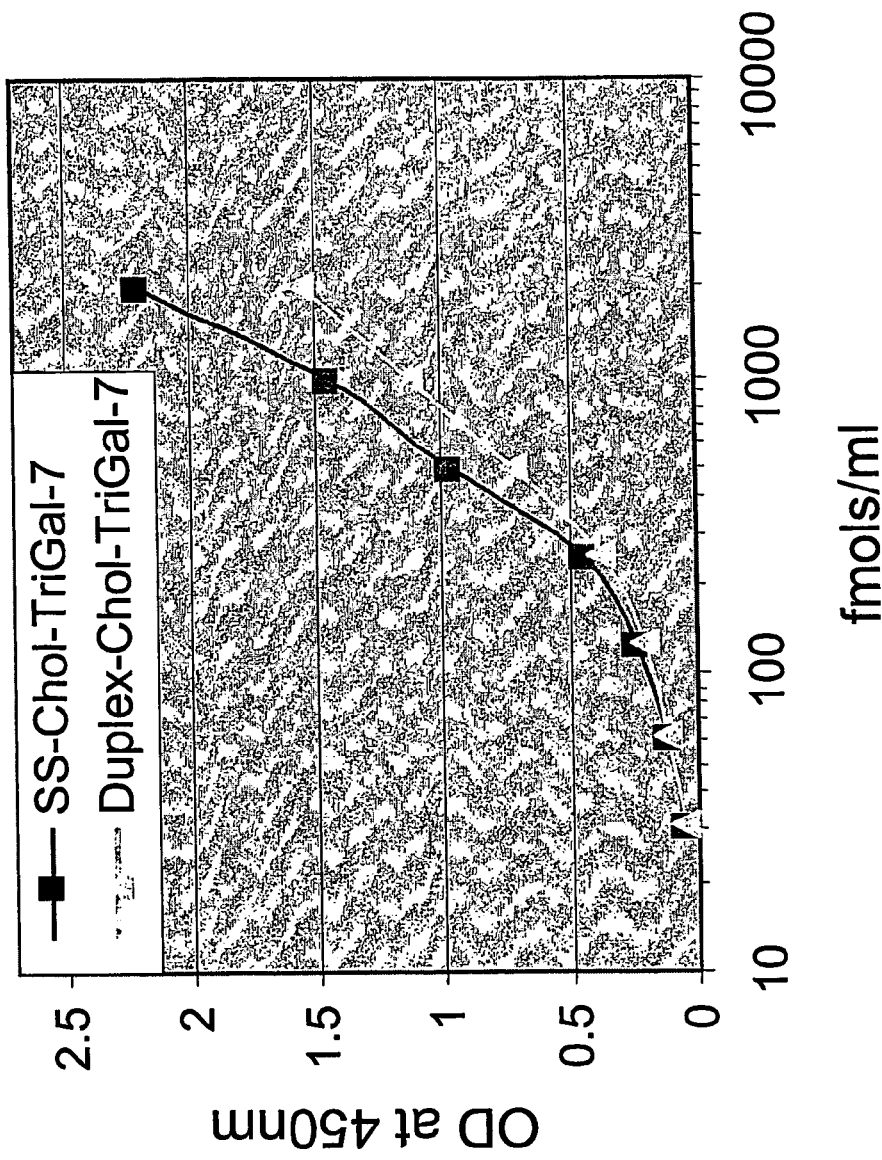
Figure 2D: siNA Stab 7 Trigalactose Cholesterol Conjugate Antisense Strand Standard Curve

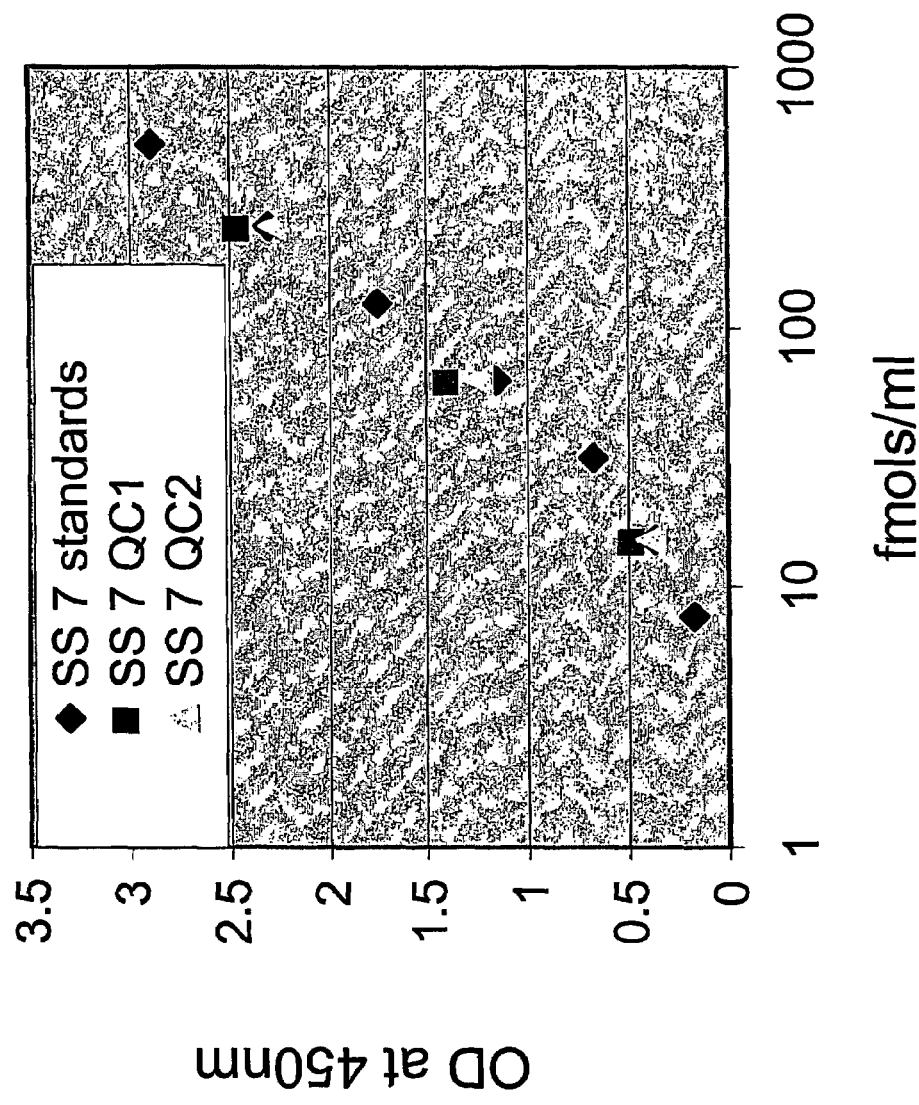
Figure 3A: siNA Stab 7 Single Stranded Quality Control Sample

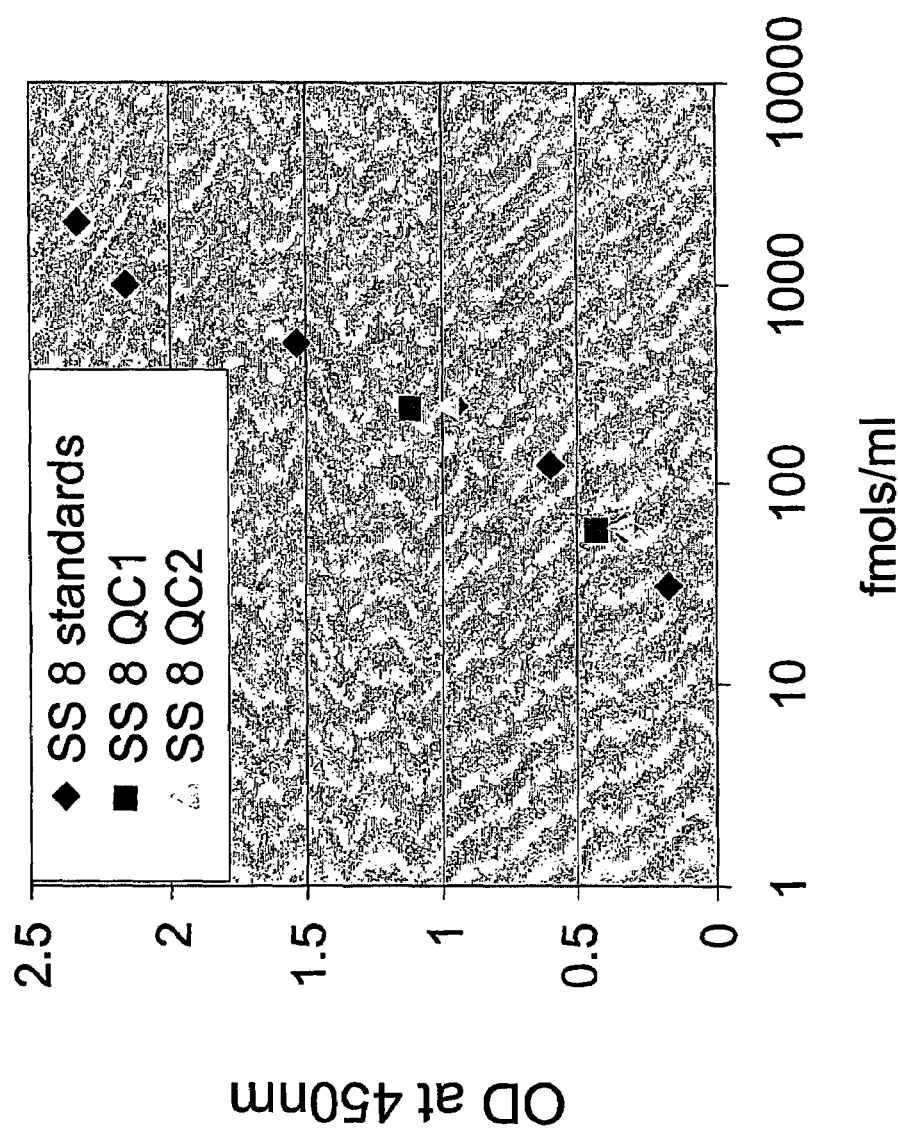
Figure 3B: siNA Stab 8 Single Stranded Quality Control Sample

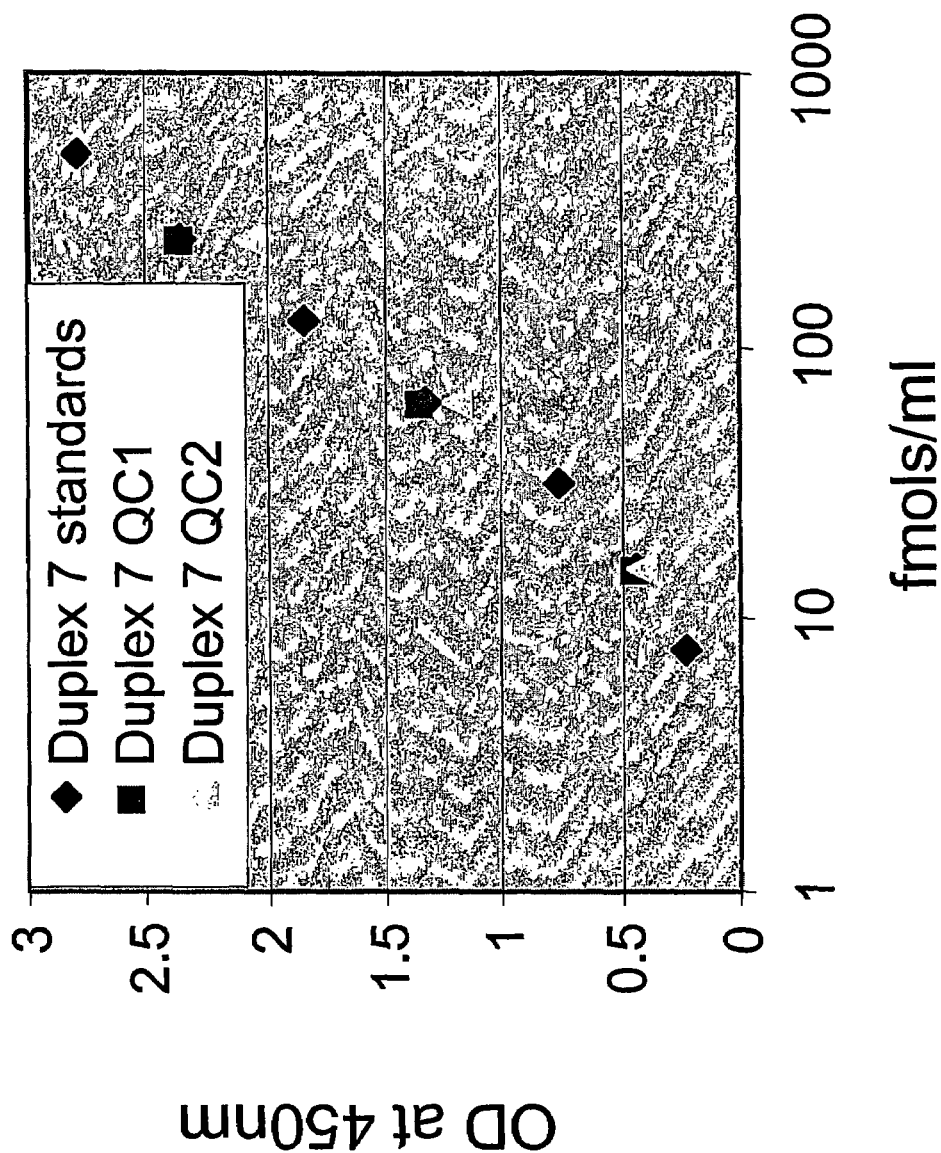
Figure 3C: siNA Stab 7 Duplex Quality Control Sample

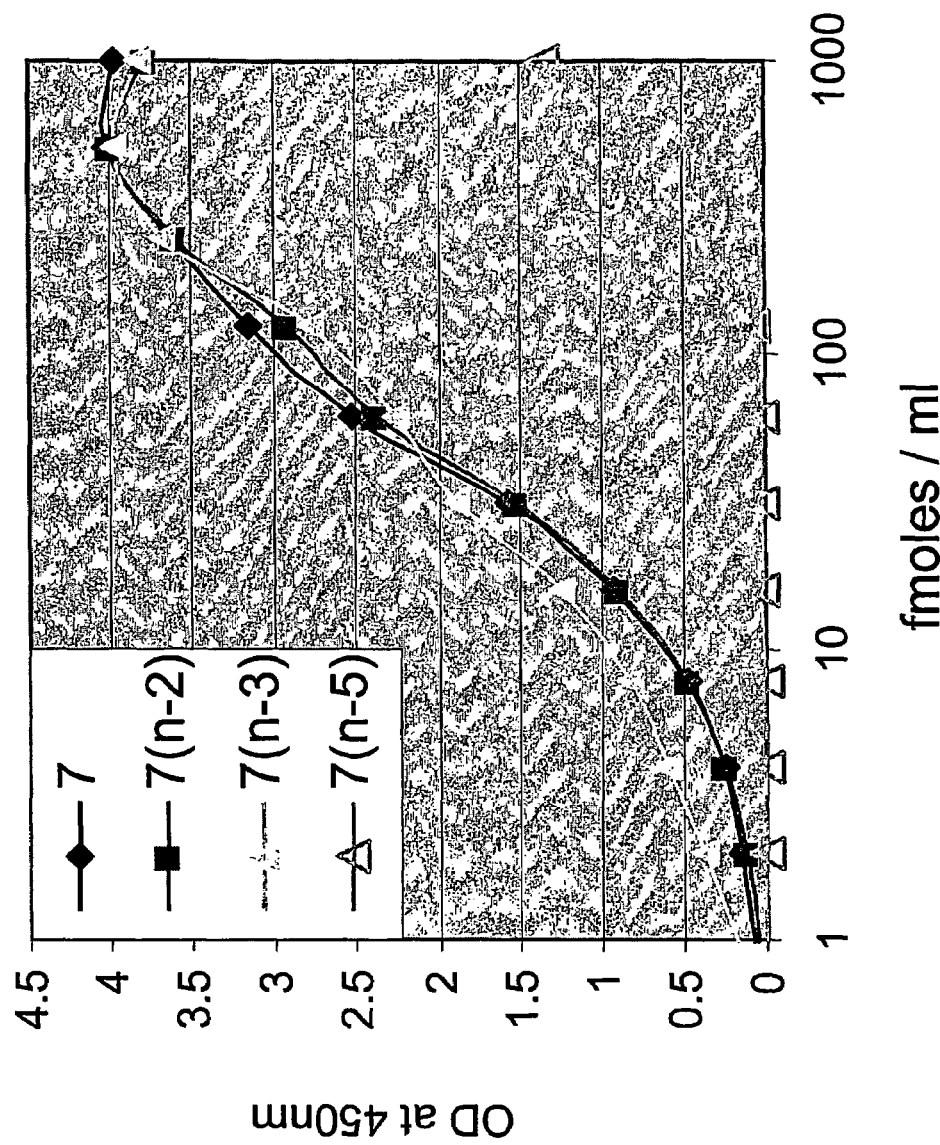
*Figure 4A: Detection of potential siNA Stab 7 Metabolites via Hybridization Assay*

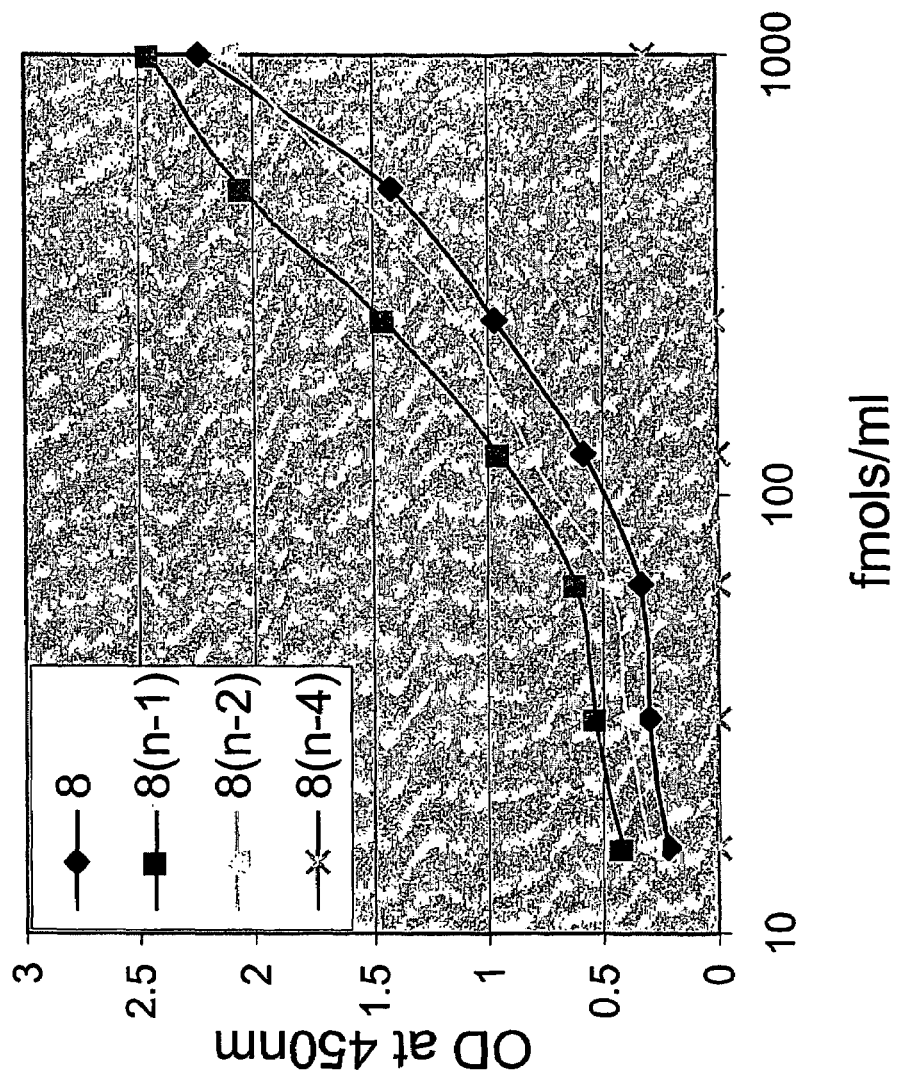
Figure 4B: Detection of potential siNA Stab 8 Metabolites via Hybridization Assay

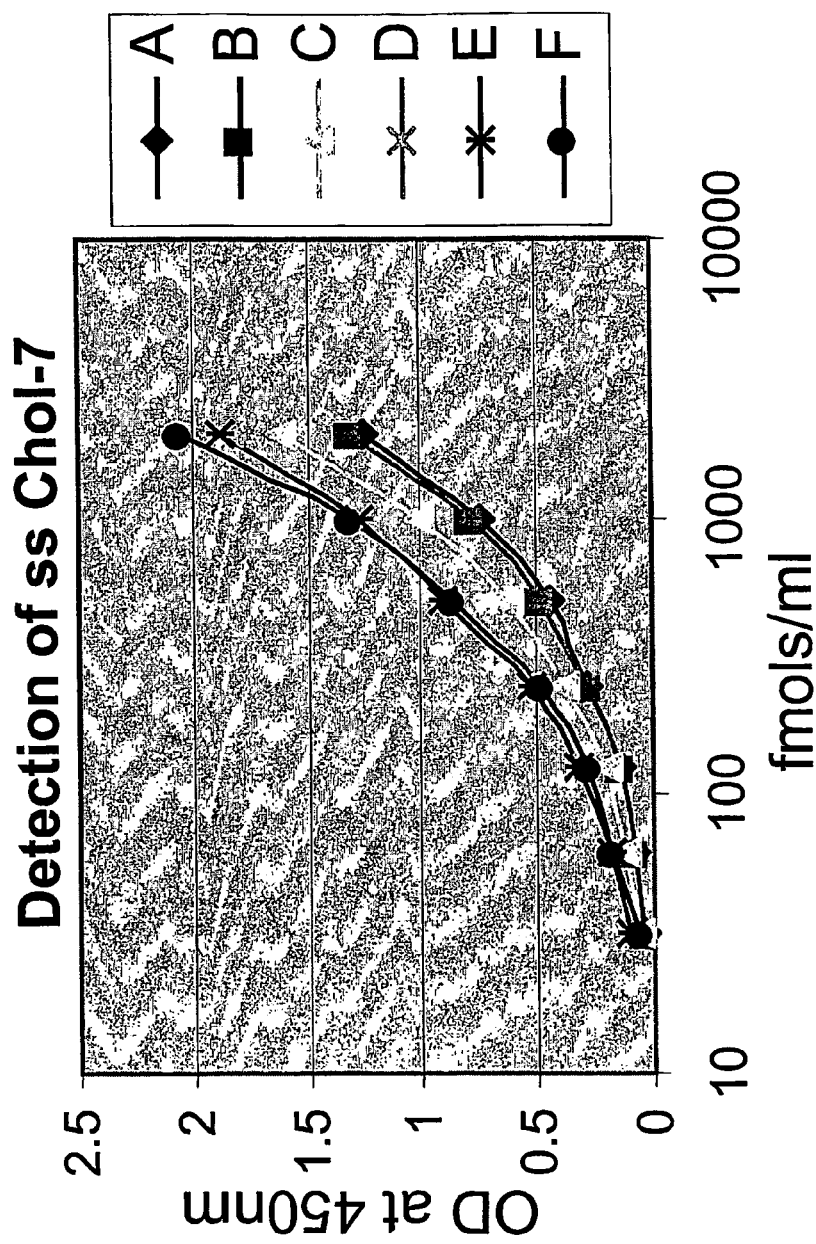
Figure 5A: Effect of Hepatocyte lysate on detection of single stranded Stab 7 cholesterol conjugate siNA sequence

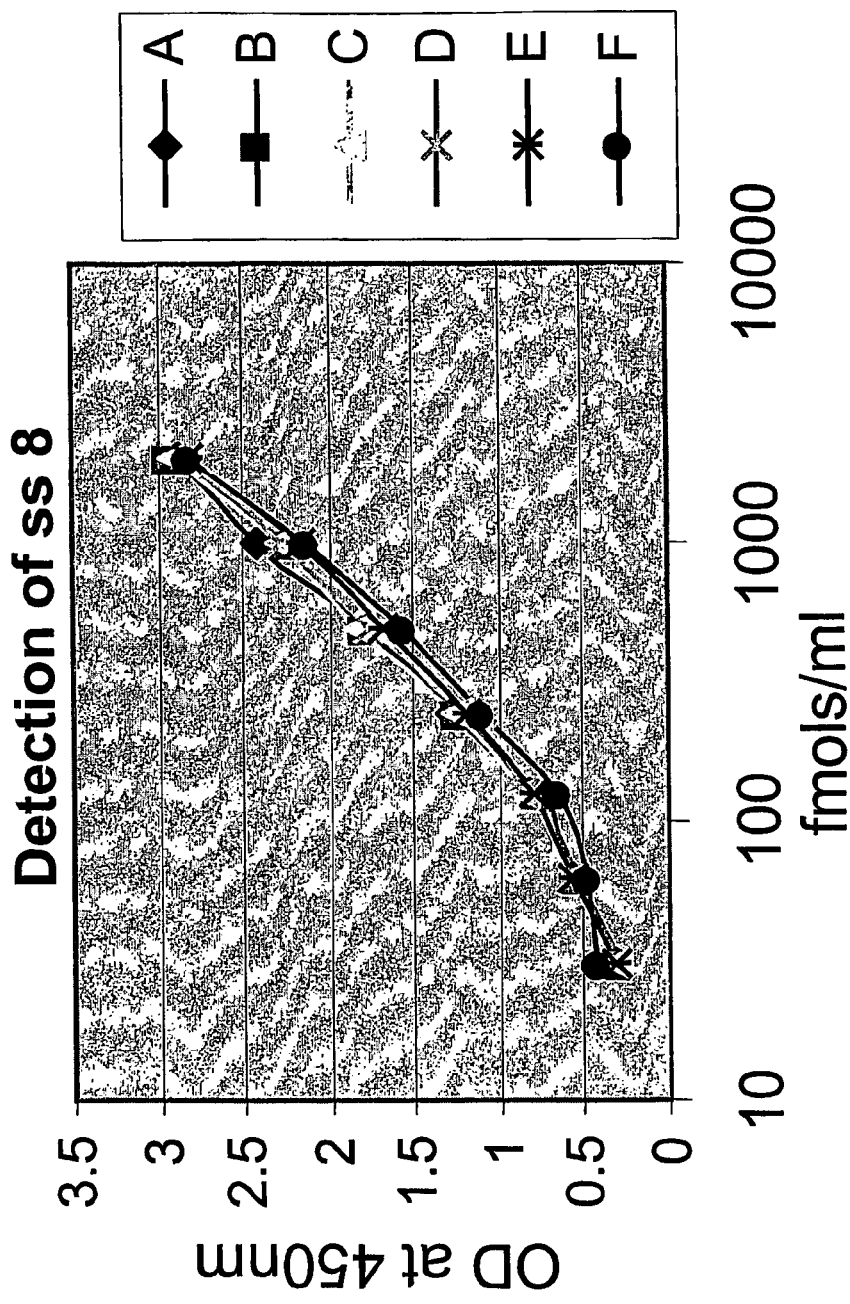
*Figure 5B: Effect of Hepatocyte lysate on detection of single stranded Stab 8 siNA sequence*

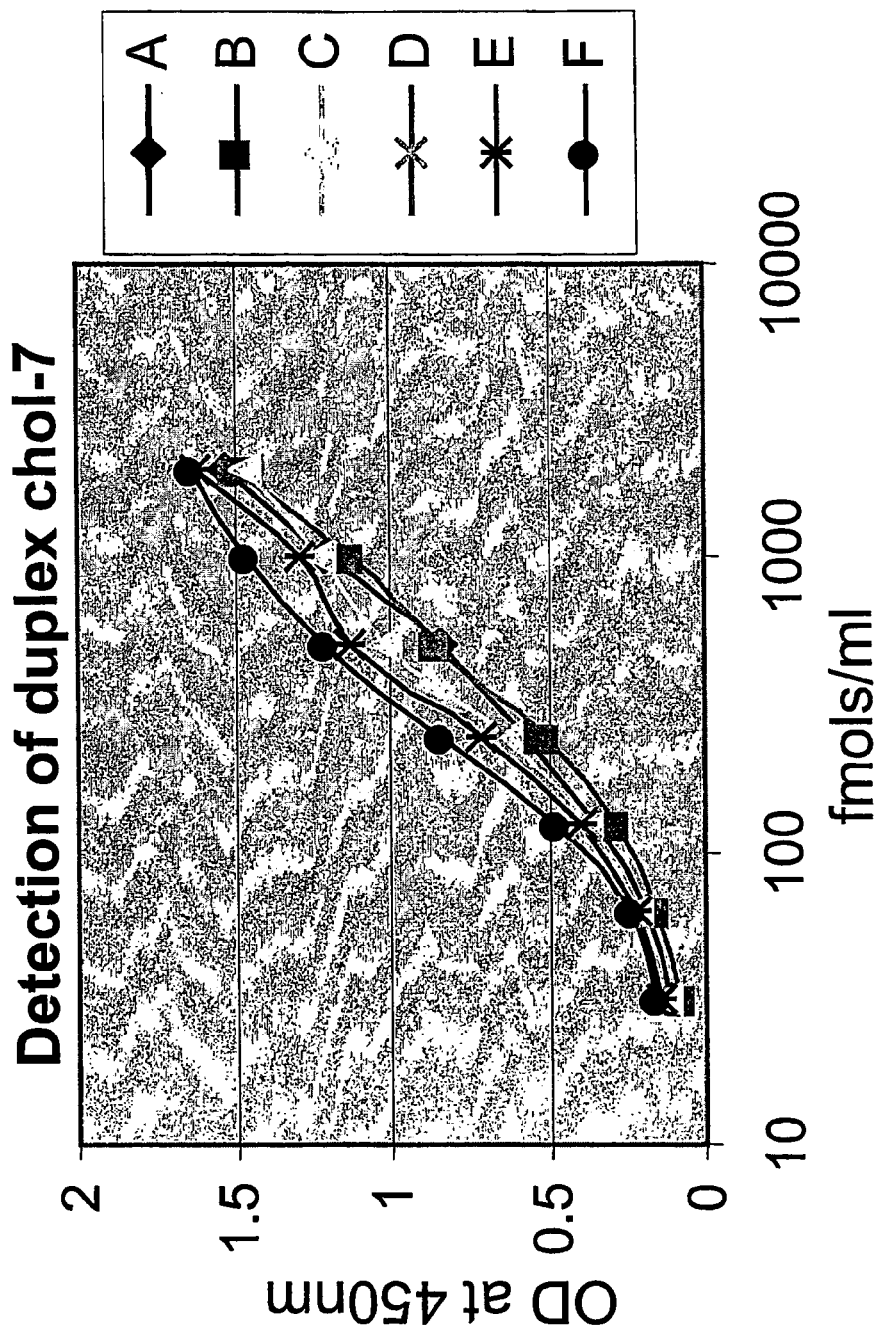
Figure 5C: Effect of Hepatocyte lysate on detection of Stab 7 cholesterol conjugate duplex siNA sequence

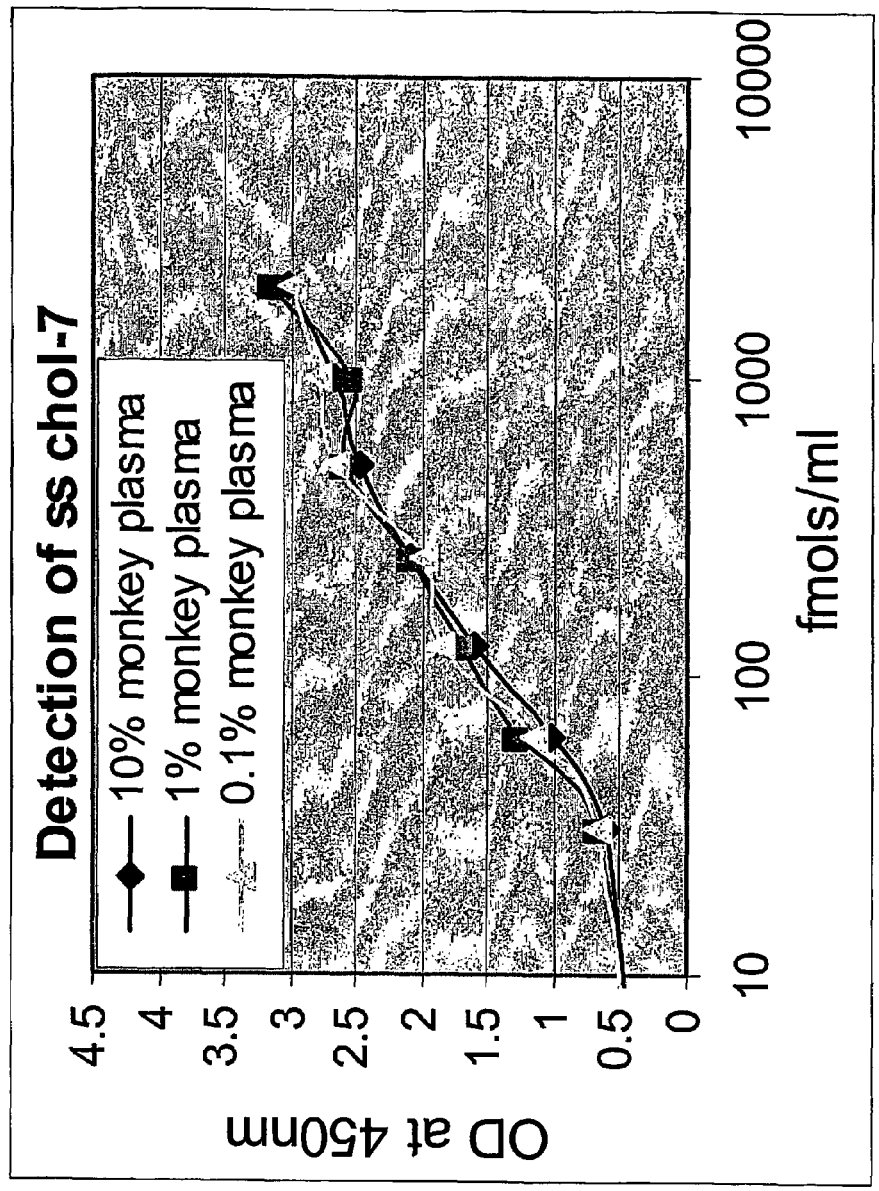
Figure 6A: Effect of monkey plasma on detection of single stranded Stab 7 cholesterol conjugate siNA sequence

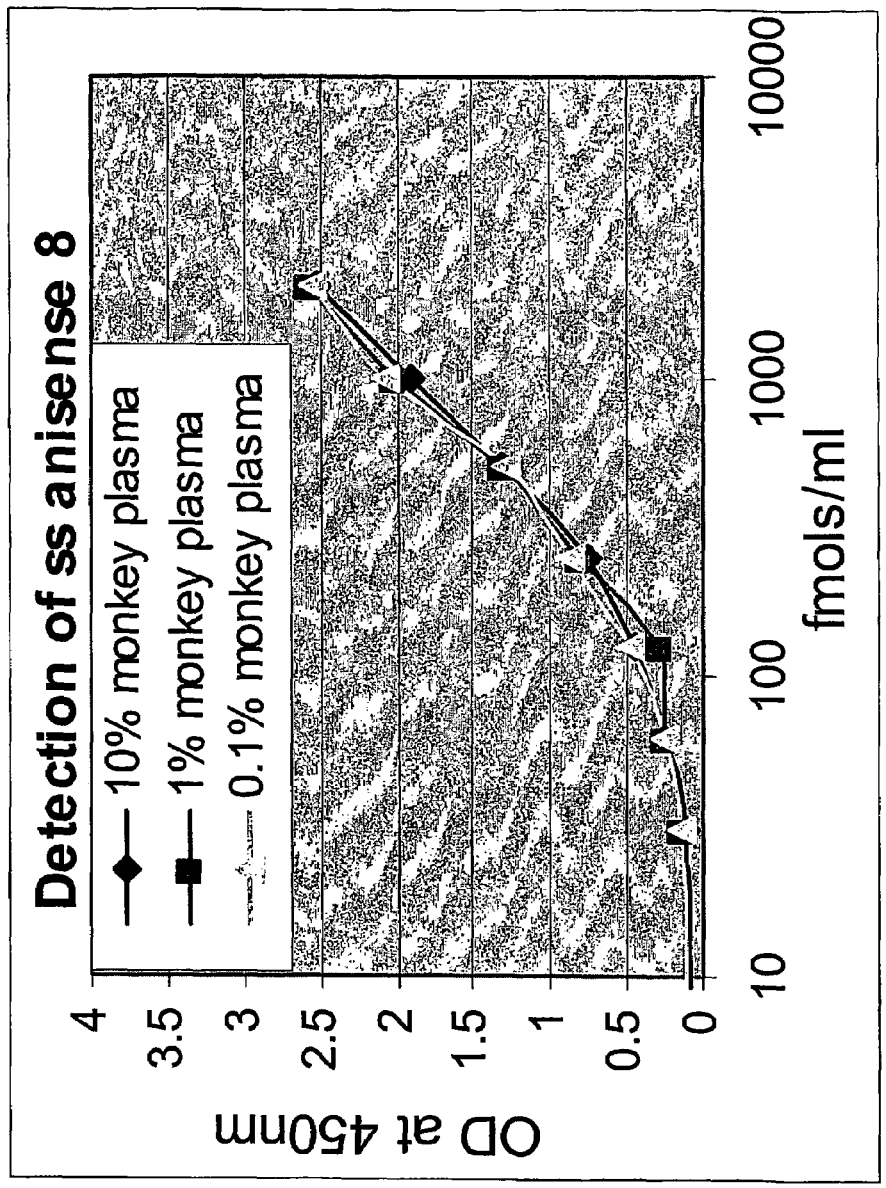
Figure 6B: Effect of monkey plasma on detection of single stranded Stab 8 siNA sequence

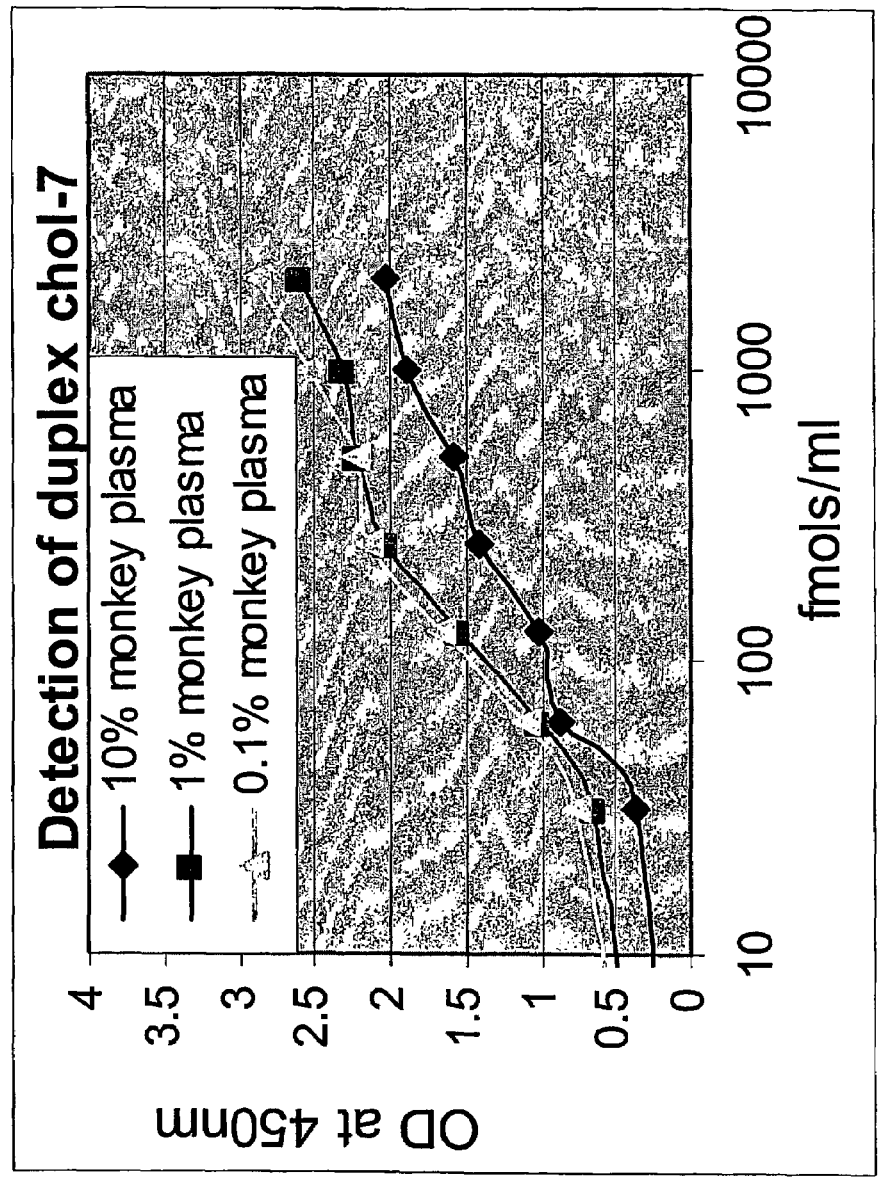
Figure 6C: Effect of monkey plasma on detection of Stab 7 cholesterol conjugate duplex siNA sequence

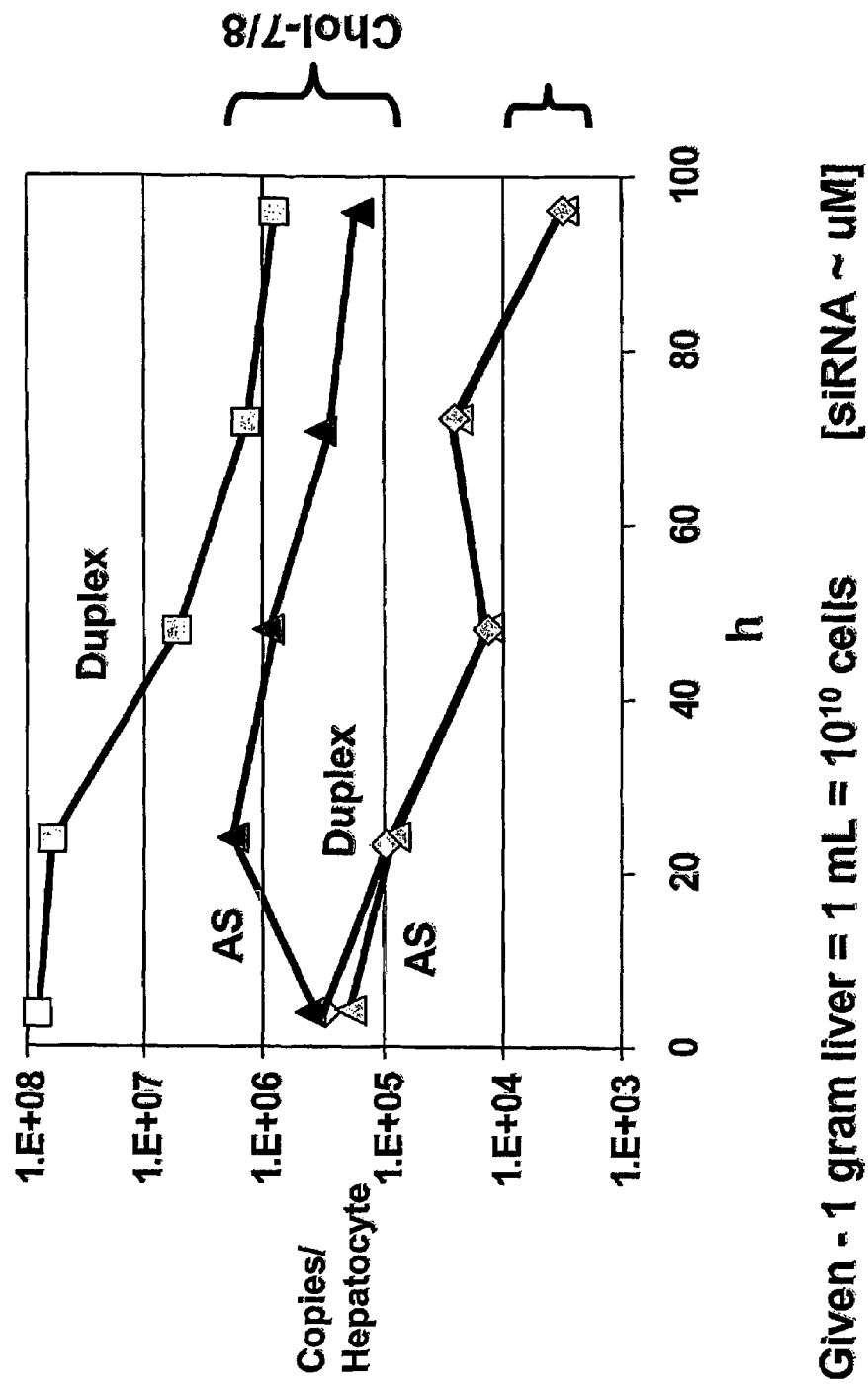
Figure 7: Concentration of siNA duplex and antisense In Hepatocytes
Given - 1 gram liver = 1 mL = $10^{10}$ cells

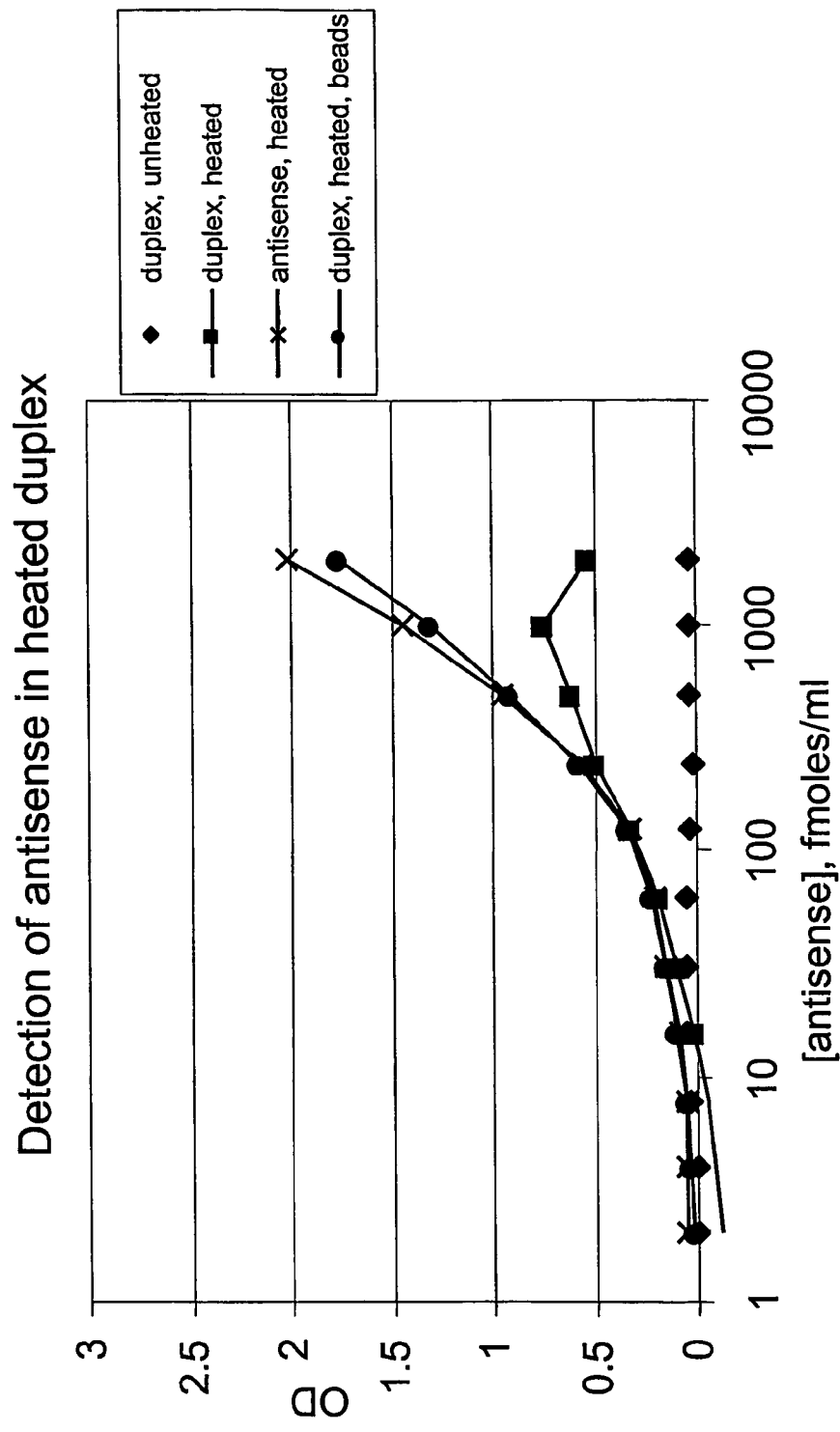
*Figure 8:* Removal of Competitive binding sequence in duplex assay

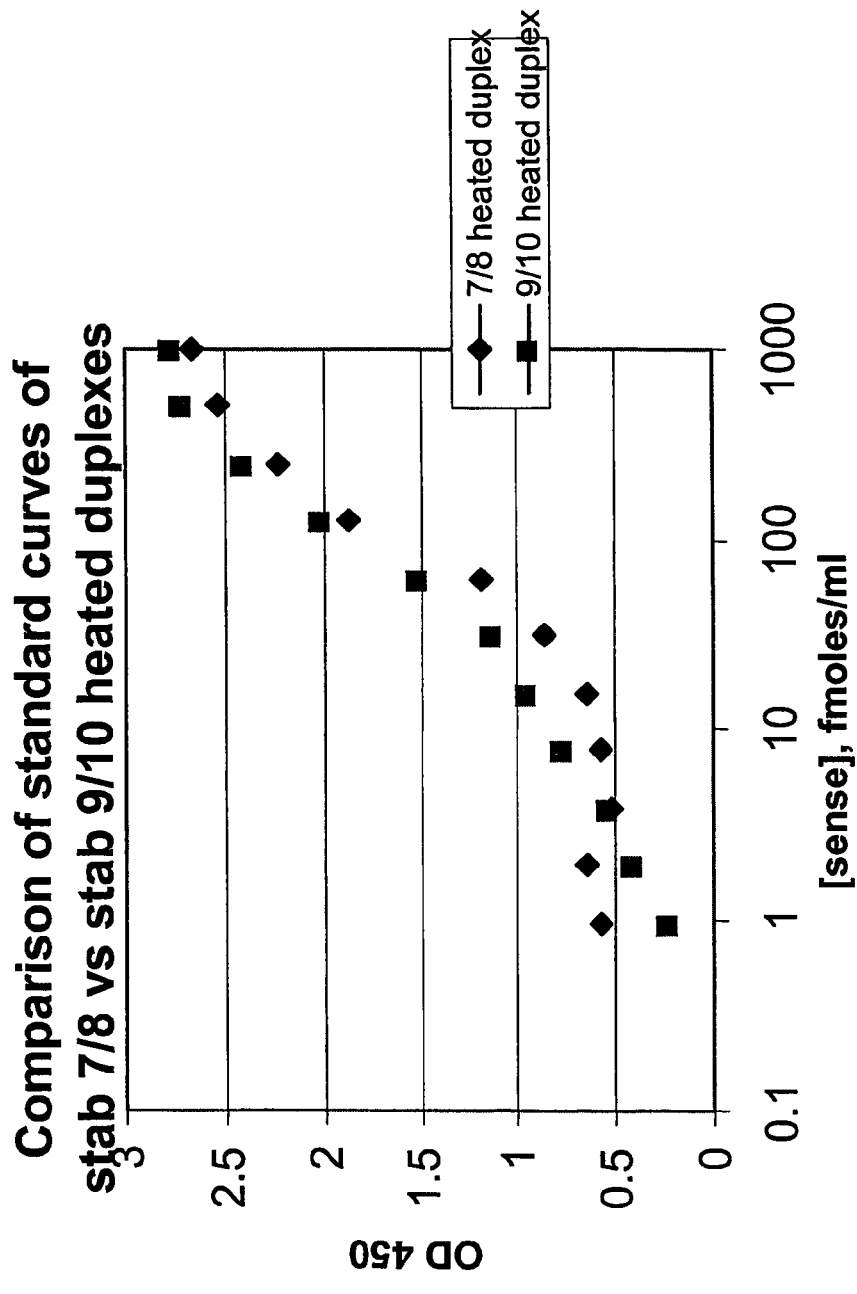
Figure 9: Application of Hybridization Assay to siNA molecules having identical sequence with differing chemical modifications Figure 11
A
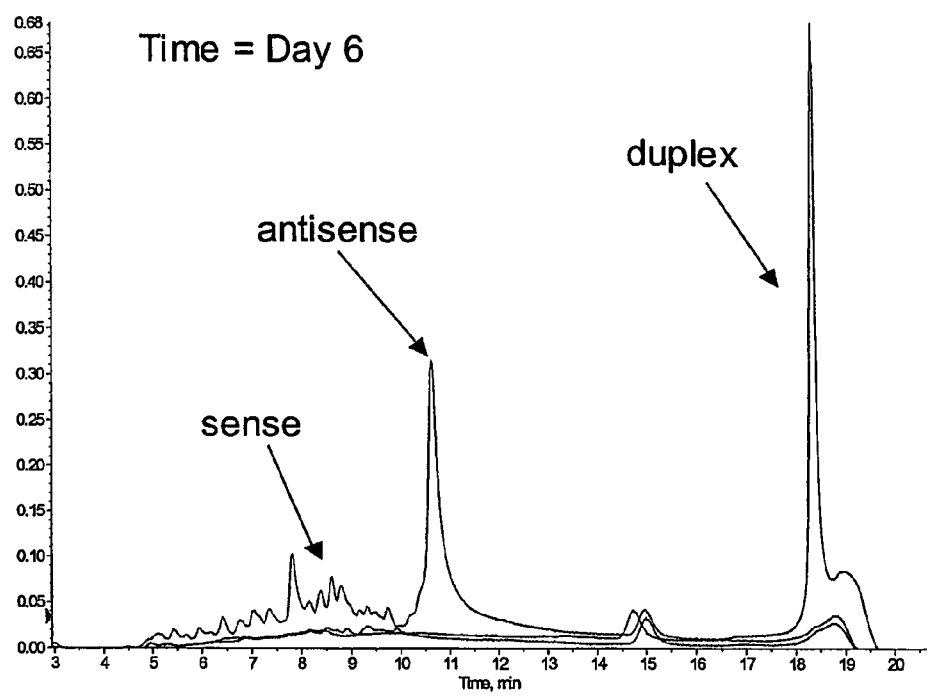
B
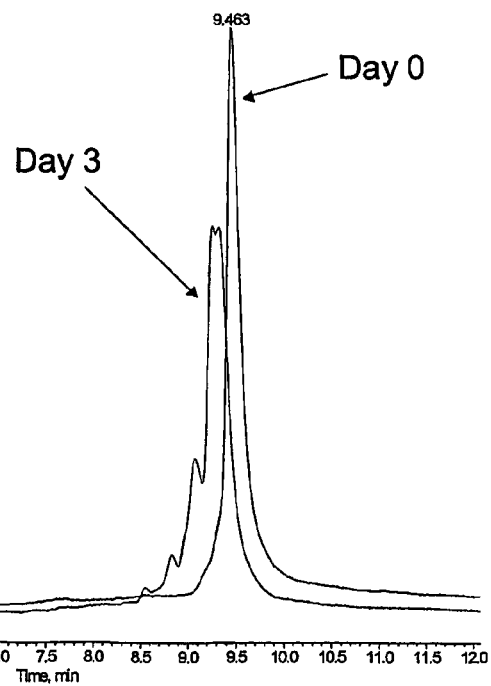

Figure 12
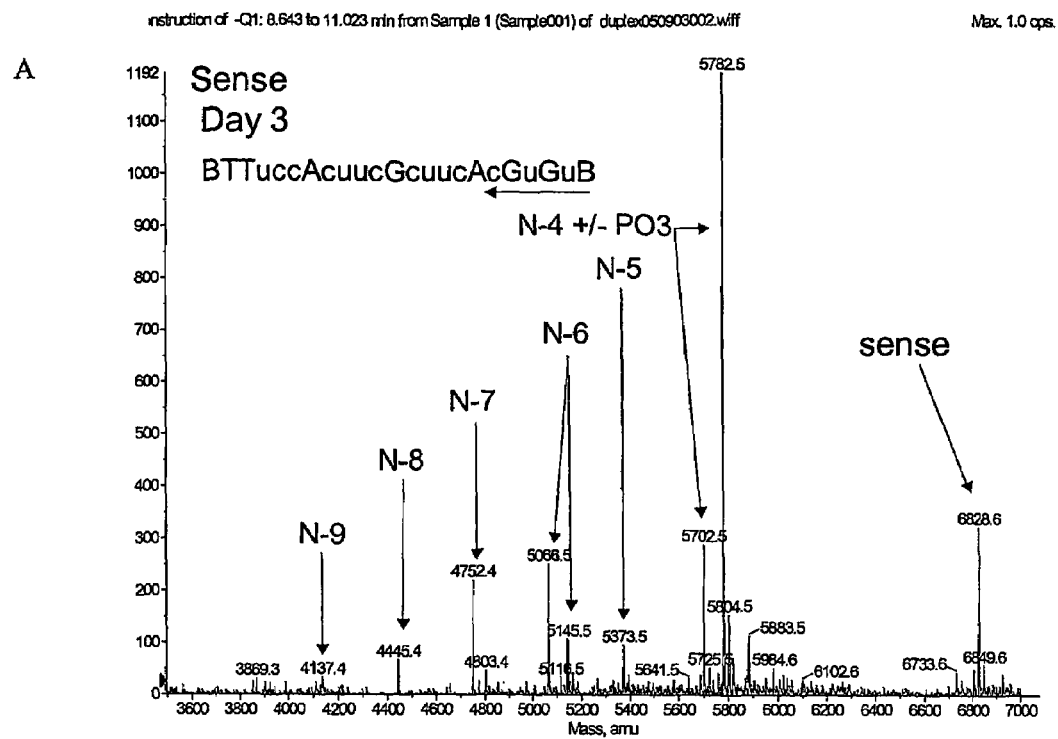
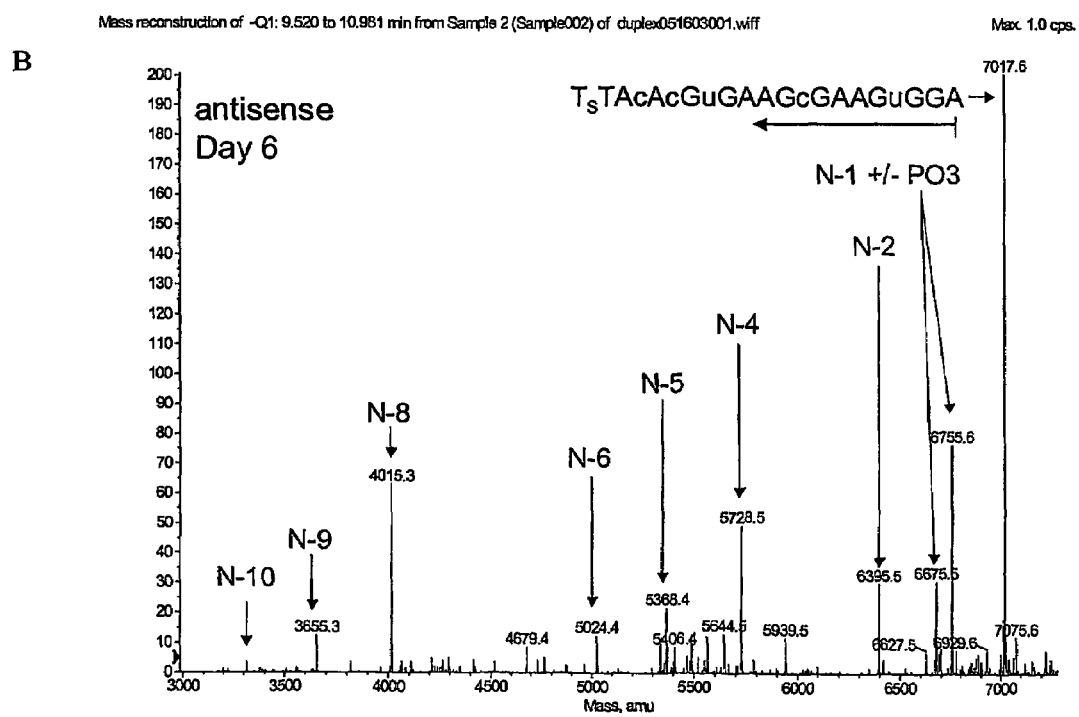

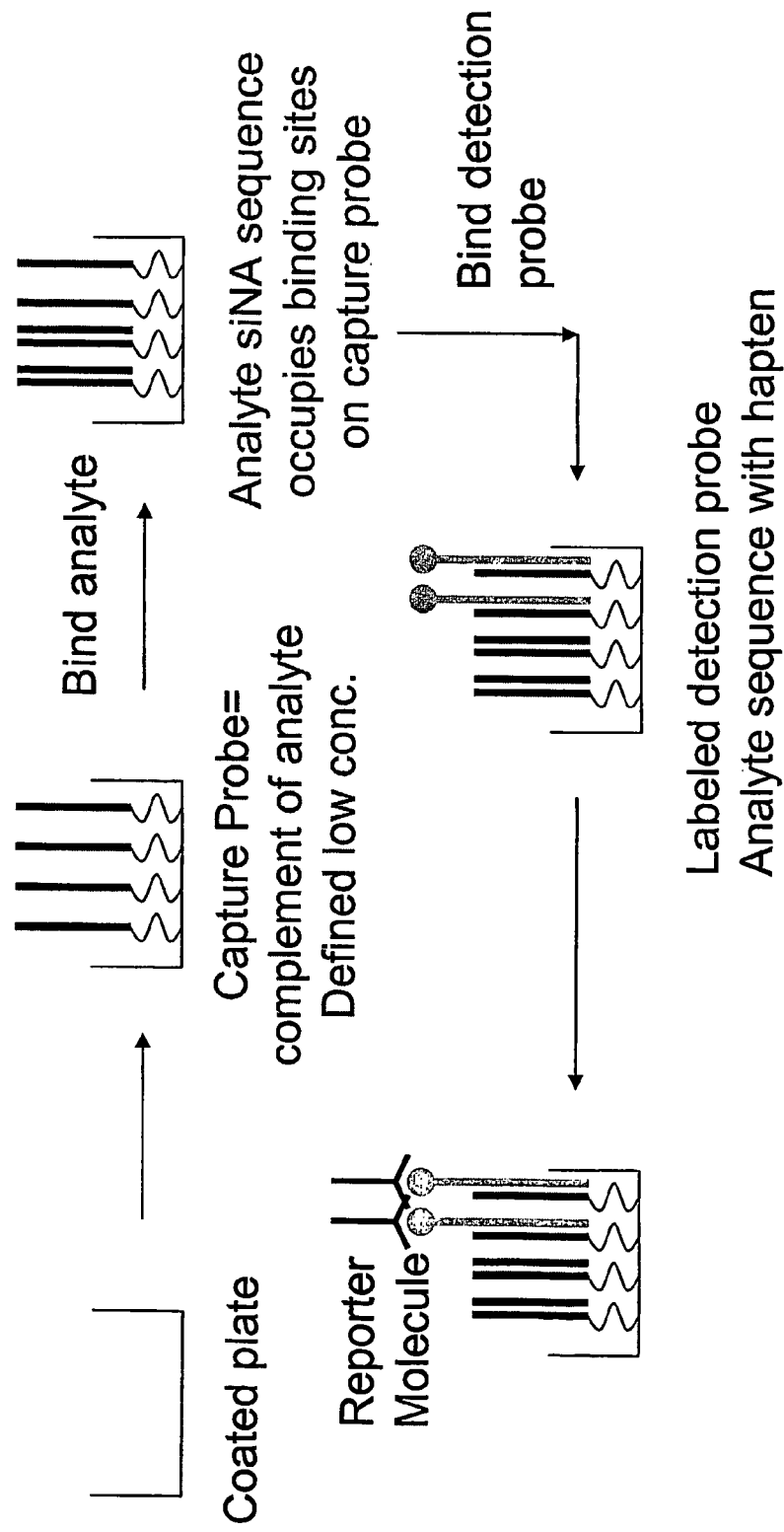

DETECTION AND QUANTITATION OF NUCLEIC ACID MOLECULES IN BIOLOGICAL SAMPLES This application also claims the benefit of U.S. Provisional Application No. 60/497,222, filed Aug. 22, 2003 and U.S. Provisional Application No. 60/543,784, filed Feb. 11, 2004, which are hereby incorporated by reference herein in their entireties, including the drawings.

FIELD OF THE INVNETION

The present invention concerns processes for the detection and quantitation of nucleic acid molecules, polynucleotides, and/or oligonucleotides in a sample using hybridization-detection assays, antibody-mediated recognition assays, nucleic acid sensor molecules, chromatographic assays, and/or electrophoresis assays. The present invention specifically concerns processes for the detection and quantitation of double stranded nucleic acid molecules, polynucleotides, and/or oligonucleotides in a sample using hybridization-detection assays. The nucleic acid molecules, polynucleotides, and/or oligonucleotides can include molecules that mediate RNA interference, such as short interfering nucleic acid (siNA), short interfering RNA (siRNA), double-stranded RNA (dsRNA), micro-RNA (miRNA), and short hairpin RNA (shRNA) molecules. The nucleic acid molecules, polynucleotides, and/or oligonucleotides can include nucleic acid aptamers, enzymatic nucleic acid molecules, decoys, antisense, 2',5'-oligoadenylate molecules, triplex forming oligonucleotides or any other nucleic acid molecule of interest. The present invention also concerns kits that allow for the detection and quantitation of nucleic acid molecules, polynucleotides, and/or oligonucleotides in a sample.

BACKGROUND OF THE INVNETION

The following is a discussion of relevant art pertaining to nucleic acid detection techniques. The discussion is provided only for understanding of the invention that follows. The summary is not an admission that any of the work described below is prior art to the claimed invention.

Nucleic acid molecules such as double stranded RNA (e.g., siRNA), antisense, ribozymes, DNAzymes, aptamers, decoys, 2',5'-oligoadenylate molecules and triplex forming oligonucleotides, are becoming increasingly important therapeutic modalities for the treatment of disease. As these molecules are developed as drugs, the need arises to detect the presence of, and/or measure the concentrations of these compounds in biological samples in order to optimize drug design, and to monitor and optimize patient treatment regimens. Conventional approaches to bioanalytical quantitation of nucleic acid molecules have included HPCL analysis and electrophoresis, such as capillary gel electrophoresis. These approaches tend to have limited sensitivity (e.g., from 50 to 100 ng/mL), and are time intensive because they require extraction of the nucleic acid of interest from a biological sample or matrix. Furthermore, this extraction step can contribute to limited assay sensitivity dut to incomplete recovery of the analyte. Other detection methods for quantitating nucleic acid molecules in biological samples include the use of radio-labeled oligonucleotides. However, the use to radiolabeled nucleotides is limited with regard to pre-clinical research settings and are not suitable for use in human subjects. Alternative methods often rely upon hybridization sandwich assays that can detect single stranded oligonucleotides in a sample. For example, Ishii et al., U.S. Pat. No. 5,474,895, describes certain nucleic acid sandwich hybridization assays for detecting single stranded oligonucleotides using polystyrene solid supports. Holtke et al., U.S. Pat. No. 5,354,657, describes certain processes for the detection of single stranded nucleic acids using certain nucleic acid sandwich hybridization assays that utilize a steroid hapten detection probe. Usman et al., International PCT Publication No. WO 01/66721, describes nucleic acid sensor molecules including halfzymes for detecting and quantitating nucleic acids, polynucleotides and oligonucleotides in a sample. Seiwert et aL, International PCT Application No. PCT/US02/35529, describes nucleic acid sensor molecules including halfzymes for detecting and quantitating nucleic acids, polynucleotides and oligonucleotides in a sample. Radka et al., U.S. Ser. No. 10/366,191, describes the use of antibody mediated detection assays for detecting and quantitating nucleic acids, polynucleotides and oligonucleotides in a sample.

SUMMARY OF THE INVENTION

The present invention concerns processes for the detection and quantitation of nucleic acid molecules, polynucleotides, and/or oligonucleotides in a sample using hybridization-detection assays, antibody-mediated recognition assays, nucleic acid sensor molecules, chromatographic assays, and/or electrophoresis assays. The present invention specifically concerns processes for the detection and quantitation of double stranded nucleic acid molecules, polynucleotides, and/or oligonucleotides in a sample using hybridization-detection assays. The nucleic acid molecules, polynucleotides, and/or oligonucleotides can include molecules that mediate RNA interference, such as short interfering nucleic acid (siNA), short interfering RNA (siRNA), double-stranded RNA (dsRNA), micro-RNA (miRNA), and short hairpin RNA (shRNA) molecules. The nucleic acid molecules, polynucleotides, and/or oligonucleotides can include nucleic acid aptamers, enzymatic nucleic acid molecules, decoys, antisense, 2',5'-oligoadenylate molecules, triplex forming oligonucleotides or any other nucleic acid molecule of interest. The present invention also concerns kits that allow for the detection and quantitation of nucleic acid molecules, polynucleotides, and/or oligonucleotides in a sample.

In one embodiment, the invention features a method for determining the concentration of a double stranded nucleic acid molecule in a biological sample, comprising: (a) obtaining a biological sample from a subject; (b) assaying a first portion of the sample for the concentration of any unhybridized single stranded component of the double stranded nucleic acid molecule under conditions suitable to determine the concentration of the unhybridized single stranded component in the sample; (c) processing a second portion of the sample under conditions suitable for any double stranded nucleic acid molecule present in the sample to dissassociate into one or more single stranded components; (d) assaying the second portion for the concentration of any dissassociated single stranded component of the double stranded nucleic acid molecule under conditions suitable to determine the concentration of the dissassociated single stranded component in the sample; and (e) comparing the concentration of the unhybridized single stranded component to the concentration of the dissassociated single stranded component under conditions suitable to determine the concentration of the double stranded nucleic acid molecule in the sample. In another embodiment, the processing in (c) above comprises heating the second portion at about 85 to about 95 degrees C. (e.g., 90 degrees C.) for about 5 to about 30 minutes (e.g., 10 minutes).

In one embodiment, this aspect of the method of the invention is illustrated generally in FIG. 1.

In one embodiment, the double stranded nucleic acid molecule comprises a nucleic acid molecule that mediates RNA interference. In another embodiment, the nucleic acid molecule that mediates RNA interference is a short interfering nucleic acid molecule (siNA). In another embodiment the double stranded nucleic acid molecule comprises a aptamer, enzymatic nucleic acid, decoy, antisense, 2',5'-oligoadenylate, or triplex forming oligonucleotide.

In one embodiment, the assaying step (b) above in the method for determining the concentration of a double stranded nucleic acid molecule in a biological sample comprises: (i) combining the first portion of the sample with a capture oligonucleotide affixed to a surface under conditions suitable for the capture oligonucleotide to specifically hybridize with a first portion of the unhybridized single stranded component; (ii) washing the surface under conditions suitable to remove any unbound portion of the double stranded nucleic acid molecule; (iii) adding a detection oligonucleotide to the surface of (ii) under conditions suitable for the detection oligonucleotide to specifically hybridize with a second portion of the unhybridized single stranded component; (iv) washing the surface under conditions suitable to remove any unbound detection oligonucleotide; (v) adding a reporter molecule to the surface of (iv); (vi) washing the surface under conditions suitable to remove any unbound or unreacted reporter molecule; (vii) measuring the amount of the bound or reacted reporter molecule; and (viii) determining the concentration of the unhybridized single stranded component by comparing the amount of the reporter molecule with a standard curve.

In one embodiment, the assaying step (b) above in the method for determining the concentration of double stranded nucleic acid molecule in a biological sample comprises: (i) combining the first portion of the sample with a detection oligonucleotide under conditions suitable for the detection oligonucleotide to specifically hybridize with a first portion of the unhybridized single stranded component; (ii) combining the product of (i) with a capture oligonucleotide affixed to a surface under conditions suitable for the capture oligonucleotide to specifically hybridize with a second portion of the unhybridized single stranded component; (iii) washing the surface under conditions suitable to remove any unbound detection oligonucleotide complex; (iv) adding a reporter molecule to the surface of (iii); (v) washing the surface under conditions suitable to remove any unbound or unreacted reporter molecule; (vi) measuring the amount of the bound or reacted reporter molecule; and (vii) determining the concentration of the unhybridized single stranded by comparing the amount of the reporter molecule with a standard curve.

In one embodiment, the assaying step (b) above in the method for determining the concentration of a double stranded nucleic acid molecule in a biological sample comprises: (i) combining a detection oligonucleotide with a capture oligonucleotide affixed to a surface; (ii) combining the first portion of the sample with the product of (i) under conditions suitable for the capture oligonucleotide to specifically hybridize with a first portion of the unhybridized single stranded component and for the detection oligonucleotide to specifically hybridize with a second portion of the unhybridized single stranded component; (iii) washing the surface under conditions suitable to remove any unbound detection oligonucleotide; (iv) adding a reporter molecule to the surface of (iii); (v) washing the surface under conditions suitable to remove any unbound or unreacted reporter molecule; (vi) measuring the amount of the bound or reacted reporter molecule; and (vii) determining the concentration of the unhybridized single stranded component by comparing the amount of the reporter molecule with a standard curve.

In one embodiment, the assaying step (d) above in the method for determining the concentration of a double stranded nucleic acid molecule in a biological sample comprises: (i) combining the second portion of the sample with a capture oligonucleotide affixed to a surface under conditions suitable for the capture oligonucleotide to specifically hybridize with a first portion of the dissassociated single stranded component; (ii) washing the surface under conditions suitable to remove any unbound portion of the double stranded nucleic acid molecule; (iii) adding a detection oligonucleotide to the surface of (ii) under conditions suitable for the detection oligonucleotide to specifically hybridize with a second portion of the the dissassociated single stranded component; (iv) washing the surface under conditions suitable to remove any unbound detection oligonucleotide; (v) adding a reporter molecule to the surface of (iv); (vi) washing the surface under conditions suitable to remove any unbound or unreacted reporter molecule; (vii) measuring the amount of the bound or reacted reporter molecule; and (viii) determining the concentration of the the dissassociated single stranded component by comparing the amount of the reporter molecule with a standard curve.

In one embodiment, the assaying step (d) above in the method for determining the concentration of a double stranded nucleic acid molecule in a biological sample comprises: (i) combining the second portion of the sample with a detection oligonucleotide under conditions suitable for the detection oligonucleotide to specifically hybridize with a first portion of the dissassociated single stranded component; (ii) combining the product of (i) with a capture oligonucleotide affixed to a surface under conditions suitable for the capture oligonucleotide to specifically hybridize with a second portion of the dissassociated single stranded component; (iii) washing the surface under conditions suitable to remove any unbound detection oligonucleotide complex; (iv) adding a reporter molecule to the surface of (iii); (v) washing the surface under conditions suitable to remove any unbound or unreacted reporter molecule; (vi) measuring the amount of the bound or reacted reporter molecule; and (vii) determining the concentration of the dissassociated single stranded component by comparing the amount of the reporter molecule with a standard curve.

In one embodiment, the assaying step (d) above in the method for determining the concentration of a double stranded nucleic acid molecule in a biological sample comprises: (i) combining the second portion of the sample with a labeled capture oligonucleotide affixed to a surface under conditions suitable for the labeled capture oligonucleotide to specifically hybridize with a first portion of the dissassociated single stranded component; (ii) washing the surface under conditions suitable to remove any unbound portion of the double stranded nucleic acid molecule; (iii) adding a nuclease with nuclease activity specific for single stranded polynucleotides to the surface of (ii) under conditions suitable for the nuclease to cleave any non-hybridized labeled capture oligonucleotide from the surface; (iv) washing the surface under conditions suitable to remove any cleaved labeled capture oligonucleotide; (v) measuring the amount of the bound labeled capture oligonucleotide remaining on the surface; and (vi) determining the concentration of the the dissassociated single stranded component by comparing the amount of the signal from the remaining capture oligonucleotide (e.g., which is hybridized with the single stranded component to be detected) with a standard curve. In one embodiment, the label is fluorescein. In one embodiment, this aspect of the method of the invention is illustrated generally in FIG. 14.

In one embodiment, the assaying step (d) above in the method for determining the concentration of a double stranded nucleic acid molecule in a biological sample comprises: (i) combining the second portion of the sample with a capture oligonucleotide affixed to a surface under conditions suitable for the capture oligonucleotide to specifically hybridize with a first portion of the dissassociated single stranded component; (ii) washing the surface under conditions suitable to remove any unbound portion of the double stranded nucleic acid molecule; (iii) adding a detection oligonucleotide to the surface of (ii) under conditions suitable for the detection oligonucleotide to specifically hybridize with any non-hybridized capture oligonucleotide (e.g., any capture oligonucleotide that is not complexed with the dissassociated single stranded component to be quantitated); (iv) washing the surface under conditions suitable to remove any unbound detection oligonucleotide; (v) adding a reporter molecule to the surface of (iv); (vi) washing the surface under conditions suitable to remove any unbound or unreacted reporter molecule; (vii) measuring the amount of the bound or reacted reporter molecule; and (viii) determining the concentration of the the dissassociated single stranded component by comparing the amount of the reporter molecule with a standard curve. In this aspect of the method, the signal generated from the assay is inversely proportional to the analyte concentration. In one embodiment, this aspect of the method of the invention is illustrated generally in FIG. 15.

In one embodiment, the step (c) above in the method for determining the concentration of a double stranded nucleic acid molecule in a biological sample further comprises removing any single stranded component of double stranded nucleic acid molecule from the sample that can competetively bind to the other single stranded component of the double stranded nucleic acid molecule that is to be assayed in step (d) above to arrive at the concentration of double stranded nucleic acid molecule in the sample. This step can be useful, for example at higher assay concentrations, to prevent duplex formation before the single stranded component of the double stranded nucleic acid molecule to be quantified can be quantitatively assayed due to competetive binding of the complementary non-assay siNA sequence. Such non-assay single stranded component can be removed by any methodology as is known in the art, such as by affinity capture using a biotinylated complementary sequence. In one embodiment, the sample is heated to about 90 degrees C. for about 10 minutes followed by treatment with a streptavidin conjugated complementary oligonucleotide sequence that binds to the non-assay single stranded siNA component which is then removed from the assay by any suitable means, such as centrifugation or affinity capture.

In one embodiment, the invention features a method for determining the concentration of a double stranded nucleic acid molecule in a biological sample, comprising: (a) processing a biological sample under conditions suitable for any double stranded nucleic acid molecule present in the sample to dissassociate into one or more single stranded components; and (b) assaying the sample for the level of one or more single stranded components of the double stranded nulceic acid molecule under conditions suitable to determine the level of the double stranded nucleic acid molecule in the sample. In another embodiment, the double stranded nucleic acid molecule comprises a siNA. The siNA molecule can comprise a sense strand and an antisense strand. In one embodiment, the single stranded component comprises the sense strand of the siNA. In another embodiment, the single stranded component comprises the antisense strand of the siNA. In one embodiment, the siNA comprises a hairpin seqeunce, for example where the single stranded component comprises the hairpin sequence in linear form. In another embodiment, the processing of the sample comprises heating the sample at about 75 to about 95 degrees C. for about 5 to about 30 minutes.

In one embodiment, the invention features a method of detecting the presence of one or more siNA molecules in a biological sample, comprising: (a) obtaining a biological sample from a subject; (b) contacting the sample with one or more reagents capable of detecting the presence of a siNA molecule in the sample; and (c) assaying the sample under conditions suitable for the detection. In one embodiment, the reagents capable of detecting the presence of the siNA molecule in the sample include components of a hybridization-detection assay, such as capture oligonucleotides, detection oligonucleotides, reporter molecules, and any other reagent required for a hybridization-detection assay. In one embodiment, the reagents capable of detecting the presence of the siNA molecule in the sample include the components of an antibody detection assay, such as antibodies, reporter molecules, labels, and any other reagent required for an antibody detection assay. In one embodiment, the reagents capable of detecting the presence of the siNA molecule in the sample include the components of a chromoatographic detection assay, such as extraction reagents, reporter molecules, labels, elution buffers, chromatography media detection reagents, and any other reagent required for a chromatographic detection assay. In one embodiment, the reagents capable of detecting the presence of the siNA molecule in the sample include the components of an electrophoretic detection assay, such as extraction reagents, reporter molecules, labels, electrophoretic matrices, and any other reagent required for an electrophoretic detection assay. In one embodiment, the reagents capable of detecting the presence of the siNA molecule in the sample include the components of a nucleic acid sensor molecule detection assay, such as enzymatic nucleic acid molecules, reporter molecules, aptamers, and any other reagent required for a nucleic acid sensor molecule detection assay. In one embodiment, the above method for detecting the presence of one or more siNA molecules in a biological sample is adapted for use to determine the concentration of the siNA molecule(s) in the sample, for example by quantitative assay in step (c) above.

In one embodiment, the invention features a method for determining the concentration of a siNA in a biological sample, comprising: (a) obtaining a biological sample from a subject; and (b) assaying the sample under conditions suitable to determine the concentration of the siNA in the sample. In one embodiment, the assaying step (b) above can comprise a hybridization-detection assay. In another embodiment, the assaying step (b) above can comprise an antibody detection assay. In another embodiment, the assaying step (b) above can comprise a chromoatographic detection assay. In another embodiment, the assaying step (b) above can comprise an electrophoretic detection assay. In another embodiment, the assaying step (b) above can comprise a nucleic acid sensor molecule detection assay.

In one embodiment, the invention features a method for determining the concentration of a single stranded siNA in a biological sample, comprising: (a) obtaining a biological sample from a subject; (b) processing the sample under denaturing conditions; and (c) assaying the sample under conditions suitable to determine the concentration of the single stranded siNA in the sample. In another embodiment, the processing in (b) above comprises heating the second portion at about 85 to about 95 degrees C. (e.g., 90 degrees C.) for about 5 to about 30 minutes (e.g., 10 minutes). In one embodiment, the siNA comprises a self complementary sequence, such as a hairpin structure. In one embodiment, the assaying step (c) above can comprise a hybridization-detection assay. In another embodiment, the assaying step (c) above can comprise an antibody detection assay. In another embodiment, the assaying step (c) above can comprise a chromoatographic detection assay. In another embodiment, the assaying step (c) above can comprise an electrophoretic detection assay. In another embodiment, the assaying step (c) above can comprise a nucleic acid sensor molecule detection assay.

In one embodiment, the invention features a method for determining the concentration of a siNA duplex in a biological sample, comprising: (a) obtaining a biological sample from a subject; (b) assaying a first portion of the sample for the concentration of any unhybridized single stranded component of the siNA duplex under conditions suitable to determine the concentration of the unhybridized single stranded component in the sample; (c) processing a second portion of the sample under conditions suitable for any siNA duplex present in the sample to dissassociate into one or more single stranded components; (d) assaying the second portion for the concentration of any dissassociated single stranded component of the siNA duplex under conditions suitable to determine the concentration of the dissassociated single stranded component in the sample; and (e) comparing the concentration of the unhybridized single stranded component to the concentration of the dissassociated single stranded component under conditions suitable to determine the concentration of the siNA duplex in the sample. In another embodiment, the processing in (c) above comprises heating the second portion at about 85 to about 95 degrees C. (e.g., 90 degrees C.) for about 5 to about 30 minutes (e.g., 10 minutes). In one embodiment, the siNA duplex can comprise a sense strand and an antisense strand. In one embodiment, the single stranded component comprises the sense strand of the siNA. In another embodiment, the single stranded component comprises the antisense strand of the siNA. In one embodiment, the assaying steps (b) and (d) above can comprise a hybridization-detection assay. In another embodiment, the assaying steps (b) and (d) above can comprise an antibody detection assay. In another embodiment, the assaying steps (b) and (d) above can comprise a chromatographic detection assay. In another embodiment, the assaying steps (b) and (d) above can comprise an electrophoretic detection assay. In another embodiment, the assaying steps (b) and (d) above can comprise a nucleic acid sensor molecule detection assay.

In one embodiment, the assaying step (b) above in the method for determining the concentration of a siNA duplex in a biological sample comprises: (i) combining the first portion of the sample with a capture oligonucleotide affixed to a surface under conditions suitable for the capture oligonucleotide to specifically hybridize with a first portion of the siNA sequence; (ii) washing the surface under conditions suitable to remove any unbound portion of the siNA; (iii) adding a detection oligonucleotide to the surface of (ii) under conditions suitable for the detection oligonucleotide to specifically hybridize with a second portion of the siNA sequence; (iv) washing the surface under conditions suitable to remove any unbound detection oligonucleotide; (v) adding a reporter molecule to the surface of (iv); (vi) washing the surface under conditions suitable to remove any unbound or unreacted reporter molecule; (vii) measuring the amount of the bound or reacted reporter molecule; and (viii) determining the concentration of the unhybridized single stranded component of the siNA by comparing the amount of the reporter molecule with a standard curve.

In one embodiment, the assaying step (b) above in the method for determining the concentration of a siNA in a biological sample comprises: (i) combining the first portion of the sample with a detection oligonucleotide under conditions suitable for the detection oligonucleotide to specifically hybridize with a first portion of the siNA sequence; (ii) combining the product of (i) with a capture oligonucleotide affixed to a surface under conditions suitable for the capture oligonucleotide to specifically hybridize with a second portion of the siNA sequence; (iii) washing the surface under conditions suitable to remove any unbound siNA-detection oligonucleotide complex; (iv) adding a reporter molecule to the surface of (iii); (v) washing the surface under conditions suitable to remove any unbound or unreacted reporter molecule; (vi) measuring the amount of the bound or reacted reporter molecule; and (vii) determining the concentration of the unhybridized single stranded component of the siNA by comparing the amount of the reporter molecule with a standard curve.

In one embodiment, the assaying step (d) above in the method for determining the concentration of a siNA in a biological sample comprises: (i) combining the second portion of the sample with a capture oligonucleotide affixed to a surface under conditions suitable for the capture oligonucleotide to specifically hybridize with a first portion of the siNA sequence; (ii) washing the surface under conditions suitable to remove any unbound portion of the siNA; (iii) adding a detection oligonucleotide to the surface of (ii) under conditions suitable for the detection oligonucleotide to specifically hybridize with a second portion of the siNA sequence; (iv) washing the surface under conditions suitable to remove any unbound detection oligonucleotide; (v) adding a reporter molecule to the surface of (iv); (vi) washing the surface under conditions suitable to remove any unbound or unreacted reporter molecule; (vii) measuring the amount of the bound or reacted reporter molecule; and (viii) determining the concentration of the dissassociated single stranded component of the siNA by comparing the amount of the reporter molecule with a standard curve.

In one embodiment, the assaying step (d) above in the method for determining the concentration of a siNA in a biological sample comprises: (i) combining the second portion of the sample with a detection oligonucleotide under conditions suitable for the detection oligonucleotide to specifically hybridize with a first portion of the siNA sequence; (ii) combining the product of (i) with a capture oligonucleotide affixed to a surface under conditions suitable for the capture oligonucleotide to specifically hybridize with a second portion of the siNA sequence; (iii) washing the surface under conditions suitable to remove any unbound siNA-detection oligonucleotide complex; (iv) adding a reporter molecule to the surface of (iii); (v) washing the surface under conditions suitable to remove any unbound or unreacted reporter molecule; (vi) measuring the amount of the bound or reacted reporter molecule; and (vii) determining the concentration of the dissassociated single stranded component of the siNA by comparing the amount of the reporter molecule with a standard curve.

In one embodiment, the step (c) above in the method for determining the concentration of a siNA duplex in a biological sample further comprises removing any single stranded component of siNA from the sample that can competetively bind to the other single stranded component of the siNA molecule that is to be assayed in step (d) above to arrive at the concentration of duplex in the sample. This step can be useful, for example at higher assay concentrations, to prevent duplex formation before the single stranded component of the siNA molecule to be quantified can be quantitatively assayed due to competetive binding of the complementary non-assay siNA sequence. Such non-assay single stranded component can be removed by any methodology as is known in the art, such as by affinity capture using a biotinylated complementary sequence. In one embodiment, the sample is heated to about 90 degrees C. for about 10 minutes followed by treatment with a streptavidin conjugated complementary oligonucleotide sequence that binds to the non-assay single stranded siNA component which is then removed from the assay by any suitable means, such as centrifugation or affinity capture.

In any of the above methods, the capture oligonucleotide is bound to the surface via a high affinity ligand pair interaction, such as a biotin-avidin, biotin-streptavidin, or biotin-neutravidin binding system. In another embodiment, the capture oligonucleotide is complementary to a first portion of the dissassociated single stranded component. In another embodiment, the detection oligonucleotide is complementary to a second portion of the dissassociated single stranded component. In another embodiment, the detection oligonucleotide comprises a FITC conjugated oligonucleotide, for example where the FITC moiety is conjugated at the 5'-end or 3'-end of the conjugated oligonucleotide. In another embodiment, the reporter molecule comprises a peroxidase labeled anti-FITC antibody.

In one embodiment, any one of the forgoing methods can be used to determine the concentration of any single stranded component of a siNA molecule, for example the concentration of the antisense strand of a siNA duplex, the concentration of the sense strand of a siNA duplex, the concentration of a hairpin siNA, and/or the concentration of a single stranded siNA. In another embodiment, the concentration of any unhybridized sense strand in a sample is added to the total concentration of the sense strand in the sample after any siNA duplex in the sample is dissassociated to arrive at the total concentration of the sense strand in the sample. In another embodiment, the concentration of any unhybridized antisense strand in a sample is added to the total concentration of the antisense strand in the sample after any siNA duplex in the sample is dissassociated to arrive at the total concentration of the antisense strand in the sample. In another embodiment, any one of the forgoing methods can be used to determine the ratio of unhybridized sense strand to hybridized sense strand in a sample. In another embodiment, any one of the forgoing methods can be used to determine the ratio of unhybridized antisense strand to hybridized antisense strand in a sample.

In one embodiment, any one of the forgoing methods can be used to determine the concentration of a siNA duplex. In another embodiment, the concentration of any unhybridized sense strand in a sample is subtracted from the total concentration of the sense strand in the sample after any siNA duplex in the sample is dissassociated to arrive at the concentration of the siNA duplex in the sample. In another embodiment, the concentration of any unhybridized antisense strand in a sample is subtracted from the total concentration of the antisense strand in the sample after any siNA duplex in the sample is dissassociated to arrive at the concentration of the siNA duplex in the sample.

In one embodiment, the capture oligonucleotide is about 4 to about 25 or more nucleotides in length (e.g., 4, 5, 6, 7, 8, 9, 10, 11, 12, 13, 14, 15, 16, 17, 18, 19, 20, 21, 22, 23, 24, 25, or more nucleotides in length). In one embodiment, the detection oligonucleotide is about 4 to about 25 or more nucleotides in length (e.g., 4, 5, 6, 7, 8, 9, 10, 11, 12, 13, 14, 15, 16, 17, 18, 19, 20, 21, 22, 23, 24, 25, or more nucleotides in length). In another embodiment, the length of the capture and detection oligonucleotides is designed based upon on length of the sequence to be detected. For example, for a 21 nucleic acid sequence to be detected, the capture oligonucleotide can comprise about 10 complementary nucleotides and the detection oligonucleotide can comprise about 11 nucleotides. In another example, for a 21 nucleic acid sequence to be detected, the capture oligonucleotide can comprise about 15 complementary nucleotides and the detection oligonucleotide can comprise about 6 nucleotides. All that is required is that the capture oligonucleotide and detection oligonucleotide be able to independently stably interact with the nucleic acid sequence to be detected in a hybridization-detection assay assay format, allowing for the accurate quantitation of the concentration of the nucleic acid sequence.

In one embodiment, in any one of the foregoing methods, the capture oligonucleotide is chemically modified at the nucleic acid sugar, base, and/or backbone position. Non-limiting examples of chemical modifications that can be introduced into the capture oligonucleotide include "locked nucleic acid" nucleotides such as a 2', 4'-C methylene bicyclo nucleotide (see for example Wengel et al., International PCT Publication No. WO 00/66604 and WO 99/14226), 2'-deoxy-2'-fluoro nucleotides, 2'-O-methyl nucleotides, 2'-O-methoxyethyl nucleotides, 2'-O-methyl-thio-methyl nucleotides, 2'-O-methyl-thio-ethyl nucleotides, 2'-deoxy-2'-amino nucleotides, 2'-O-amino nucleotides, 2'-guanidinyl nucleotides, 2'-O-guanidinyl nucleotides, 2'-deoxy nucleotides 2,6-diaminopurine nucleotides, and/or peptide nucleic acid (PNA).

In one embodiment, in any one of the foregoing methods, the detection oligonucleotide is chemically modified at the nucleic acid sugar, base, and/or backbone position. Non-limiting examples of chemical modifications that can be introduced into the capture oligonucleotide include "locked nucleic acid" nucleotides such as a 2', 4'-C methylene bicyclo nucleotide (see for example Wengel et al., International PCT Publication No. WO 00/66604 and WO 99/14226), 2'-deoxy-2'-fluoro nucleotides, 2'-O-methyl nucleotides, 2'-O-methoxyethyl nucleotides, 2'-O-methyl-thio-methyl nucleotides, '-O-methyl-thio-ethyl nucleotides, 2'-deoxy-2'-amino nucleotides, 2'-O-amino nucleotides, 2'-guanidinyl nucleotides, 2'-O-guanidinyl nucleotides, 2'-deoxy nucleotides 2,6-diaminopurine nucleotides, and/or peptide nucleic acid (PNA).

In one embodiment, in any one of the foregoing methods, the target nucleic acid sequence (e.g., siNA sequence) is amplified prior to hybridization to the capture oligonucleotide.

In one embodiment, in any one of the foregoing methods, the capture oligonucleotide is affixed to the surface at the 3'-end of the capture oligonucleotide, for example via a 3'-biotin conjugate affixed to a streptavidin derivatized surface or the equivalent thereof. In another embodiment, in any one of the foregoing methods, the capture oligonucleotide is affixed to the surface at the 5'-end of the capture oligonucleotide, for example via a 5'-biotin conjugate affixed to a streptavidin derivatized surface or the equivalent thereof.

In one embodiment, in any one of the foregoing methods, the detection oligonucleotide comprises a detectable moiety at the 3'-end of the detection oligonucleotide, for example wherein the detection oligonucleotide comprises a 3'-FITC moiety or an equivalent detectable moiety or ligand. In another embodiment, the detection oligonucleotide comprises a detectable moiety at the 5'-end of the detection oligonucleotide, for example wherein the detection oligonucleotide comprises a 5'-FITC moiety or an equivalent detectable moiety or ligand. In another embodiment, the detection oligonucleotide comprises a detectable moiety at the 5' and 3'-ends of the detection oligonucleotide, for example wherein the detection oligonucleotide comprises a 5'-FITC moiety and 3'-FITC or an equivalent detectable moiety or ligand.

In one embodiment, in any one of the foregoing methods, a capture oligonucleotide of the invention is affixed to a surface of the invention via a high affinity ligand pair interaction. Non-limiting examples of high affinity ligand pairs include biotin-avidin, biotin-streptavidin, biotin-neutravidin, antibody-ligand, receptor-ligand, antibody-protein, antibody-receptor, antibody-antibody, and/or drug-receptor pairs.

In one embodiment, in any one of the foregoing methods, a reporter molecule of the invention comprises a fluorescent label, chemiluminsecent label, bioluminescent label, peptide, polypeptide, protein, radioisotope, small molecule, antibody or enzyme-linked antibody. Non-limiting examples of enzyme-linked antibodies include alkaline phosphatase-conjugated antibody, horseradish peroxidase-linked antibody, beta-galactosidase-conjugated antibody, and/or a glucose oxidase-conjugated antibody.

In one embodiment, in any of the forgoeing methods, a detergent or other suitable reagents known in the art is used to prevent or disrupt non-specific interactions between the siNA nucleic acid sequence(s) and other components of the sample, such as proteins and other nucleic acid molecules present in the sample. In another embodiment, the detergent or other suitable reagents known in the art is used when assaying the concentration of unhybridized target (e.g., siNA) sequences and when assaying the concentration of dissassociated target (e.g., siNA) sequences. In another embodiment, the detergent or other suitable reagents known in the art is used when assaying the concentration of unhybridized target (e.g., siNA) sequences but not when assaying the concentration of dissassociated target (e.g., siNA) sequences. In another embodiment, the detergent or other suitable reagents known in the art is not used when assaying the concentration of unhybridized (target (e.g., siNA) sequences but is used when assaying the concentration of dissassociated target (e.g., siNA) sequences. Non-limiting examples of detergents that can be used in any of the foregoing methods of the invention include cationic detergents, anionic detergents, non-ionic detergents, and/or zwitterionic detergents, such as sodium dodecyl sulfate (SDS), guanidine isothiocyanate (GITC), triton-X-100 (t-octylphenoxypropylethoxyethanol), tween-20(polyoxyethylene-sorbitan monolaurate, deoxycholic acid, N-lauroyl-sarcosine, dodecyltrimethylammonium bromide, and/or methylbenzenethonium chloride.

In one embodiment, in any one of the foregoing methods, the surface comprises a microtiter plate, a glass bead, plastic bead, polystyrene bead, latex bead or metal bead, metal particle, membrane, filter, nitrocellulose, silicone chip, glass slide, plastic slide, metal slide, metal plate, glass tube, plastic tube, or plastic sheet and/or the equivalent thereof.

In one embodiment, a hybridization assay of the invention comprises steps in which the removal of unbound material (e.g., siNA sequence, detection oligonucleotide, or reporter molecule) is accomplished by washing (e.g. with a buffer), centrifugation, filtration, aspiration, decantation, or adsorption.

In one embodiment, in any one of the foregoing methods, the sample is partitioned into separate samples of differing cell type prior to assaying the concentration of the target (e.g., siNA) nucleic acid. In another embodiment, in any one of the foregoing methods, the sample is partitioned into separate samples of differing tissue type prior to assaying the concentration of target (e.g., siNA) nucleic acid. The partitioning can be quantitative such that the amount of siNA in each sub-sample can be determined by methods described herein. The partitioning of the sample can be accomplished by methods known in the art, such as by size exclusion, differential centrifugation, affinity chromatography, or magnetic particle separation.

In one embodiment, in any one of the foregoing methods, the target (e.g., siNA) sequence is a full length target (e.g., siNA) sequence. In another embodiment, in any one of the foregoing methods, the target (e.g., siNA) sequence is a partial length sequence or metabolite of a full length sequence, such as an N-1, N-2, N-3, N-4, N-5, N-6, N-7, N-8, N-9, N-10, N-11, N-12, N-13, N-14, N-15 or greater N-sequence.

In one embodiment, in any one of the foregoing methods, the assay is a high throughput assay such as a multiwell, multiplate, multisolution or equivalent multiplex assay.

In any one of the foregoing methods, the assay applicable to any sequence of any chemical composition so long as sufficient base pairing interactions are allowed for detection by a hybridization assay or an equivalent assay for the detection of oligonucleotide sequences. Furthermore given the specific properties of any given sequence, or chemical composition thereof, the lengths and chemical compositions of the capture and detections probes can be varied. For example, in one embodiment, if the siNA is primarily 2-O-methyl modified with an AT rich 5'-half, then a longer DNA capture probe may be desired. The DNA can increase the affinity to the 2'-O-methyl sequence and the length can compensate for the weaker interaction of the AT rich sequence. Likewise, helix stabilization of destabilizing chemistries can be integrated into the design of the method. Furthermore, the order of steps may be modified where necessary. For example, excess detection oligo (above the Kd) can be heated and cooled to effect dissociation of the complementary siNA strand prior to addition to the detection assay.

In any one of the foregoing methods, the amount of reporter molecule can be determined spectrophotometrically, spectrofluorometrically, by scintillation counting, gamma counting, phosphorescence, chemiluminescence, bioluminescence, color change, change in surface thickness, precipitation, optical rotation, or any other method as is known in the art (see for example Holtke et al., U.S. Pat. No. 5,354,657 and Ishii et al., U.S. Pat. No. 5,474,895, both incorporated by reference herein in their entirety including the drawings).

In one embodiment, the biological sample comprises a cell, tissue, or fluid sample and/or components thereof. A cell or tissue sample can comprise any cell type or tissue type present in a subject, organism, or biological system. Non-limiting examples of biological fluids include blood, serum, urine, plasma, cerebrospinal fluid (CSF), optic fluid (vitrius), semen, milk, interstitial fluid, saliva, sputum and/or synovial fluid. The sample can include a mixture of cellular and other components, including drug compounds and compositions, excipients, delivery vehicles, and/or assay reagents. The sample can include other drugs, nucleic acid molecules, infectious agents and/or components thereof. The sample can be assayed directly or can be processed, extracted, or purified to varying degrees before being assayed. The sample can be derived from a healthy subject or a subject suffering from a condition, disorder, disease or infection. For example, the subject is a human who has cancer, an inflammatory disease, autoimmune disease, metabolic disease, CNS disease, ocular disease, cardiac disease, pulmonary disease, hepatic disease, gastrointestinal disease, neurodegenerative disease, genetic disease, infectious disease, or viral infection.

In one embodiment, a method of the invention is used to determine the concentration of a target (e.g., siNA) nucleic acid in differing cell types present in a tissue. For example, a method of the invention can be used to distinguish target (e.g., siNA) nucleic acid concentration in hepatocytes, kupffer cells, and endothelial cells all derived from a liver tissue sample. The differing cell types can be separated by methods known in the art, such as size exclusion and fractionation.

In one embodiment, a target (e.g., siNA) nucleic acid of the invention can be unmodified or chemically-modified. The use of chemically-modified siNA can improve various properties of native siNA molecules through increased resistance to nuclease degradation in vivo and/or through improved cellular uptake. The siNA molecules of the instant invention provide useful reagents and methods for a variety of therapeutic, diagnostic, target validation, genomic discovery, genetic engineering, and pharmacogenomic applications.

In another embodiment, a target (e.g., siNA) nucleic acid of the invention can be chemically synthesized, expressed from a vector or enzymatically synthesized.

In one embodiment, the invention features a kit comprising a surface bound capture oligonucleotide that includes a sequence of nucleotides that has substantial complementarity with a first portion of a siNA sequence; a detection oligonucleotide that includes a sequence of oligonucleotide bases that has substantial complementarity with a second portion of a siNA sequence that differes from the first portion and that has a reporter enzyme covalently bound thereto, a substrate for the reporter enzyme, which catalyzes a reation that can be quantified by a detectable response (e.g., chemiluminescence, fluorescence, color change, optical rotation, deposition of a precipitate etc.), and any other reagent or device required to carry out a method of the invention.

Other features and advantages of the invention will be apparent from the following description of the preferred embodiments thereof, and from the claims.

BRIEF DESCRIPTION OF THE DRAWINGS

FIG. 1A shows a non-limiting schematic representation of processes and methods that can be used to detect and quantify oligonucleotide (e.g., double stranded nucleic acid molecules or siNA) molecules in a sample. A tissue, fluid sample, or cells (pooled or differentiated based on cell type) can be assayed directly or can be processed prior to detection/quantitation, for example via extraction, purification, denatureation or any other process that is used to prepare a sample for analysis using the methodologies disclosed herein and those methodologies known in the art. Non-limiting examples of methods that can be used to detect or quantify siNA molecules and other nucleic acid molecules herein include hybridization assays, antibody binding assays, chromatographic assays (e.g., HPLC and/or LC-MS), electrophoretic assays (e.g., CGE and/or CGE-MS), and nucleic acid sensor molecule assays.

FIG. 1B shows a non-limiting example of a schematic representation of a hybridization assay of the invention used to detect the concentration of siNA molecules. A capture oligonucleotide is affixed to a surface, wherein the capture oligonucleotide comprises sequence having complementarity to a first portion of a target oligonucleotide (e.g., siNA) sequence. A detection oligonucleotide comprising a reporter molecule or reporter molecule ligand and having complementarity to a second portion of the target oligonucleotide sequence is used to detect the target oligonucleotide-capture oligonucleotide complex.

FIG. 1C shows a non-limiting example of the princliple of the hybridization assay used to determine the concentration of a siNA duplex in a sample. The detection of siNA involves separate quantification of any unhybridized single stranded sense and unhybridized antisense sequences present in a sample as well as quantification of duplex siNA sequences based on the concentration of sense and antisense strand sequences that result from treatment of the sample under conditions suitable for dissassociation of the sense and antisense strands. The concentration of any unhybridized single stranded sense or antisense oligonucleotide can be subtracted from the total concentration of single stranded sense or antisense oligonucleotide after dissociation of the duplex to arrive at the concentration of the duplex.

FIG. 2 shows a non-limiting example of standard concentration curves of different siNAs in single stranded and duplex form (A) Stab 7 sense strand; (B) Stab 8 antisense strand; (C) Stab 7 Cholesterol conjugate sense strand; and (I)) Stab 7 Cholesterol Trigalactose conjugate sense strand. The known concentrations of the various siNA sequences were prepared and analyzed by hybridization-ELISA method. The intensity of color developed due to the specific concentration of siNA is plotted in the graphs.

FIG. 3 shows a non-limiting example of the detection of quality control samples by hybridization assay for (A) Stab 7 single stranded sequence; (B) Stab 8 single stranded sequence; and (C) Stab 7 duplex sequence. The solutions of standards were prepared and analyzed by hybridization assay as described in Example 1. The QC1 samples were prepared by direct dilution of known concentrations of stocks in 1M GITC buffer and used immediately while QC2 samples were prepared similarly but stored at −700C overnight prior to use. After performing hybridization-ELISa assay, the intensity of color developed as a finction of concentration of siNA is plotted in the graphs.

FIG. 4 shows a non-limiting example of the detection of 5' truncated single stranded (A) Stab 7 and (B) Stab 8 siNA molecules. Potential metabolites having truncated versions of Stab 7 sense strand siNA sequences and Stab 8 antisense sequences were synthesized with N-1, N-2, and N-4 truncations. The known concentrations of the various siNA sequences were prepared and analyzed by hybridization-ELISA method. The intensity of color developed due to the specific concentration of siNA is plotted in the graphs.

FIG. 5 shows a non-limiting example of the effect of hepatocyte lysate on the detection of (A) single stranded Stab 7 cholesterol conjugate siNA sequence, (B) single stranded Stab 8 siNA sequence, and (C) Stab 7 cholesterol conjugate duplex siNA sequence by hybridization assay. In the Figure, A=1E+6 hepatocytes lysate/ml; B=5E+5 hepatocytes lysate/ml; C=: 2.5E+5 hepatocytes lysate/ml; D=1E+5 hepatocytes lysate/ml; E=5E+4 hepatocytes lysate/ml; and F=0.1 mg/ml naive liver homogenate. The known concentrations of the various siNA sequences were prepared in buffer containing varying amounts of hepatocyte lysate and analyzed by hybridization-ELISA method. The intensity of color developed due to the specific concentration of siNA is plotted in the graphs.

FIG. 6 shows a non-limiting example of the effect of monkey plasma on the detection of (A) single stranded Stab 7 cholesterol conjugate siNA sequence, (B) single stranded Stab 8 siNA sequence, and (C) Stab 7 cholesterol conjugate duplex siNA sequence by hybridization assay. The known concentrations of the various siNA sequences were prepared in buffer containing varying amounts of monkey plasma and analyzed by hybridization-ELISA method. The intensity of color developed due to the specific concentration of siNA is plotted in the graphs.

FIG. 7 shows a non-limiting example of the concentration of siNA duplex sequences and siNA antisense sequences in mouse hepatocytes after systemic administration as determined by hybridization assay.

FIG. 8 shows the results of a study in which excess biotinylated antisense strand was used to capture dissociated sense strand of a siNA duplex after heating. The heated duplex (90 degrees C.) was mixed with biotinylated sense sequences at room temperature in a 96 well plate with vigorous pipetting followed by vigorous vortexing for 10 minutes. The plate was then centrifuged and supernatants transferred to a hybridization assay plate. The value of antisense strand duplex concentration with the sense strand removed (duplex, heated, beads) is compared to antisense strand duplex concentration without removal of the sense strand (duplex, heated), intact duplex (duplex, unheated), and antisense strand alone (antisense, heated).

FIG. 9 shows the results of a comparison of standard curves of different siNA chemistries (Stab 7/8 and Stab 9/10,) of the same siNA sequence that were evaluated using the hybridization assay methodology of the invention in which the concentration of dissassociated sense strand was measured following heating of the siNA duplex at 90 degrees C. for 10 minutes. As shown in the figure, both Stab 7/8 and Stab 9/10 siNA duplexes show similar behavior from 1 to 1000 fmoles/ml of sample, illustrating that the assay can efficiently detect siNA sequences having differing chemical modifications applied to the same sequence.

FIG. 11 shows a non-limiting example of degradation of siNA polynucleotide components when a siNA duplex spiked into urine was examined at various time points and their degradation monitored. (A) Overlayed UV 260 nm chromatograms from separate injections of the sense, antisense and duplex oligonucleotides 6 days after spiking into urine. (B) Chromatograms of sense strand at Day 0 and Day 3. Degradation at day 3 is seen as multiple shoulders on the main peak.

FIG. 12 shows a non-limiting example of the electrospray profile components when a siNA duplex spiked into urine was examined at various time points and their degradation monitored. Deconvoluted electrospray mass spectrum from the sense strand at Day 3 (A) and the antisense strand at Day 6 (B) are shown. Scans were averaged over all the peaks observed in the UW chromatogram for a particular time point in order that all of the oligonucleotide species could be observed together. Degradation species are labeled as the parent compound, N, minus a nucleotide. The parent sequence is shown with an arrow indicating the direction that nucleotide loss proceeds. Some of the degradation species include the addition of a phosphate to the nucleotide and are labeled as +/−PO4.

FIG. 15 shows a non-limiting example of a method of dection of a target polynucleotide of interest in which a dissociated siNA duplex (e.g., heated siNA sample) is added to a surface comprising an affixed capture polynucleotide probe having sequence complementarity to the target polynucleotide of interest. The target polynucloetide hybridizes with the capture probe and the surface is washed to remove any non-hybridized material. A detection oligonucleotide probe is then added to the surface of under conditions suitable for the detection oligonucleotide probe to specifically hybridize with any non-hybridized capture oligonucleotide (e.g., any capture oligonucleotide that is not complexed with the target polynucleotide). The surface is then washed to remove any unbound detection oligonucleotide. Depending on the label used, the signal can be measured at this point. Alternately, a reporter molecule is added to to the surface which is subequently washed to remove any unbound or unreacted reporter molecule and the amount of signal is measured. The signal generated from the assay is inversely proportional to the analyte concentration.

DETAILED DESCRIPTION OF THE INVENTION

Figure 10:
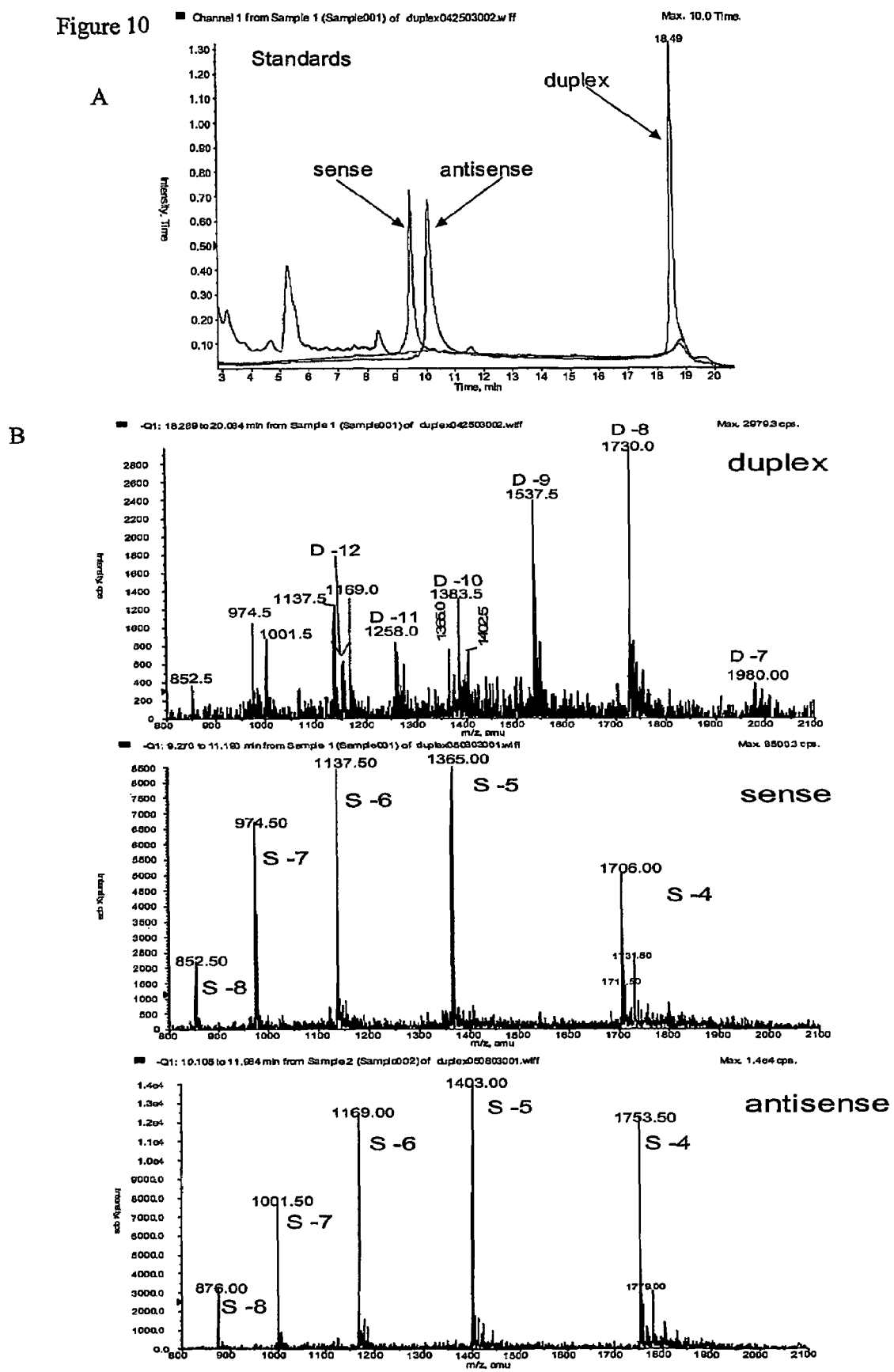
FIG. 10 shows a non-limiting example of the preservation of duplex polynucleotides in the gas phase during electrospray analysis. (A) Overlayed UW 260 nm chromatograms from separate injections of the sense, antisense, and duplex oligonucleotides. 10 uL injections of 2.5 µM (duplex) and 5 µM (single strands). (B) The corresponding electrospray mass spectrum for each of the chromatograms shown in A. Electrospray peaks with their corresponding charge states are labled D for the duplex, AS for the antisense, and A for the sense strand.

Definitions:

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The term "biological system" or "biological sample" as used herein refers to material, in a purified or unpurified form, from biological sources, including but not limited to human, animal, plant, insect, bacterial, viral or other sources. The terms "biological system" or "biological sample" include, for example, a cell, tissue, or organism, or extract thereof. The terms "biological system" or "biological sample" also includes reconstituted RNAi systems that can be used in an in vitro setting. A cell or tissue sample can comprise any cell type or tissue type present in a subject, organism, or biological system. Non-limiting examples of biological fluids include blood, serum, urine, plasma, cerebrospinal fluid (CSF), optic fluid (vitrius), semen, milk, interstitial fluid, saliva, sputum and/or synovial fluid. The sample can include a mixture of cellular and other components, including drug compounds and compositions, excipients, delivery vehicles, and/or assay reagents. The sample can include other drugs, nucleic acid molecules, infectious agents and/or components thereof. The sample can be assayed directly or can be processed, extracted, or purified to varying degrees before being assayed. The sample can be derived from a healthy subject or a subject suffering from a condition, disorder, disease or infection. For example, the subject is a human who has cancer, an inflammatory disease, autoimmune disease, metabolic disease, CNS disease, ocular disease, cardiac disease, pulmonary disease, hepatic disease, gastrointestinal disease, neurodegenerative disease, genetic disease, infectious disease, or viral infection.

The term "detection oligonucleotide" as used herein refers to an oligonucleotide sequence that can be RNA, DNA, and/or analogs or derivatives thereof that comprises a reporter molecule or tag (e.g. FITC), or that is capable of specifically interacting with a reporter molecule, and which is capable of interacting with, hybridizing or forming a stable hybrid with a target nucleic acid sequence or a portion thereof, such as a siNA sequence or a portion thereof. The reporter molecule can be attached to or is capable of interacting with the 5'-end, 3'-end, or both 5' and 3'-ends of the detection oligonucleotide. Alternately, the reporter molecule can be attached to or is capable of interacting with any portion of the detection oligonucleotide sequence. The detection oligonucleotide can be chemically synthesized, enzymatically synthesized, or obtained from a natural source.

The term "capture oligonucleotide" as used herein refers to an oligonucleotide sequence that can be RNA, DNA, and/or analogs thereof that is immobilized on a surface and which is capable of hybridizing or forming a stable hybrid with a target nucleic acid sequence or a portion thereof, such as a siNA sequence or a portion thereof. The capture oligonucleotide can be chemically synthesized, enzymatically synthesized, or obtained from a natural source. The capture oligonucleotide can be immobilized to the surface via a high affinity ligand pair interaction. Non-limiting examples of high affinity ligand pairs include biotin-avidin, biotin-streptavidin, biotin-neutravidin, antibody-ligand, receptor-ligand, antibody-protein, antibody-receptor, antibody-antibody, and/or drug-receptor pairs. The capture oligonucleotide can be affixed to the surface at the 5'-end or 3'-end of the capture oligonucleotide. Non-limiting examples of surfaces that the capture oligonucleotide can be affixed to include microtiter plates, glass beads, plastic beads, polystyrene beads, latex beads or metal beads, metal particles, membranes, filters, nitrocellulose, silicone chips, glass slides, plastic slides, metal slides, metal plates, glass tubes, plastic tubes, or plastic sheets and/or equivalents thereof.

The term "detection reagents" as used herein refers to any reagent, solution, or apparatus that can be used to detect the presence of a nucleic acid molecule, polynucleotide, or oligonucleotide. In one embodiment, the reagents capable of detecting the presence of a nucleic acid molecule in a sample include components of a hybridization-detection assay, such as capture oligonucleotides, detection oligonucleotides, reporter molecules, and any other reagent required for a hybridization-detection assay. In one embodiment, the reagents capable of detecting the presence of a nucleic acid molecule in a sample include the components of an antibody detection assay, such as antibodies, reporter molecules, labels, and any other reagent required for an antibody detection assay. In one embodiment, the reagents capable of detecting the presence of a nucleic acid molecule in a sample include the components of a chromatographic detection assay, such as extraction reagents, reporter molecules, labels, elution buffers, chromatography media detection reagents, and any other reagent required for a chromatographic detection assay. In one embodiment, the reagents capable of detecting the presence of a nucleic acid molecule in a sample include the components of an electrophoretic detection assay, such as extraction reagents, reporter molecules, labels, electrophoretic matrices, and any other reagent required for an electrophoretic detection assay. In one embodiment, the reagents capable of detecting the presence of a nucleic acid molecule in a sample include the components of a nucleic acid sensor molecule detection assay, such as enzymatic nucleic acid molecules, reporter molecules, aptamers, and any other reagent required for a nucleic acid sensor molecule detection assay.

The term "stable hybrid" as used herein refers to an oligonucleotide hybrid that includes a sufficient number of complementary nucleotides to render the resulting hybrids detectable. The formation of stable hybrids is a fumction of the extent of complementarity between the hybridizing nucleic acids and also the sequence of the nucleotides that form the hybrid pairs. One of skill in the art will recognize that the stability of a hybrid is a function of numerous parameters, including the particularly matched and mismatched nucleotides, the length of of the matched and mismatched nucleotides, the composition of differing complementary nucleiotides, and the overall length of the hybrid. One of skill in the art can readily ascertain the minimum number of complementary nucleotides that a sufficient for a particular set of capture, detection, and target oligonucleotides to interact in a hybridization assay.

The term "reporter molecule" as used herein refers to a molecule that is capable of producing a detectable signal either on its own or by interaction with suitable substrate or an additional molecule together which produce a detectable signal or response. The signal or response can be measured by any means known in the art, such as by chemiluminescence, fluorescence, color change, optical rotation, deposition of a precipitate. The reporter molecule can also comprise a reporter enzyme, such as alkaline phosphatase, horseradish peroxidase, beta-galactosidase, and/or a glucose oxidase, and/or a substrate, ligand or antibody having affinity or specificity for the reporter enzyme. Suitable substrates for the reporter enzyme are compounds that are convertable by the reporter enzyme to produce a compound and/or signal that can be quantified.

The term "target nucleic acid" as used herein refers to the portion of the analytical sample that is to be measured or quantified. Target nucleic acids can include, for example, siNA sequences and portions thereof (e.g., siNA molecules including siNA duplexes, siNA sense regions or strands, siNA antisense regions or strands, hairpin siNA, single stranded siNA, enzymatic nucleic acid molecules, antisense, aptamers, and any other nucleic acid molecule to be detected or quantified in a sample. In certain embodiments, the term "target nucleic acid" refers to any nucleic acid sequence whose expression or activity is to be modulated by a nucleic acid molecule of the invention, such as a siNA molecule.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner, see for example Bass, 2001, *Nature,* 411, 428-429; Elbashir et al., 2001, *Nature,* 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846;

Mello and Fire, International PCT Publication No. WO 01/29058; Deschamps-Depaillette, International PCT Publication No. WO 99/07409; and Li et al., International PCT Publication No. WO 00/44914; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237; Hutvagner and Zamore, 2002, *Science,* 297, 2056-60; McManus et al., 2002, *RNA,* 8, 842-850; Reinhart et al., 2002, *Gene & Dev.,* 16, 1616-1626; and Reinhart & Bartel, 2002, *Science,* 297, 1831). Non limiting examples of siNA molecules of the invention are shown in co-pending U.S. Ser. No. 10/444,853 and PCT/US04/16390, both incorporated by reference herein in their entirety including the drawings. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell.,* 110, 563-574 and Schwarz et al., 2002, *Molecular Cell,* 10, 537-568), or 5',3'-diphosphate. In certain embodiment, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic intercations, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin siNA molecule of the invention can comprise an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. The asymmetric hairpin siNA molecule can also comprise a 5'-terrminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex siNA molecule of the invention can comprise an antisense region having length sufficient to mediate RNAi in a cell or in vitro system (e.g. about 19 to about 22 nucleotides) and a sense region having about 3 to about 18 nucleotides that are complementary to the antisense region.

By "gene" or "target gene" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts.

By "highly conserved sequence region" is meant, a nucleotide sequence of one or more regions in a target gene does not vary significantly from one generation to the other or from one biological system to the other.

By "sense region" or "sense strand" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" or "antisense strand" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity, hybridization, or the formation of a stable hybrid or complex. Determination of binding free energies for nucleic acid molecules is well known in the art (see, e.g., Turner et al., 1987, *CSH Symp. Quant. Biol.* LII pp. 123-133; Frier et al., 1986, *Proc. Nat. Acad. Sci. USA* 83:9373-9377; Turner et al., 1987, *J. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

In one embodiment of the present invention, each sequence of a siNA molecule of the invention is independently about 18 to about 24 nucleotides in length, in specific embodiments about 18, 19, 20, 21, 22, 23, or 24 nucleotides in length. In another embodiment, the siNA duplexes of the invention independently comprise about 17 to about 23 base pairs (e.g., about 17, 18, 19, 20, 21, 22 or 23). In yet another embodiment, siNA molecules of the invention comprising hairpin or circular structures are about 35 to about 55 (e.g., about 35, 40, 45, 50 or 55) nucleotides in length, or about 38 to about 44 (e.g. 38, 39, 40, 41, 42, 43 or 44) nucleotides in length and comprising about 16 to about 22 (e.g., about 16, 17, 18, 19, 20, 21 or 22) base pairs.

The term "kit" as used herein refers to any combination of reagents or apparatus that can be used to perform a method of the invention. The kit of the invention can further include any additional reagents, reporter molecules, buffers, excipients, containers and/or devices as required described herein or known in the art, to practice a method of the invention.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells. A subject can be a patient suffering from a condition, disorder, disease or infection. For example, the subject is a human who has cancer, an inflammatory disease, autoimmune disease, metabolic disease, CNS disease, ocular disease, cardiac disease, pulmonary disease, hepatic disease, gastrointestinal disease, neurodegenerative disease, genetic disease, infectious disease, or viral infection.

The term "phosphorothioate" as used herein refers to an internucleotide linkage having Formula I, wherein Z and/or W comprise a sulfur atom. Hence, the term phosphorothioate refers to both phosphorothioate and phosphorodithioate internucleotide linkages.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

The term "acyclic nucleotide" as used herein refers to any nucleotide having an acyclic ribose sugar, for example where any of the ribose carbons (C1, C2, C3, C4, or C5), are independently or in combination absent from the nucleotide.

Hybridization Assays

A representative hybridization assay format is shown in FIG. 1B. Generally, the assay comprises a capture oligonucleotide that is affixed to a surface via a high affinity ligand pair interaction, such as a biotin-avidin, biotin-streptavidin, or biotin-neutravidin binding system or alternately via a covalent linkage, and a detection oligonculeotide that comprises a reporter molecule or ligand that is capable of interacting with a reporter molecule allowing for the quantitiation of signal corresponding to the concentration of target oligonucleotide in a biological system or sample. The surface can comprise microtiter plate, a glass bead, plastic bead, polystyrene bead, latex bead or metal bead, metal particle, membrane, filter, nitrocellulose, silicone chip, glass slide, plastic slide, metal slide, metal plate, glass tube, plastic tube, or plastic sheet and/or the equivalent thereof. The capture and detection oligonucleotides are of sufficient length to stably interact with differing portions of any target oligonucleotide sequence present in the system or sample. The capture and detection oligonucleotides can be chemically modified to alter the hybridization properties with the target oligonucleotide sequence, for example by altering the length of the capture oligonucleotide sequence or by including modified nucleotides such as locked nucleic acid (LNA), peptide nucleic acid (PNA), 2'-deoxy-2'-fluoro, 2'-O-methyl nucleotides, 2,6-diaminopurine, or any other nucleotide or non-nucleotide that increases the affinity of the capture and detection oligonucleotides with a portion of the target oligonucleotide sequence. The high affinity ligand for attachement to the surface can be attached to the 5'-end or 3'-end of the capture oligonucleotide. The reporter molecule or ligand for interaction with a reporter molecule can be at the 5'-end, 3'-end, or both 5' and 3'-ends of the detection oligonucleotide. A reporter molecule of the invention can comprise a fluorescent label, chemilurninsecent label, bioluminescent label, peptide, polypeptide, protein, radioisotope, small molecule, antibody or enzyme-linked antibody. Non-limiting examples of enzyme-inked antibodies include alkaline phosphatase-conjugated antibody, horseradish peroxidase-linked antibody, beta-galactosidase-conjugated antibody, and/or a glucose oxidase-conjugated antibody.

The above description is non-limiting in that all that is required is that the hybridization assay be capable of quantifying the concentration of a given nucleic acid (e.g., siNA) target oligonucleotide sequence in a system or sample, be it an unhybridized target oligonucleotide sequence present in the system or sample or a target oligonucleotide sequence present in the system or sample as a duplex that is dissassociated into one or more single stranded sequences by conditions of the assay, such as heating. Non-limiting examples of hybridization assays that can be used in the instant applicaton include those described in Holtke et al., U.S. Pat. No. 5,354,657; Ishii et al., U.S. Pat. No. 5,474,895; Mirkin et al., U.S. Pat. No. 6,506,564; Stimpson et al., U.S. Pat. No. 5,599,668; and Livak et al., U.S. Pat. No. 6,030,787, all incorporated by reference herein in their entirety including the drawings.

The present invention allows for the detection and quantitation of the target (e.g., siNA) nucleic acid duplex and single stranded sequences such as sense strand sequences and antisense strand sequences by distinguishing between those sequences that are unhybridized and hybridized in the system or sample (see for example FIG. 1C). Unhybridized and hybridized sequences are distinguished by a processing step that dissassociates the hybridized sequences in the system or sample, allowing for an assay to determine the concentration of an entire set of sequences, such as all antisense or all sense sequences present in the sample. A separate assay is used to determine the concentration of only unhybridized sequences present in a system or sample, i.e. in which all siNA duplex or hairpin siNA species remain in double stranded form. The concentration of the unhybridized target sequence is subtracted from the total concentration of the target sequence from the processed assay to arrive at the concentration of double stranded siNA present in the sample.

Antibody Assays

Antibodies are highly specific and efficient analytical tools that can be used in biomedical research. Modem researchers have capitalized on this bioanalytical tool through a variety of modification techniques, including antibody engineering using recombinant DNA methods. The use of antibodies has expanded from simple diagnostic assays to the detection of molecular structures, the elucidation of gene finction, the localization of gene products, and the rapid screening of biological effectors for drug discovery and testing. The use of such antibodies with fluorescent or enzymatic tags, in concert with advances in microscopy, has resulted in improved enzyme-linked immunosorbent assay (ELISA) systems. The use of ELISA based microarrays with antibodies promises to transform current paradigms of disease research and the search for new therapeutic compounds. Moreover, antibodies can also serve not only as powerful research tools, but also as therapeutic compounds when conjugated with modifications such as radioisotopes and/or other chemotherapeutic compounds.

In recent years antibodies have become well characterized through experimentation and manipulation. The typical antibody is a tetrameric molecule comprising two copies of a heavy chain (H) polypeptide which is approximately 440 amino acids long and two copies of a light-chain (L) polypeptide which is about 220 amino acids long. Each antibody-based H and L polypeptide contains a variable region and a constant region. At the terminus of each arm of the Y-shaped antibody exists a site comprising the variable termini of the H and L subunits, which together bind to a specific and unique site on an antigen, otherwise known as an epitope. Antibody technology has developed from the production and use of polyclonal antibody mixtures derived from rabbits and horses to the production of specific monoclonal antibodies through cell fusion techniques using mice spleens and cancers, to modern engineering of uniquely designed mono and divalent antibodies. Chimeric antibodies are created when the antigen-binding component of a one antibody, such as a mouse antibody, is fused to the effector component of another antibody, for example a human antibody, using genetic engineering. Monoclonal antibodies originally raised in mice, rabbits, pigs, sheep, cows, horses or the like can also be "humanized" by exchanging surface-exposed amino acids, which can be determined through molecular biological (e.g., sequencing), crystallographic and molecular modeling techniques, found on the non-human antibody to those more often found in human antibodies. Also, mice have been developed that harbor human antibody-producing elements and major histocompatibility complexes (MHCs) in place of the corresponding murine elements and complexes, such that immunization of these mice leads to the direct generation of human antibodies in the mouse. Antibodies can also be fused with a variety of other proteins that can modulate both antibody activity and localization for specific applications.

As such, antibodies can be designed to have specificity for oligonucleotides (e.g., siNA) present in a sample. The antibodies of the invention can be designed or selected to discriminate between duplex and single stranded nucleic acid molecules present in a sample (see for example FIG. 1C) or between nucleic acid molecules having particular sequence compositions or having particular nucleotides, such as modified nucleotides. Non-limiting examples of qauntitative antibody based detection assays that can be used in conduction with the methods of the instant invention are described in Radka et al., U.S. Ser. No. 10/366,191, incorporated by reference herein.

Chromatoraihic Assays

The use of chromatography, such as high performance liquid chromatography (HPLC) in the detection and quantitation of nucleic acid molecules is well recognized in the art (see for example Gilar, 2001, *Analytical Biochemistry*, 298, 196 and Apffel et al., 1997, *Journal of Chromatography*, 777, 3). Chromatographic methods of the present invention can be used to detect single stranded nucleic acid molecules and duplex nucleic acid molecules in the same analytical method or in separate analytical methods that can combine different chromatographic approaches, such as reverse phase, ion exchange, ion-pairing, and/or size exclusion chromatography. Chromatographic analysis can be coupled with mass spectrometry methods to analyse sequence identity, base composition, modifications, and metabolites of nculeic acid molecules present in a sample, such as a biological sample.

The nucleic acid sample to be analyzed is generally injected and pre-mixed with a mobile phase prior to elution on a solid support. The sample can be injected into a pre-conditioned mobile phase, or can also be passed through a preconditioning tubing or pre-column placed between injector and column. This allows the sample to equilibrate before contact with the solid support, and provides a means for denaturation of the sample, e.g., by heating of the mobile phase-sample mixture or by contact of the sample with the alkaline environment of the mobile phase. The stationary phase used in the present methods can be any reverse phase or ion-exchange solid support, including monolith stationary phases and stationary phases based on particles. Reverse phase and ion exchange columns or column packing materials for use in the invention are typically composed of alkylated polymeric solid support materials such as silica, cellulose and cellulose derivatives such as carboxymethylcellulose, alumina, zirconia, polystyrene, polyacrylamide, polymethylmethacrylate, and/or styrene copolymers. In one embodiment, the polymeric base material is a styrene-divinyl copolymer. Typically, the stationary support is composed of beads from about 1-100 microns in size.

The mobile phase can contain an ion-pairing agent and an organic solvent. Ion-pairing agents for use in the methods herein include lower primary, secondary and tertiary amines, lower trialkylammonium salts such as triethylammonium acetate and lower quaternary ammonium salts. A non-limiting example of a tertiary amine is triethyl amine. Typically, the ion-pairing reagent is present at a concentration between about 0.05 and 1.0 molar. Organic solvents for use in the method include solvents such as methanol, ethanol, 2-propanol, acetonitrile, and/or ethyl acetate.

In one embodiment, the method of the invention utilizes thermal means to provide and maintain completely denaturing conditions of the mobile phase and the stationary phase during HPLC analysis. When denaturation of the sample is provided by heating, preferably the apparatus used in performing the HPLC, e.g., the sample loop, preconditioning coil, and the column, are all maintained at a sufficient temperature to maintain denaturation of the nucleic acid in the sample. In another embodiment of the invention, completely denaturing conditions are achieved and maintained by the presence of a compound that increases the pH of the mobile phase, e.g. NaOH. Sample elution is then carried out under pH conditions effective to maintain complete denaturation of the nucleic acids. In such cases, a lower column temperature (less than about 65.degree. C.) can be sufficient for determining polymorphisms in the sample.

In another embodiment of the present invention analysis of the nucleotide sequence of an oligomer is determined by applying a sample containing an oligomer to a C-18 alkylated polystyrene-divinylbenzene copolymer stationary support and eluting the mixture with a mobile phase containing triethylammonium acetate as the ion-pairing reagent and acetonitrile as the organic solvent at a temperature between about 70 and 80 degrees C.

The present invention allows for the detection and quantitation of the target (e.g., siNA) nucleic acid duplex and single stranded sequences such as sense strand sequences and antisense strand sequences by distinguishing between those sequences that are unhybridized and hybridized in the system or sample (see for example FIG. 1C). In addition, a chromatographic assay of the invention can be used without denaturing conditions such that nucleic acid duplex molecules can be distinguished from single stranded species within the same analytical method. As such, the concentration of duplex and/or single stranded species in a sample can be ascertained.

Electrophoretic Assays

The use of electrophoresis, such as capillary gel electrophoresis (CGE) in the detection and quantitation of nucleic acid molecules is well recognized in the art (see for example Von Brocke et al., *Journal of Chromatography*, 991, 129 and Dedionisio et al., 2001, *Methods in Molecular Biology*, 162, 353). Electrophoretic methods of the present invention can be used to detect single stranded nucleic acid molecules and duplex nucleic acid molecules in the same analytical method. Electrophoretic analysis can be coupled with mass spectrometry methods to analyse sequence identity, base composition, modifications, and metabolites of nculeic acid molecules present in a sample, such as a biological sample.

The methods of the invention can be practiced using commercially available electrophoretic apparatus, produced for example by LKB (Bromma, Sweden) and Beckman Instruments (Fullerton, Calif.). The methods of the invention also can be practiced using a wide variety of commercially available capillary electrophoresis columns and buffers.

The present invention allows for the detection and quantitation of the target (e.g., siNA) nucleic acid duplex and single stranded sequences such as sense strand sequences and antisense strand sequences by distinguishing between those sequences that are unhybridized and hybridized in the system or sample (see for example FIG. 1C). In addition, an electrophoretic assay of the invention can be used without denaturing conditions such that nucleic acid duplex molecules can be distinguished from single stranded species within the same analytical method. As such, the concentration of duplex and/or single stranded species in a sample can be ascertained.

Nucleic Acid Sensor Molecule Assays

Nucleic acid sensor molecules can be used to detect the presence of and quantify nucleic acid molecules (e.g., oligonucleotides including siNA molecules) in a sample. Non-limiting examples of nucleic acid sensor molecules are described in Usman et al., International PCT Publication No. WO 01/66721, Seiwert et al., International PCT Application No. PCT/US02/35529, and Seiwert et al., U.S. Ser. No. 10/422,050, incorporated by reference herein. The nucleic acid sensor molecule can be designed or selected to discriminate between duplex and single stranded nucleic acid molecules present in a sample (see for example FIG. 1C) or between nucleic acid molecules having particular sequence compositions or having particular nucleotides, such as modified nucleotides. Dectection methods using nucleic acid sensor molecules are described in Usman et al., International PCT Publication No. WO 01/66721, Seiwert et al., International PCT Application No. PCT/US02/35529, and Seiwert et al., U.S. Ser. No. 10/422,050 and can similarly be applied to the methods of the instant invention to detect and quantify oligonucleotides (e.g., siNA) present in a sample.

Mechanism of Action of Nucleic Acid Molecules of the Invention

RNA Interference

RNA interference refers to the process of sequence specific post-transcriptional gene silencing in animals mediated by short interfering RNAs (siRNAs) (Fire et al., 1998, *Nature*, 391, 806). The corresponding process in plants is commonly referred to as post-transcriptional gene silencing or RNA silencing and is also referred to as quelling in fingi. The process of post-transcriptional gene silencing is thought to be an evolutionarily-conserved cellular defense mechanism used to prevent the expression of foreign genes which is commonly shared by diverse flora and phyla (Fire et al., 1999, *Trends Genet.*, 15, 358). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as Dicer. Dicer is involved in the processing of the dsRNA into short pieces of dsRNA known as short interfering RNAs (siRNAs) (Berstein et al., 2001, *Nature*, 409, 363). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control (Hutvagner et al, 2001, *Science*, 293, 834). The RNAi response also features an endonuclease complex containing a siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, *Genes Dev.*, 15, 188). In addition, RNA interference can also involve small RNA (e.g., micro-RNA or miRNA) mediated gene silencing, presumably though cellular mechanisms that regulate chromatin structure and thereby prevent transcription of target gene sequences (see for example Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237). As such, siNA molecules of the invention can be used to mediate gene silencing via interaction with RNA transcripts or alternately by interaction with particular gene sequences, wherein such interaction results in gene silencing either at the transcriptional level or post-transcriptional level.

RNAi has been studied in a variety of systems. Fire et al., 1998, *Nature*, 391, 806, were the first to observe RNAi in *C. elegans*. Wianny and Goetz, 1999, *Nature Cell Biol.*, 2, 70, describe RNAi mediated by dsRNA in mouse embryos. Hammond et al., 2000, *Nature*, 404, 293, describe RNAi in *Drosophila* cells transfected with dsRNA. Elbashir et al., 2001, *Nature*, 411, 494, describe RNAi induced by introduction of duplexes of synthetic 21-nucleotide RNAs in cultured mammalian cells including human embryonic kidney and HeLa cells. Recent work in Drosophila embryonic lysates has revealed certain requirements for siRNA length, structure, chemical composition, and sequence that are essential to mediate efficient RNAi activity. These studies have shown that 21 nucleotide siRNA duplexes are most active when containing two 2-nucleotide 3'-terminal nucleotide overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, *EMBO J.*, 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, *Cell*, 107, 309); however, siRNA molecules lacking a 5'-phosphate are active when introduced exogenously, suggesting that 5'-phosphorylation of siRNA constructs may occur in vivo.

Decoys

Nucleic acid decoy molecules are mimetics of naturally occurring nucleic acid molecules or portions of naturally occurring nucleic acid molecules that can be used to modulate the function of a specific protein or a nucleic acid whose activity is dependant on interaction with the naturally occurring nucleic acid molecule. Decoys modulate the function of a target protein or nucleic acid by competing with authentic nucleic acid binding to the ligand of interest. Often, the nucleic acid decoy is a truncated version of a nucleic acid sequence that is recognized, for example by a particular protein, such as a transcription factor or polymerase. Decoys can be chemically modified to increase binding affinity to the target ligand as well as to increase the enzymatic and chemical stability of the decoy. In addition, bridging and non-bridging linkers can be introduced into the decoy sequence to provide additional binding affinity to the target ligand. Nucleic acid decoys can be single stranded or double stranded.

Aptamers

Nucleic acid aptamers can be selected to specifically bind to a particular ligand of interest (see for example Gold et al., U.S. Pat. No. 5,567,588 and U.S. Pat. No. 5,475,096, Gold et al., 1995, *Anntu. Rev. Biocheni.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628). For example, the use of in vitro selection can be applied to evolve nucleic acid aptamers with binding specificity for a given target molecule, such as a receptor, ligand, or polymerase. Aptamers can be chemically modified to increase binding affinity to the target ligand as well as to increase the enzymatic and chemical stability of the aptamer. In addition, bridging and non-bridging linkers can be introduced into the aptamer sequence to provide additional binding affinity to the target ligand. Nucleic acid aptamers can be single stranded or double stranded.

Antisense

Antisense molecules may be modified or unmodified RNA, DNA, or mixed polymer oligonucleotides and primarily function by specifically binding to matching sequences resulting in modulation of peptide synthesis (Wu-Pong, November 1994, *BioPharm*, 20-33). The antisense oligonucleotide binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, *Crit. Rev. in Oncogenesis* 7, 151-190).

In addition, binding of single stranded DNA to RNA may result in nuclease degradation of the heteroduplex (Wu-Pong, supra; Crooke, supra). To date, the only backbone modified DNA chemistry which will act as substrates for RNase H are phosphorothioates, phosphorodithioates, and borontrifluoridates. Recently, it has been reported that 2'-arabino and 2'-fluoro arabino-containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526; Thompson et al., U.S. Ser. No. 60/082,404 which was filed on Apr. 20, 1998; Hartmann et al., U.S. Ser. No. 60/101,174 which was filed on Sep. 21, 1998) all of these are incorporated by reference herein in their entirety.

Antisense DNA can be used to target RNA by means of DNA-RNA interactions, thereby activating RNase H, which digests the target RNA in the duplex. Antisense DNA can be chemically synthesized or can be expressed via the use of a single stranded DNA intracellular expression vector or the equivalent thereof.

Triplex Forming Oligonucleotides (TFO)

Single stranded oligonucleotide can be designed to bind to genomic DNA in a sequence specific manner. TFOs can be comprised of pyrimidine-rich oligonucleotides which bind DNA helices through Hoogsteen Base-pairing (Wu-Pong, supra). In addition, TFOs can be chemically modified to increase binding affinity to target DNA sequences. The resulting triple helix composed of the DNA sense, DNA antisense, and TFO disrupts RNA synthesis by RNA polymerase. The TFO mechanism can result in gene expression or cell death since binding may be irreversible (Mukhopadhyay & Roth, supra)

2'-5' Oligoadenylates

The 2-5A system is an interferon-mediated mechanism for RNA degradation found in higher vertebrates (Mitra et al., 1996, *Proc Nat Acad Sci USA* 93, 6780-6785). Two types of enzymes, 2-5A synthetase and RNase L, are required for RNA cleavage. The 2-5A synthetases require double stranded RNA to form 2'-5' oligoadenylates (2-5A). 2-5A then acts as an allosteric effector for utilizing RNase L, which has the ability to cleave single stranded RNA. The ability to form 2-5A structures with double stranded RNA makes this system particularly useful for modulation of viral replication.

(2'-5') oligoadenylate structures can be covalently linked to antisense molecules to form chimeric oligonucleotides capable of RNA cleavage (Torrence, supra). These molecules putatively bind and activate a 2-5A-dependent RNase, the oligonucleotide/enzyme complex then binds to a target RNA molecule which can then be cleaved by the RNase enzyme. The covalent attachment of 2'-5' oligoadenylate structures is not limited to antisense applications, and can be further elaborated to include attachment to nucleic acid molecules of the instant invention.

Enzymatic Nucleic Acids

Several varieties of naturally occurring enzymatic RNAs are presently known (Doherty and Doudna, 2001, *Annu. Rev. Biophys. Biomol. Struct.*, 30, 457-475; Symons, 1994, *Curr. Opin. Struct. Biol.*, 4, 322-30). In addition, several in vitro selection (evolution) strategies (Orgel, 1979, *Proc. R. Soc. London*, B 205, 435) have been used to evolve new nucleic acid catalysts capable of catalyzing cleavage and ligation of phosphodiester linkages (Joyce, 1989, *Gene*, 82, 83-87; Beaudry et al., 1992, *Science* 257, 635-641; Joyce, 1992, *Scientific American* 267, 90-97; Breaker et al., 1994, *TIBTECH* 12, 268; Bartel et al., 1993, *Science* 261:1411-1418; Szostak, 1993, *TIBS* 17, 89-93; Kumar et al., 1995, *FASEB J.*, 9, 1183; Breaker, 1996, *Curr. Op. Biotech.*, 7, 442; Santoro et al., 1997, *Proc. Natl. Acad. Sci.*, 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495). Each can catalyze a series of reactions including the hydrolysis of phosphodiester bonds in trans (and thus can cleave other RNA molecules) under physiological conditions.

The enzymatic nature of an enzymatic nucleic acid has significant advantages, such as the concentration of nucleic acid necessary to affect a therapeutic treatment is low. This advantage reflects the ability of the enzymatic nucleic acid molecule to act enzymatically. Thus, a single enzymatic nucleic acid molecule is able to cleave many molecules of target RNA. In addition, the enzymatic nucleic acid molecule is a highly specific modulator, with the specificity of modulation depending not only on the base-pairing mechanism of binding to the target RNA, but also on the mechanism of target RNA cleavage. Single mismatches, or base-substitutions, near the site of cleavage can be chosen to completely eliminate catalytic activity of an enzymatic nucleic acid molecule.

Nucleic acid molecules having an endonuclease enzymatic activity are able to repeatedly cleave other separate RNA molecules in a nucleotide base sequence-specific manner. With proper design and construction, such enzymatic nucleic acid molecules can be targeted to any RNA transcript, and efficient cleavage achieved in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, *Einstein Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371, 1989; Chartrand et al., 1995, *Nucleic Acids Research* 23, 4092; Santoro et al., 1997, *PNAS* 94, 4262).

Because of their sequence specificity, trans-cleaving enzymatic nucleic acid molecules show promise as therapeutic agents for human disease (Usman & McSwiggen, 1995 *Ann. Rep. Med. Chem.* 30, 285-294; Christoffersen and Marr, 1995 *J. Med. Cheyn.* 38, 2023-2037). Enzymatic nucleic acid molecule can be designed to cleave specific RNA targets within the background of cellular RNA. Such a cleavage event renders the RNA non-functional and abrogates protein expression from that RNA. In this manner, synthesis of a protein associated with a disease state can be selectively modulated (Warashina et al., 1999, *Chemistry and Biology*, 6, 237-250.

Synthesis of Nucleic acid Molecules

The oligonucleotides of the invention (e.g., capture oligonucleotides, detection oligonucleotides, and target oligonucleotides) can be synthsized as is known in the art and as described herein. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al, 1992, *Methods in Enzzymology* 211, 3-19, Thompson et al., International PCT Publication No. WO 99/54459, Wincott et al., 1995, *Nucleic Acids Res.* 23, 2677-2684, Wincoft et al., 1997, *Methods Mol. Bio.*, 74, 59, Brennan et al, 1998, *Biotechnol Bioeng.*, 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 2.5 min coupling step for 2'-O-methylated nucleotides and a 45 second coupling step for 2'-deoxy nucleotides or 2'-deoxy-2'-fluoro nucleotides. Table II outlines the amounts and the contact times of the reagents used in the synthesis cycle. Alternatively, syntheses at the 0.2 µmol scale can be performed on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 105-fold excess of S-ethyl tetrazole (60 µL of 0.25 M=15 µmol) can be used in each coupling cycle of 2'-O-methyl residues relative to polymer-bound 5'-hydroxyl. A 22-fold excess (40 µL of 0.11 M=4.4 µmol) of deoxy phosphoramidite and a 70-fold excess of S-ethyl tetrazole (40 µL of 0.25 M=10 µmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in TBF (ABI); and oxidation solution is 16.9 mM I$_2$, 49 mM pyridine, 9% water in TBF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA including certain siNA molecules of the invention and RNA-based capture oligonucleotides and detection oligonucleotides of the invention, follows the procedure as described in Usman et al., 1987, *J. Am. Chem. Soc.*, 109, 7845; Scaringe et al., 1990, *Nucleic Acids Res.*, 18, 5433; and Wincott et al., 1995, *Nucleic Acids Res.* 23, 2677-2684 Wincott et at, 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 7.5 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 µmol scale can be done on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 75-fold excess of S-ethyl tetrazole (60 µL of 0.25 M=15 µmol) can be used in each coupling cycle of 2'-O-methyl residues relative to polymer-bound 5'-hydroxyl. A 66-fold excess (120 µL of 0.11 M=13.2 µmol) of alkylsilyl (ribo) protected phosphoramidite and a 150-fold excess of S-ethyl tetrazole (120 µL of 0.25 M=30 µmol) can be used in each coupling cycle of ribo residues relative to polymer-bound 5'-hydroxyl. Average coupling yields on the 394 Applied Biosystems, Inc. synthesizer, determined by calorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM I$_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supematant is then added to the first supernatant. The combined supernatants, containing the oligoribonucleotide, are dried to a white powder. The base deprotected oligoribonucleotide is resuspended in anhydrous TEA/HF/NMP solution (300 µL of a solution of 1.5 mL N-methylpyrrolidinone, 750 µL TEA and 1 mL TEA•3HF to provide a 1.4 M HF concentration) and heated to 65° C. After 1.5 h, the oligomer is quenched with 1.5 M NH₄HCO₃.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 minutes. The vial is brought to room temperature TEA•3HF (0.1 mL) is added and the vial is heated at 65° C. for 15 minutes. The sample is cooled at −20° C. and then quenched with 1.5 M NH₄HCO₃.

For purification of the trityl-on oligomers, the quenched NH₄HCO₃ solution is loaded onto a C-18 containing cartridge that had been prewashed with acetonitrile followed by 50 mM TEAA. After washing the loaded cartridge with water, the RNA is detritylated with 0.5% TFA for 13 minutes. The cartridge is then washed again with water, salt exchanged with 1 M NaCl and washed with water again. The oligonucleotide is then eluted with 30% acetonitrile.

The average stepwise coupling yields are typically >98% (Wincott et al., 1995 *Nucleic Acids Res.* 23, 2677-2684). Those of ordinary skill in the art will recognize that the scale of synthesis can be adapted to be larger or smaller than the example described above including but not limited to 96-well format.

Alternatively, the nucleic acid molecules of the present invention can be synthesized separately and joined together post-synthetically, for example, by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204), or by hybridization following synthesis and/or deprotection.

The siNA molecules of the invention can also be synthesized via a tandem synthesis methodology as described in, for example McSwiggen et al., U.S. Ser. No. 10/444,853 incorporated by reference herein, wherein both siNA strands are synthesized as a single contiguous oligonucleotide fragment or strand separated by a cleavable linker which is subsequently cleaved to provide separate siNA fragments or strands that hybridize and permit purification of the siNA duplex. The linker can be a polynucleotide linker or a non-nucleotide linker. The tandem synthesis of siNA can be readily adapted to both multiwell/multiplate synthesis platforms such as 96 well or similarly larger multi-well platforms. The tandem synthesis of siNA can also be readily adapted to large scale synthesis platforms employing batch reactors, synthesis columns and the like.

A nucleic acid molecule (e.g., siNA) can also be assembled from two distinct nucleic acid strands or fragments wherein one fragment includes the sense region and the second fragment includes the antisense region of the RNA molecule.

The nucleic acid molecules of the present invention can be modified extensively to enhance stability and/or binding efficiency by modification with, for example, 2'-amino, 2'-C-allyl, 2'-fluoro, 2'-O-methyl, 2'-H (for a review see Usman and Cedergren, 1992, *TIBS* 17, 34; Usman et al., 1994, *Nucleic Acids Symp. Ser.* 31, 163). Oligonucleotides of the invention can be purified by gel electrophoresis using general methods or can be purified by high pressure liquid chromatography (HPLC; see Wincott et al., supra, the totality of which is hereby incorporated herein by reference) and re-suspended in water.

Optimizing Activity of the Nucleic Acid Molecule of the Invention.

The capture oligonucleotides and detection oligonucleotides of the invention can be modified for increased nuclease resistance and/or hybridization efficacy (see for example Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein). All of the above references describe various chemical modifications that can be made to the base, phosphate and/or sugar moieties of the nucleic acid molecules described herein. Such modifications can be useful in preventing degradation of oligonucleotide components of the hybridization assay (e.g., capture and detection oligonucleotidies) when exposed to biological systems and samples and in modulating the binding properties of these oligonucleotide components of the assay (e.g., increasing Tm values between the capture and detections oligonucleotides with the target oligonucleotides).

There are several examples in the art describing sugar, base and phosphate modifications that can be introduced into nucleic acid molecules with significant enhancement in their nuclease stability and efficacy. For example, oligonucleotides are modified to enhance stability and/or enhance activity by modification with nuclease resistant groups, for example, LNA, 2'-amino, 2'-C-allyl, 2'-fluoro, 2'-O-methyl, 2'-O-allyl, 2'-H, nucleotide base modifications (for a review see Usman and Cedergren, 1992, *TIBS*. 17, 34; Usman et al., 1994, *Nucleic Acids Symp. Ser.* 31, 163; Burgin et al., 1996, *Biochemistry*, 35, 14090). Sugar modification of nucleic acid molecules have been extensively described in the art (see Eckstein et al., International Publication PCT No. WO 92/07065; Perrault et al. *Nature*, 1990, 344, 565-568; Pieken et al. *Science*, 1991, 253, 314-317; Usman and Cedergren, *Trends in Biochem. Sci.*, 1992, 17, 334-339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al, U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Eamshaw and Gait, 1998, *Biopolymers (Nucleic Acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010; all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siNA nucleic acid molecules of the instant invention so long as the ability of siNA to promote RNAi is cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

Nucleic acid molecules having chemical modifications that maintain or enhance activity are provided. Such a nucleic acid is also generally more resistant to nucleases than an unmodified nucleic acid Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., 1995, *Nucleic Acids Res.* 23, 2677; Caruthers et al., 1992, *Methods in Enzymology* 211,3-19 (incorporated by reference herein)) have expanded the ability to modify nucleic acid molecules by introducing nucleotide modifications to enhance their nuclease stability, as described above.

In one embodiment, nucleic acid molecules of the invention include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example Lin and Matteucci, 1998, *J. Am. Chem. Soc.*, 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acid molecules of the invention results in both enhanced affinity and specificity to nucleic acid targets, complementary sequences, or template strands. In another embodiment, nucleic acid molecules of the invention include one or more (e.g., about 1, 2, 3, 4, 5, 6, 7, 8, 9, 10, or more) LNA "locked nucleic acid" nucleotides such as a 2',4'-C methylene bicyclo nucleotide (see for example Wengel et al., International PCT Publication No. WO 00/66604 and WO 99/14226).

In another aspect a nucleic acid molecule of the invention (e.g., capture oligonucleitide, detection oligonucleotide, or target oligonucleotide) comprises one or more 5' and/or a 3'-cap structure.

By "cap structure" is meant chemical modifications, which have been incorporated at either terminus of the oligonucleotide (see, for example, Adamic et al., U.S. Pat. No. 5,998,203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, of the 5'-cap includes, but are not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examplesof the 3'-cap includes, but are not limited to, glyceryl, inverted deoxy abasic residue (moiety), 4', 5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

An "alkyl" group refers to a saturated aliphatic hydrocarbon, including straight-chain, branched-chain, and cyclic alkyl groups. Preferably, the alkyl group has 1 to 12 carbons. More preferably, it is a lower alkyl of from 1 to 7 carbons, more preferably 1 to 4 carbons. The alkyl group can be substituted or unsubstituted. When substituted the substituted group(s) is preferably, hydroxyl, cyano, alkoxy, =O, =S, $NO_2$ or $N(CH_3)_2$, amino, or SH. The term also includes alkenyl groups that are unsaturated hydrocarbon groups containing at least one carbon-carbon double bond, including straight-chain, branched-chain, and cyclic groups. Preferably, the alkenyl group has 1 to 12 carbons. More preferably, it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. The term "alkyl" also includes alkynyl groups that have an unsaturated hydrocarbon group containing at least one carbon-carbon triple bond, including straight-chain, branched-chain, and cyclic groups. Preferably, the alkynyl group has 1 to 12 carbons. More preferably, it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

Such alkyl groups can also include aryl, alkylaryl, carbocyclic aryl, heterocyclic aryl, amide and ester groups. An "aryl" group refers to an aromatic group that has at least one ring having a conjugated pi electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower allyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein et al., International PCT Publication No. WO 92/07065; Usman et al., International PCT Publication No. WO 93/15187; Uhhman & Peyman, supra, all are hereby incorporated by reference herein). There are several examples of modified nucleic acid bases known in the art as summarized by Limbach et al., 1994, *Nucleic Acids Res.* 22, 2183. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, *Biochenuistry,* 35, 14090; Uhlman & Peyman, supra). By "modified bases" in this aspect is meant nucleotide bases other than adenine, guanine, cytosine and uracil at 1' position or their equivalents.

In one embodiment, the invention features modified nucleic acid molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, 1995, *Nucleic Acid Analogues: Synthesis and Properties, in Modent Synthetic Methods*, VCH, 331-417, and Mesmaeker et al., 1994, *Novel Backbone Replacements for Oligonucleotides, in Carbollydrate Modifications in Antisense Research*, ACS, 24-39.

By "abasic" is meant sugar moieties lacking a base or having other chemical groups in place of a base at the 1' position, see for example Adamic et al., U.S. Pat. No. 5,998, 203.

By "unmodified nucleoside" is meant one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I-VII and/or other modifications described herein.

In connection with 2'-modified nucleotides as described for the present invention, by "amino" is meant 2'-$NH_2$ or 2'-O-$NH_2$, which can be modified or unmodified. Such modified groups are described, for example, in Eckstein et al, U.S. Pat. No. 5,672,695 and Matulic-Adamic et al., U.S. Pat. No. 6,248,878, which are both incorporated by reference in their entireties.

EXAMPLES

The following are non-limiting examples showing the selection, isolation, synthesis and activity of nucleic acids of the instant invention.

Example 1

Bioanalytical Method for the Detection of Double Stranded Oligonucleotides and siNA in Animal Tissues Materials siNA used in this study targeted HBV site 1580. The three different chemistries used comprised Stab 7 is the sense strand and Stab 8 is antisense strand (Table I). Compound #s are in brackets.

1. 7 (30612)/8 (30620)
2. chol-7 (31564)/8 (30620)
3. chol-trigal-7 (31926)/8 (30620)

Sequences of the siNA are shown below:

```
7:                                      (SEQ ID No: 1)
5' B uGuGcAcuucGcuucAccuTT B Chol-7:                                 (SEQ ID No: 2)
5' (H)2ZTaB uGuGcAcuucGcuucAccuTT B Chol-trigal 7:                          (SEQ ID No: 3)
5' (H)2ZTa B uGuGcAcuucGcuucAccuTT BaTKB 8:                                      (SEQ ID No: 4)
5' AGGuGAAGcGAAGuGcAcAT$_s$T
wherein:
Upper case = DNA
Italics upper case = 2'-OMe A or G
Lower case u,c = 2; fluoro U, C
a = ribo A
T = deoxy T
B = inverted abasic
Z = sbl: symmetrical bifunctional linker
H = chol2: capped cholesterol TEG
(. . .)2 = two branches off of sbl
K = tri-gal: deoxy ribose with three N-acetyl
galactosamines attached by 22 atom linkers
```

The capture and reporter oligos used for the detection of 7 or 8 are as follows.

```
Biotinyl capture oligo (#31617) for 7:
5' b aggugaagcg              (SEQ ID No: 5)

Biotinyl capture oligo (#31613) for 8:
5' b ugugcacuuc              (SEQ ID No: 6)

FITC labeled reporter oligo (#31618) for 7:
5' aagugcacauu F             (SEQ ID No: 7)

FITC labeled reporter oligo (#31615) for 8:
5' gcuuccacuuu F             (SEQ ID No: 8)
wherein:
Lower case = 2'OCH3
b = Biotin
F= Fluorescein
```

Methods

The two methods that include enrichment of specific liver cell types and detection of siNA by hybridization in biological samples are described in detail below.

Enrichment of Specific Cells:

Three types of liver cells including hepatocytes, kupffer and endothelial cells were enriched using the following procedure.

Animals were injected with various siNA duplexes (30 mg/kg of mouse weight) and saline subcutaneously. At different time intervals, the mice were anesthetized with a Xylazine/Ketaset mixture (188 ul Ketaset, 60 ul Xylaxine, 752 ml water). Animals were then perfused with 37° C. Liver Perfusion Medium (bnvitrogen), until the liver was blanched. A 30 cc syringe containing 37° C. collagenase perfusion buffer [Liver Perfusion Medium plus 5 mM $CaCl_2$ and 0.5 mg/ml collagenase (Sigma Type IV)] was used in a next perfusion step at a rate of 3-4 ml/min. Livers were gently removed from the animals and a piece of liver removed and placed in a pre-weighed lysis tube on dry ice. The remainder of the liver was placed in a 50 ml tube with 25 ml of ice-cold Hepatocyte Wash Buffer (Invitrogen). Samples were kept on ice until cell separation was observed. During all subsequent steps, ice cold Hepatocyte Wash Buffer was used and cells were kept on ice.

Livers were placed in Hepatocyte Wash Buffer in 25×100 mm petri dishes sitting on ice. Using a 150 mesh screen dish, livers were placed in the strainer and were gently scraped over the mesh with a glass pestle until only connective tissue remained in the strainer. The resulting cell suspension was transferred to a new 50 ml tube on ice; and the strainers and petri dishes were washed with additional ice-cold wash buffer. Washes were then pooled with the cell suspension. The suspension was divided from each mouse liver into two 50 ml tubes. The volume was brought up to 40 ml with ice cold Hepatocyte Wash Buffer. Samples were centrifuged at 580 rpm for 5 min at 4° C. in a Beckman CS-6C tabletop centrifuge with low brake. The resulting supernatant was pipetted to a new a 50 ml tube while being careful not to disrupt pellet (hepatocytes). The hepatocyte pellet was resuspended with 40 ml ice cold wash buffer, and centrifugation was repeated. The two tubes were then pooled in third wash. A total of three washes was used for hepatocytes. The supernatant was aspirated from the hepatocyte tubes. The cells were then pooled into one tube with 25 ml Hepatocyte Wash Buffer, counted and viability determined (generally a 1:5 dilution).

Next, the volume of solution required to get $5 \times 10^6$ cells was calculated and this volume was centrifuged at 580 rpm for 5 minutes at 40° C. The supernatant was removed and the cell pellet stored at −700° C. The supernatant is then transferred from non-hepatocyte containing tubes to new tubes that are centrifuged at 850 rpm for 10 minutes to remove any remaining hepatocytes. The supernatant is transferred into new tubes and spun at 1800 rpm for 10 minutes to pellet kupffer and endothelial cells. Cells were pooled and resuspend in 10 ml HWS. Cells were then counted and viability determined (generally a 1:2 dilution). Samples were then incubated with anti-mouse CD14 (to enrich kupffer cells) at a concentration of 1 ug/1 million cells in 1×PBS containing 0.1% BSA at 4° C. with rotating for 30 minutes for 1 hour. Samples were then washed with Dynabead M450 sheep anti-mouse IgG by placing in a tube, and adding 1-2 ml PBS/BSA; resuspending, and then placing on a magnet. After 1 minute, supernatant was removed, the wash repeated, and the sample resuspended with PBS-BSA to the original volume that was removed from the bead stock. The Dynabeads were then added to cells (incubated with antibody) at a concentration of $1\text{-}2 \times 10^7$ Dynabeads per ml of cells (10-40 million cells per ml) and incubated for 30 minutes at 4° C. while rotating. Dynabeads were then incubated with a magnet and unbound cells were removed and were then transferred and counted (the unbound cells were used in next step). The Dynabeads were then washed with PBS/BSA 4 or 5 times. For the hybridization assay, cells were lysed with beads attached in 3M GITC. The supernatant from above step containing unbound cells was centrifuged (CD14 negative) at 1800 rpm for 10 minutes to remove antibody. The cells were resuspended in 10 ml PBS-BSA. The above process was repeated with anti-mouse CD105 antibody to capture endothelial cells.

Hybridization Assay

Principle of Hybridization Assay:

The hybridization assay uses capture and reporter oligonucleotides that are complementary to differing regions of a target oligonucleotide (e.g., siNA) sequence and that specifically interact with the target sequence by Watson-Crick base pairing (see for example FIG. 1A). The assay is performed in the following steps. A high salt buffer wash is used to remove unbound species in each step.

A capture oligonucleotide is immobilized on streptavidin coated plate through biotin interaction. Any other high affinity capture systems or covalent likers and surfaces can similarly be used. The sample-containing the target oligonucleotide sequence is added to the wells and a portion of the target sequence is bound by the capture oligonucleotide. In case of duplex oligonucleotides, the target sequence (e.g., siNA) is first separated by heating at 90° C. for about 10 minutes followed by capture. The target sequence is detected by adding a FITC carrying detection oligonucleotide (or other suitable detection oligonucleotide) complimentary to a portion of the target A oligonucleotide sequence (e.g., siNA). Alternately, the FITC carrying detection oligonucleotide is first combined with the capture oligonucleotide on the surface, and then the target oligonucleotide sequence is added to the surface such that a first portion of the target sequence is bound by the capture oligonucleotide and a second portion of the target sequence is bound by the detectopm oligonucleotide. The surface is then washed to remove non-hybridized detection oligonucleotide. The quantitation of FITC/target is done by anti-FITC antibody that carries HRP followed by peroxidase assay. FITC is placed at either 5' or 3' position, and the detection oligonucleotide giving best signal to noise is used in the test configuration.

Non-Limiting Example of Hybridization Assay Protocol:

A solution of 10 ml of biotin conjugated capture oligonucleotide was prepared at 1 pmole/uL (1 uM) in 20 mM Tris, pH 7.5, and was pipetted into a Streptawell plate (100 pmole per well total) at 100 uL per well. The plate typically has a capacity to bind 80 pmole of biotin. The plate was then incubated at room temperature for 5 minutes to 1 hour on a shaker. The plate contents were discarded and the plate was washed twice with 200 uL per well of high salt wash buffer (0.1 M Tris pH 9.0; 1 M NaCl, 0.1% tween 20; 2 mM $MgCl_2$). A solution of 30 mL 1M GITC buffer (1M GITC, 0.5M NaCl, 0.1M Tris pH 7.5, and 10 mM EDTA) was then prepared. An aliquot (11 ml) of the GITC buffer was set aside and 0.1 mg/ml liver homogenate was added to the remaining buffer volume. Experimental and standard samples were prepared in the above buffer containing liver homogenate. The highest conconcentraion was serially diluted 2-fold to obtain the desired range of an eleven point standard curve. When using the duplex target, a 2× concentration the sample was heated at 90° C. for 10 minutes, then 50 ul was irmmediately added to a Streptawell plate that already contained 50 ul of buffer. The sample was then incubated at room temperature for 10 minutes on a shaker. The plate contents were decanted and the plate was subsequently washed five times with 200 uL of high salt wash buffer per well. The detection oligonucleotide was diluted to 100 pmols/ml concentration in 1M GITC buffer (without liver homogenate) and was added to the plate at 100 uL per well and incubated at room temperature for 1 hour on a shaker. The plate contents were decanted and the plate was subsequently washed five times with 200 uL of high salt wash buffer per well. HRP-anti FITC antibody was diluted 20,000-fold in 1%BSA/1× PBS and was added at 100 uL per well and incubated at room temperature for 1 hour on a shaker. The plate contents were decanted and the plate was subsequently washed five times with 200 uL of high salt wash buffer per well. TMB substrate was prepared according to the manufacture's instructions and was added at 100 uL per well. The assay was developed for 15-20 minutes at room temperature on a bench without shaking. Stop solution was added (100 uL, 1M $H_3PO_4$) per well, and plates were read at 450 nm with 595 nm correction using a ThermoMax plate reader from Molecular Devices using SoftMax Pro software. Alternately, 10 mL of capture probe (biotin-probe) is prepared at 1 nmole/μL (1 μM) in 20 mM Tris pH 7.5, and pipetted at 100 μL per well on Streptawell plate (100 pmole per well total). The plate has an 80 pmole biotin binding capacity. Incubate at room temperature for 10-60 min on shaker. Prepare 20 mL of 1 M GITC buffer (1 M GITC, 0.5 M NaCl, 0.1 M Tris pH 7.5, and 10 mM EDTA). Add homogenized tissue sample from naive animal to 10 mL buffer. Prepare the standard in 1 M GITC buffer containing tissue homogenate. Prepare standards in the range of 27.35 to 0.00267 ng/mL by two-fold serial dilution. Prepare any quality control (QC) samples in the same manner. Prepare samples (300 μL) by ≧25-fold dilution in 1 M GITC buffer. Transfer samples and standards on the 96-tube plate and heat at 90° C. for 10 min. During above step, decant contents of plate containing capture probe to waste, and wash plate twice with 200 μL per well high salt wash buffer (0.1 M Tris pH 9.0; 1 M NaCl, 0.1% Tween 20; 2 mM $MgCl_2$). Prepare 5 mL of reporter probe at 100 pmols/mL concentration in 1 M GITC buffer and add 50 μL per well. The fluoro-probe should be on the plate just prior to the addition of heated sample/standard. Add 50 μL of heated samples/standards to the 96-well plate containing probes. Incubate at room temp for 5 min on shaker. Decant plate contents to waste, and wash plate 5 times with 200 μL per well using high salt wash buffer. Dilute HRP-anti FITC antibody 20,000-fold in 1× PBS containing 0.1 mg/mL BSA and add 100 μL per well. Incubate at room temperature for 1 hr on shaker. Decant plate contents to waste, and wash plate 5 times with 200 μL per well using high salt wash buffer. Prepare TMB substrate according to manufacture's instruction and add 100 μL per well. Develop assay for 20 minutes at room temperature without shaking. Add 100 μL 1 M $H_3PO_4$ per well, measure absorbance 450 nm with 595 nm correction. (ThermoMax plate reader from Molecular Devices using SoftMax Pro software).

Results

Standard Curves of siNA Concentration Obtained by Hybridization Assay:

The detection of double stranded oligonucleotides (e.g., siNA) involves separate quantification of any unhybridized single stranded (e.g., sense and antisense) sequences present in a sample as well as quantification of duplex siNA sequences based on the concentration of sense and antisense strand sequences that result from treatment of the sample under conditions suitable for dissassociation of the sense and antisense strands. For each sample, three separate assays including detection and quantification of a single stranded sense strand, a single stranded antisense strand, and the duplex were conducted. The duplex sample was prepared by heating the duplex (comprising 100 uM sense and 110 um antisense strands) in water for 90° C. for 10 min and then allowing it to cool down to room temperature. The lower concentrations used in experiments were obtained from diluting the duplex stock. The samples for standard curves were prepared by two-fold serial dilution. The assays were done in 1M GITC buffer that contained 0.1 mg/ml naive liver homogenate to mimic the conditions from liver samples. The assays were performed as described in the protocol given above for the hybridization assay. Results are given in FIG. 2. The limit of detection (single strand and duplex form of the sense strand but only the single stranded form of antisense strand) was determined:

7: 7.8 fmoles/ml

Chol-7: 31.2 fmols/ml

Chol-trigal-7: 31.2 fmols/ml

8: 31.2 fmols/ml

The standard curves for sequence 7 in single stranded or duplex form overlap, suggesting the efficient detection of sense strand in duplex form in the presence of competitive amounts of antisense strand. This observation was true for Chol-7 and Chol-trigal-7 but only up to 500 fmols/ml concentration of duplex. Therefore, the presnt assay for detection of Chol-7 and Chol-trigal-7 siNAs are performed at less than 500 fmols/ml concentration. The assay can be modified however for optimized detection at differing concentrations of differing siNA sequences and siNA conjugate sequences by altering assay conditions such as the length of the capture oligonucleotide sequence, hybridization conditions etc.

Detection of siNA Quality Control Samples be Hybridization Assay:

In order to check the reproducibility of assay, the known concentrations of quality control (QC) samples of seqeunces 7 and 8 were prepared and assayed to see if the similar values for them are obtained by comparing to standard curves. The QC1 samples were prepared by direct dilution of known concentrations of stocks in 1M GITC buffer and used immediately while QC2 samples were prepared similarly but stored at −70° C. overnight prior to use. The results are shown in FIG. 3. In all cases, the QC samples showed the values comparable to that of standards with less than 10% variation, demonstrating the reproducibility of assay.

Detection of Potential Metabolites:

5' truncated versions of the 7 and 8 sequences were synthesized and assayed to check the ability of hybridization to detect possible siNA metabolites. The sequences of these molecules are given below.

```
7:
5' B uGuGcAcuucGcuucAccuTT B        (SEQ ID No: 1)

7(n-2):
5' GuGcAcuucGcuucAccuTT B           (SEQ ID No: 9)

7(n-3):
5' uGcAcuucGcuucAccuTT B            (SEQ ID No: 10)

7(n-5):
5' cAcuucGcuucAccuTT B              (SEQ ID No: 11)
```

-continued

```
7(n-9):
5' ucGcuucAccuTT B                 (SEQ ID No: 12)

8:
5' AGGuGAAGcGAAGuGcAcAT₅T          (SEQ ID No: 4)

8(n-1):
5' GGuGAAGcGAAGuGcAcAT₅T           (SEQ ID No: 13)

8(n-2):
5' GuGAAGcGAAGuGcAcAT₅T            (SEQ ID No: 14)

8(n-4):
5' GAAGcGAAGuGcAcAT₅T              (SEQ ID No: 15)

8(n-6):
5' AGcGAAGuGcAcAT₅T                (SEQ ID No: 16)
```

As shown in FIG. 4, the siNAs with up to 3 nucleotide deletions are detected with equal or slightly better efficiency. The deletions of 4-5 nucleotides results in marked reduction in sensitivity while the siNAs with more than 6 nucleotide constructions are not detected at all. Thus, the current assay is essentially capable of detecting full length three nucleotides deleted siNAs. The assay can be modified however to distinguish such metabolites from full length material by altering assay conditions such as the length of the capture oligonucleotide sequence, hybridization conditions etc.

Effect of Hepatocyte Lysate on Hybridization Assay:

The hybridization assay was standardized in the presence of 0.1 mg/ml naive liver homogenate. However, the detection of siNA in specific liver cell types (e.g., hepatocytes) involves assessing the effect of hepatocyte lysate on the hybridization assay. In the experiment described below, the effect of various concentrations of hepatocyte lysates was determined on detection of Chol-7/8 siNA sequences. As shown in FIG. 5, the presence of 2.5E+5 hepatocyte lysate/ml decreased the sensitivity of detection on chol-7 while 8 was unaffected by the presence of hepatocyte lysate. This suggests the use of less than 2.5E+5 hepatocytes lysate/ml for optimal detection of siNA in in vivo samples.

Effect of Monkey Plasma on Hybridization Assay:

To support potential pre-clinical testing of siNA constructs in primates, the effect of monkey plasma on the detection of 7/8 siNA duplex by hybridization assay was tested. Three different concentrations of monkey plasma in buffer containing 0.5M NaCl, 0.1M Tris pH 7.5, and 10 mM EDTA were used. The buffer did not contain GITC. Results are shown in FIG. 6. The use of up to 10% monkey plasma had no effect on detection of either chol-7 or 8 single stranded sequences. Assay conditions can be modifed for the detection of siNA molecules in various blood or plasma samples, for example by diluting the blood or plasma sample to an appropriate concentration as determined in this example, or alternately by changing the sequence or composition of the capture and detection oligonucleotides.

Detection of siNA Constructs in Mouse Hepatocytes:

The cellular enrichment method and hybridization assay method described above were used to determine the concentration of Chol-7/8 and 7/8 siNA duplex in mouse hepatocytes following SC injection (30 mg/kg of mouse weight). FIG. 7 shows the results of this study over a time course of 100 hours post administration. As shown in the Figure, the Chol-7/8 duplex is present at higher concentration in hepatocytes compared to the 7/8 duplex, suggesting that cholesterol siNA conjugates have increased uptake in hepatocytes.

Detection of siNA Constructs in Rabbit Ocular Tissue Following a Single Intravitreal Administration of siNA.:

New Zealand white (NZW) rabbits received siNA as single bilateral injections of 0.5 mg/eye. At 1, 4, and 8 hours, and 1, 2, 3, 4, 5, 7, 9, 11, and 13 days, animals were sacrificed and plasma, vitreous humor, and retina/choroid were isolated. Rabbit tissues obtained from the study were analyzed for siNA using a hybridization-ELISA method of the invention. To assess the total concentration of either the sense or the antisense strand of the siNA in a tissue sample containing siNA duplex, the sample was homogenized in denaturant and heated. The strand of interest was then captured on a streptavidin plate containing a complementary biotinylated ~14-mer oligonucleotide. A complementary reporter ~9-mer oligonucleotide with a conjugated fluorescein provided the epitope for an anti-fluorescein-peroxidase coupled antibody to allow colorametric detection.

The rabbit ocular tissue and plasma samples were analyzed for siNA by using the hybridization-ELISA method over the working concentration range of 0.027-7.013 ng/mL for sense strand and 0.026-6.663 ng/mL for antisense strand. Taking sample dilutions into account, the effective quantitation range for the assay was 2.67 to 683.8 ng/mL for vitreous/plasma and 0.0267 to 6.838 ng/mg for retina/choroid. The assay can detect either strand of the siNA with 2-4 nucleotide deletions with >70% efficiency. Thus, the values reported by assay in the experimental samples would reflect full length as well as 2-4 nucleotide-truncated strands.

The retinaichoroid samples were prepared at a concentration of 100 mg/mL in tissue homogenization buffer (3 M guanidine isothiocyanate, 0.5 M NaCl, 0.1 M Tris pH 7.5, 10 mM EDTA). This mixture was homogenized twice in Bio-101 Homogenizer (savant) with a speed setting of 6.0 and a run time of 12 sec. Vitreous was homogenized in a Bio-101 Homogenizer (savant) with a speed setting of 6.0 and a run time of 12 sec. The homogenized solutions were flurher diluted ≧25-fold in 1 M GITC Buffer (1 M guanidine isothiocyanate, 0.5 M NaCl, 0.1 M Tris pH 7.5, 10 mM EDTA). The plasma samples were diluted ≧25-fold in 1 M GITC buffer. The samples were stored at −80° C. prior to use. The 11-point standard curves were fit to the four-parameter logistic regression $[y=(A-B)/(1-(X/C)^D)]$. The concentration of siNA duplex in experimnental and QC samples was derived from their standard curve. The standards, experimental and QC samples were prepared with equal amounts of tissue material to normalize for the effect of tissue samples. The assay quantitated the total amount of sense or antisense strand present in the samples. The amount of duplex was calculated by doubling the smaller value of either strand in the sample.

The data for the standard curve parameters are shown in Table II. The back calculated calibration standard concentrations are shown in Tables IV and V. Quality control sample data is shown in Tables VI and VII. siNA sample data is shown in Tables VIII, IX, and X. Sequences for the assay are shown in Table XI.

Methods to Increase Accuracy at Higher Assay Concentrations:

At higher assay concentrations, competitive binding of sense and antisense oligonucleotide sequences following duplex dissassociation may result in inaccurate results. In such instances, the method can be modified to remove sequences that may otherwise compete for binding to a target siNA oligonucleotide sequence by the capture oligonucleotide. The removal of competitive sequences can be accomplished by using affinity capture using, for example, a biotinylated partial length or full length complementary sequence to the competitor sequence. The concentration of the biotinylated sequence can be altered such that all competitor sequences are removed from the assay prior to quantification of the target siNA oligonucleotide sequence. In a non-imiting example, where the antisense strand of the duplex is being assayed, a biotinylated complementary sequence (biotinylated antisense sequence) is added to the assay after the duplex is dissassociated by heating. Removal of the biotinylated antisense sequence with bound sense competitor sequence allows for the accurate determination of the total antisense strand concentration in the sample without the risk of competitive binding and duplex formation. FIG. 8 shows the results of a study in which excess biotinylated antisense strand was used to capture dissociated sense strand of a siNA duplex after heating. The heated duplex (90 degrees C.) was mixed with biotinylated sense sequences at room temperature in a 96 well plate with vigorous pipetting followed by vigorous vortexing for 10 minutes. The plate was then centrifuged and supernatants transferred to a hybridization assay plate. The value of antisense strand duplex concentration with the sense strand removed (duplex, heated, beads) is compared to antisense strand duplex concentration without removal of the sense strand (duplex, heated), intact duplex (duplex, unheated), and antisense strand alone (antisense, heated). As shown in FIG. 8, the concentrations of the duplex as determined by the concentration of the antisense strand following heat dissassociation and removal of the sense strand (duplex, heated, beads) is very similar to the control antisense strand concentration, whereas the sample in which sense strand was not removed (duplex, heated) failed to give accurate results at higher concentrations. Subtraction of the concentration of any unhybridized antisense sequence from the total concentration of antisense sequence provides the concentration of duplex via antisense strand determination.

Applicability of Assay to Nucleic Acid (e.g. siNA) Molecules having Differing Chemical Modifications:

Two different siNA chemistries (Stab 7/8 and Stab 9/10, Table I) of the same siNA sequence where evaluated using the hybridization assay methodology of the invention in which the concentration of dissassociated sense strand was measured following heating of the siNA duplex at 90 degrees C. for 10 minutes. As shown in FIG. 9, both Stab 7/8 and Stab 9/10 siNA duplexes show similar behavior from 1 to 1000 fmoles/ml of sample, illustrating that the assay can efficiently detect siNA sequences having differing chemical modifications applied to the same sequence.

Example 2

Development of Antibody Assays for the Detection and Quantitation of Nucleic Acid Molecules Monoclonal antibodies (mAb) are developed to recognize particular nucleic acid sequences or sequences containing an epitope of choice (e.g., modified nucleotide or non-nucleotide moieties) that is unique to a particular target oligonucleotide to be detected and/or quantified. For example, a mAb CA1USR, has been developed having a high degree of affinity for the 2'-deoxy-2'-C-allyl Uridine modification (see for example Radka et al., U.S. Ser. No. 10/366,191 filed Feb. 12, 2003, incorporated by reference herein. Nucleotides that do not contain the modification are incapable of competing for the binding of the mAb, allowing for the selective detection and/or quantitation of a target sequence in vitro and it, vivo. The oligonucleotide target can be single stranded or double stranded (e.g., a linear siNA molecule or siNA duplex). As such, the mAb can be used for direct detection/quantitation of both single stranded or double stranded siNA molecules (see for example FIG. 1C).

Example 3

Development of HPLC Assays for the Detection and Quantitation of Nucleic Acid Molecules The use of chromatography, such as high performance liquid chromatography (HPLC) in the detection and quantitation of nucleic acid molecules is well recognized in the art (see for example Gilar, 2001, *Analytical Biochemistry*, 298, 196 and Apffel et al., 1997, *Journal of Chromatography*, 777, 3). Chromatographic methods of the present invention can be used to detect single stranded nucleic acid molecules and duplex nucleic acid molecules in the same analytical method or in separate analytical methods that can combine different chromatographic approaches, such as reverse phase, ion exchange, ion-pairing, and/or size exclusion chromatography. Chromatographic analysis can be coupled with mass spectrometry methods to analyse sequence identity, base composition, modifications, and metabolites of nculeic acid molecules present in a sample, such as a biological sample.

In a non-limiting example, a HPLC method is developed for the detection and quantitation of an oligonucleotide target (e.g., siNA) duplex and single stranded sequences, such as sense strand sequences and antisense strand sequences, by distinguishing between those sequences that are unhybridized and hybridized in the system or sample (see for example FIG. 1C). In addition, a HPLC assay of the invention is developed to dinstinguish the presence of and/or composition of any metabolites of oligonucleotide sequences present in sample.

A sensitive and selective HPLC method was developed for the quantitation of a siNA duplex SIR-30612/30620 in cynomolgus monkey plasma. SIR-30612/30620 comprises a duplex having a sense strand sequence of 5'-B uGuGcAcuucGcuucAccuTT B (SEQ ID No: 17) where u=2'-deoxy-2'-fluoro Uridine; c=2'-deoxy-2'-fluoro Cytidine; G=2'-deoxy Guanosine; A=2'-deoxy Adenosine; T=Thymidine; and B=inverted deoxyabasic, and an antisense strand sequence of 5'-AGGuGAAGcGAAGuGcAcATsT (SEQ ID No: 18) where u=2'-deoxy-2'-fluoro Uridine; c=2'-deoxy-2'-fluoro Cytidine; G=2'-O-methyl Guanosine; A=2'-O-methyl Adenosine; T=Thymidine; and s=phosphorothioate intemucleotide linkage. SIR-30612/30620 and an internal standard were extracted from heparinized monkey plasma using a two-step, solid phase extraction procedure. HPLC analysis was performed by anion exchange chromatography, using gradient elution with ultraviolet detection at 260 nm. The method was successfully applied to the determination of SIR-30612/30620 in samples from pharmacokinetic studies in monkeys.

Solid-Phase Extraction

Solid phase extraction (SPE) was utilized to isolate SIR-30612/30620 from plasma samples. Samples were loaded and eluted from a SAX SPE cartridge, dried, reconstituted in water, and desalted on a CG300S SPE cartridge. Both SPE steps were carried out on a 20 position SPE manifold with vacuum. For each plasma sample; a 100 uL aliquot was transferred to a 1.5 mL eppendorf tube, and 800 uL of 20 mM Ammonium Acetate, 1 mM EDTA, 10 mM Tris, pH 8 buffer, and 100 uL internal standard, (10 ug/mL in buffer) were subsequently added. Samples were loaded onto SAX cartridges (50 mg, Varian), equilibrated with ACN, water, and buffer (1.0 mL each). Following loading, samples were washed with 1 mL of buffer. Samples were eluted with two 500 uL aliquots of 2M ammonium acetate/15% ACN. The SAX eluates were dried in a Speedvac on the "high" heat setting for approximately 2 hours. Samples were reconstituted in 1 mL of water and loaded on CG300S cartridges (50 mg, TosoHaas), equilibrated with ACN, water, and 2M ammonium acetate (1.0 mL each). Following loading, samples were washed with 1 mL of water. Samples were eluted with two 500 uL aliquots of 40/40/20 ACN/MeOH/water. The CG200S eluates were dried in a Speedvac on the "high" heat setting for approximately 2 hours. Following drying the extracted samples were reconstituted in 200 uL saline and analyzed by SAX HPLC.

Instrumentation and Chromatographic Conditions

HPLC analysis was performed on a Waters 2790 HPLC System (Milford, Mass.). The system consisted of a binary pump, a thermostated column compartment, a thermostated autosampler and a UV detector. Data acquisition and analysis was performed using Waters Empower Pro software. Samples were analyzed on a DNApak PA-100, 4×250 mm column (Dionex, Sunnyvale, Calif.) maintained at 60° C. Samples (200 μL) were injected onto the column and eluted with a gradient of 100% Mobile Phase A (40% ACN/25 mM NaClO4, 10 mM Tris, pH 8) to 100% Mobile Phase B (40% ACN/250 mM NaClO4, 10 mM Tris, pH 8) over 10 minutes at a flow rate of 1 mL/min. Detection was performed at 260 nm.

Alternative Analytical Methods

Extracted samples can also be analyzed by reverse phase chromatography. A non-limiting example of reverse phase analysis comprises the use of a reverse phase column (e.g., Vydac Protein C4, 5 micron, 150×4.6 mm), Mobile Phase A: 5% ACN/10 mM TEAA and Mobile phase B: 30% ACN/10 mM TEAA, with a gradient of 0 to 100% B in 10 minutes at a flow rate of 1.5 mL/min and a temperature of 70° C. The temperature can be varied to discriminate between single stranded species (e.g., siNA sense and/or antisense strands) and/or double stranded species (e.g., siNA duplex).

Example 4

Development of Electrophoresis Assays for the Detection and Quantitation of Nucleic Acid Molecules The use of electrophoresis, such as capillary gel electrophoresis (CGE) in the detection and quantitation of nucleic acid molecules is well recognized in the art (see for example Von Brocke et al., *Journal of Chromatography*, 991, 129 and Dedionisio et al., 2001, *Methods in Molecular Biology*, 162, 353). Electrophoretic methods of the invention are developed to detect single stranded nucleic acid molecules and duplex nucleic acid molecules, for example in the same analytical method. Electrophoretic analysis can be coupled with mass spectrometry methods to analyse sequence identity, base composition, modifications, and metabolites of nucleic acid molecules present in a sample, such as a biological sample.

In a non-limiting example, the methods of the invention are practiced using commercially available electrophoretic apparatus, produced for example by LKB (Bromma, Sweden) and Beckman Instruments (Fullerton, Calif.). The methods of the invention also can be practiced using a wide variety of commercially available capillary electrophoresis columns and buffers.

In a non-limiting example, a CGE method is developed for the detection and quantitation of an oligonucleotide target (e.g., siNA) duplex and single stranded sequences, such as sense strand sequences and antisense strand sequences, by distinguishing between those sequences that are unhybridized and hybridized in the system or sample (see for example FIG. 1C). In addition, a CGE assay of the invention is developed to dinstinguish the presence of and/or composition of any metabolites of oligonucleotide sequences present in sample.

Solid-Phase Extraction

Solid phase extraction (SPE) was utilized to isolate SIR-30612/30620 (see sequences above in Example 3) from plasma samples. Samples were loaded and eluted from a SAX SPE cartridge, dried, reconstituted in water, and desalted on a CG300S SPE cartridge. Both SPE steps were carried out on a 20 position SPE manifold with vacuum. For each plasma sample; a 100 uL aliquot was transferred to a 1.5 mL eppendorf tube, and 800 uL of 20 mM Ammonium Acetate, 1 mM EDTA, 10 mM Tris, pH 8 buffer, and 100 uL internal standard, (10 ug/mL in buffer) were subsequently added. Samples were loaded onto SAX cartridges (50 mg, Varian), equilibrated with ACN, water, and buffer (1.0 mL each). Following loading, samples were washed with 1 mL of buffer. Samples were eluted with two 500 uL aliquots of 2M ammonium acetate/15% ACN. The SAX eluates were dried in a Speedvac on the "high" heat setting for approximately 2 hours. Samples were reconstituted in 1 mL of water and loaded on CG300S cartridges (50 mg, TosoHaas), equilibrated with ACN, water, and 2M ammonium acetate (1.0 mL each). Following loading, samples were washed 5 times with 1 mL of water. Samples were eluted with two 500 uL aliquots of 40/40/20 ACN/MeOH/water. The CG200S eluates were dried in a Speedvac on the "high" heat setting for approximately 2 hours. Following drying the extracted samples were reconstituted in 100 uL H2O and fiurer desalted for 1 hour using a Millipore 0.025 μm membrane.

CGE Analysis

CGE analysis was carried out on a Beckman PACE-MDQ instrument using Beckman eCAP DNA capillaries having an inner diameter of 100 μm and a length of 27 cm. Tris-Borate was used as a buffer with a Beckman ssDNA 100-R Gel (this is a non-crosslinked polyacrylamide gel) as the gel matrix. Samples are run at a temperature of 30° C. with an injection voltage of 10 KV and a separation voltage of 10 KV. Injection times and run times can be varied to optimize separate. A typical run time is 60 minutes. A UV or LIF detector is typically used (the limit of detection for UV is typically around 0.1 μg/mL, while the limit of detection for LIF is typically around 0.1 ng/mL. Oligreen dye is used as intercalator for single strand LIF detection.

Example 5

Development of Nucleic Acid Sense Molecule Assays for the Detection and Quantitation of Nucleic Acid Molecules Nucleic acid sensor molecules can be used to detect the presence of and quantify nucleic acid molecules (e.g., oligonucleotides including siNA molecules) in a sample. Non-limiting examples of nucleic acid sensor molecules are described in Usman et al., International PCT Publication No. WO 01/66721, Seiwert et al., International PCT Application No. PCT/US02/35529, and Seiwert et al., U.S. Ser. No. 10/422,050, incorporated by reference herein.

In a non-limiting example, a nucleic acid sensor molecules are designed to discriminate between duplex and single stranded nucleic acid molecules present in a sample (see for example FIG. 1C) or between nucleic acid molecules having particular sequence compositions or having particular nucleotides, such as modified nucleotides. Dectection methods using nucleic acid sensor molecules are described in Usman et al., International PCT Publication No. WO 01/66721, Seiwert et al., International PCT Application No. PCT/US02/35529, and Seiwert et al., U.S. Ser. No. 10/422,050 and can similarly be applied to the methods of the instant invention to detect and quantify oligonucleotides (e.g., siNA) present in a sample.

Example 6

Development of LC-MS Assays for the Detection and Quantitation of Nucleic Acid Molecules As synthetic nucleic acid compounds (e.g., polynucleotides that mediate RNA interference such as siNA molecules) are being developed as therapeutics, knowledge of the metabolism and stability of these molecules is vital to understanding their pharmacokinetics. Information on RNAi degradation mechanisms is also crucial in the design of more stable oligonucleotide architectures that can survive nuclease decomposition. In the case of RNA interference mediating polynucloetides, the double stranded character of these molecules required new methods for detection and analysis of such compounds in biologic systems and samples.

Liquid chromatography coupled with electrospray mass spectrometry (LC-MS) has been used extensively to study the metabolites of synthetic oligonucleotides as it allows metabolites to be identified by their unique mass, something not possible with gel electrophoresis or chromatographic techniques alone. Oligonucleotides are not always easily analyzed by LC-MS due to non-volatile cations such as sodium and potassium that accompany the negatively charged phosphate backbone. The non-volatile cations interfere with electrospray analysis by reducing sensitivity and complicating the mass spectra. Researchers have used a variety of techniques such as adding solution phase cation chelators and cation exchange resins to alleviate the cation adduct problem in electrospray analysis. Despite the cation problem, LC-MS offers advantages for the analysis of oligonucleotides that not only include a measurement of mass but one that is done without excessive perturbation of the analyte. This is particularly important when studying duplexed RNAi mediating polynucleotides. The soft-ionization mechanism of electrospray has enabled the study of non-covalent interactions between a variety of biomolecules including double stranded oligonucleotides. Taking advantage of electrospray mass spectrometry's capabilities to preserve non-covalent complexes, applicant demonstrates the utility of a reverse phase LC-MS method for the analysis of a synthetic siNA duplex.

RNA Oligoizucleotides

A model Stab 7/8 (Table I) siNA construct [SIRNA 30620/30612] was synthesized using phosphoramidite chemistry (see for example McSwiggen et al., WO 03/70918). The sequence and molecular weights of the sense and antisense strands of the siNA are (from 5' to 3') B uGuGcAcuucGcuucAccuTT B (SEQ ID NO: 3) (6827.9 amu), and AGGuGAAGcGAAGuGcAcATsT (SEQ ID NO: 4) (7017.5 amu) respectively. The siNA duplex has a molecular weight of 13, 845.4. The uridine and cytosine bases contain fluoro groups at the 2' location on the ribose. On the antisense strand the guanine and adenine bases contain O-methyl groups at the 2' location of the ribose. The guanine and adenine bases on the sense strand are deoxyribonucleosides. The uppercase T represents deoxyribose thymine and the uppercase B represents an inverted abasic. The antisense oligonucleotide contains a phosphorothioate linkage between the two terminal deoxyribose thymines represented by the lower case S. The single strand oligonucleotides were annealed by mixing equal molar concentrations of each strand in a saline buffer, heating to 90° C. for 5 minutes and then cooling to room temperature.

LC-MS

A Shimadzu HPLC system comprising two LC-lOADvp pumps, a SPD-10Avp UV-Vis detector and a SCL-10Avp system controller was connected in-line to a Sciex API 365 triple quadrupole mass spectrometer. Samples were introduced via a Perkin-Ehmer Series 200 autosampler and reverse phase chromatography was carried out at 25° C. with an Xterra MSC18 2.1×50 mm column (Waters). Mobile phase buffer A consisted of 400 mM hexafluoroisopropanol (HFIP) 16.3 mM triethylamine (TEA), pH=7.9 and buffer B consisted of 200 mM HFIP 8.15 mM TEA in 50% methanol. The HFIP/TEA mobile phase was found to be particularly well suited for the reverse phase analysis of oligonucleotides as has been reported by others. Chromatography was carried out at 120 µl/min and starting at 30% B. Over 5 minutes buffer B was ramped linearly to 45% and then to 80% by 20 minutes.

The eluent from the UV-Vis detector on the HPLC was connected directly to the electrospray interface of the Sciex API 365 triple quadrupole MS via PEEK tubing. A switching valve was placed in-line after the UV detector to direct early eluting salts to waste instead of into the mass spectrometer. A cation exchange guard column (Optimize Technologies, Oregon) was also placed in-line before the MS (but after the switching valve) to remove excess cations. The Sciex API 365 was operated in negative ionization mode for all analyses and the mass range of 800-1900 amu was scanned with a 0.1 amu width step size in a 3 second scan time. Spectra were summed over a UV peak of interest and the electrospray charge states were deconvoluted using the BioAnalyst software supplied by Applied Biosystems. The masses present in the resulting deconvoluted spectra were compared manually to a table of possible nuclease derived metabolites.

Sample Preparation

Samples used for urine metabolism studies were prepared by spiking human urine with either single strands of the siNA or the annealed duplex to give a sample of 5 µM. Spiked urine samples were left at room temperature and aliquots withdrawn and tested at various time points. Spiked urine samples were mixed 1:1 with buffer A and 10 µL was injected directly on column.

Results

The proposed mechanism of RNA interference describes a protein complex termed the RNA-induced silencing complex (RISC) that separates the initial RNA duplex into its two single strand components. The active single strand or antisense strand, is then paired with its complementary mRNA target sequence resulting in cleavage of the target sequence and thereby preventing translation. Ideally an LC-MS method for the analysis of RNAi compounds should be able to detect all three oligonucleotide species that could potentially be present in the body; the intact duplex and the corresponding two individual single stranded oligonucleotides. Such information could provide insight on how the therapeutic siNA oligonucleotide exists in the proposed RNAi pathway as well as provide information on degradation mechanisms.

LC-MS analysis of single stranded oligonucleotides has been carried out using a variety of buffers and columns but little has been reported in the analysis of double stranded oligonucleotides particularly preserving the duplex in the gas phase. Some of the commonly used solvent systems for the analysis of oligonucleotides such as acetonitrile with cation chelators like imidazole and piperdine work well for single stranded oligonucleotides but disrupt the duplex. Other buffer systems commonly used for the analysis of non-covalent complexes such as ammonium acetate, preserve the duplex but greatly limit the number of charge states observed and/or do not produce suitable chromatographic separation. The observance of multiple charge states is advantageous when identifying unknown oligonucleotide degradation species. A greater number of charge states in the spectrum allows a more precise determination of the analyte's mass via spectral deconvolution. Unfortunately, the triethylammonium acetate (TEAA) buffer system that is traditionally used for the reverse phase separation of oligonucleotides greatly suppresses electrospray ionization. In response to the incompatibility between electrospray ionization and TEAA buffers, an ion-pairing buffer system employing HFIP has been developed. This buffer system has been shown to provide chromatographic separation of various oligonucleotides while retaining good electrospray behaviour. Overlayed chromatograms show the reverse phase elution order of the two single strands and duplex in FIG. 10. The HFIP/TEA ion-pairing buffer system not only permitted separation of duplex oligonucleotides from single strands but also allow duplex oligonucleotides to be preserved in the gas phase during electrospray analysis (FIGS. 10A and B). This result was surprising due to the harshness of the HFIP buffer system and the proposed increase in pH during the electrospray process. The spectrum of the intact duplex in the HFIP buffer displays several charge states that aids in the mass assignment of the oligonucleotide. As mentioned earlier, traditional buffers used for electrospray of non-covalent complexes do not produce a large charge enveloped so it is surprising to see the intact duplex with several charge states. The number of high charge states (−10, −11, −12) observed is particularly noteworthy, since non-denaturing buffers tend to produce lower charge states (less pH extremes) and columbic repulsion favors complexes with a smaller number of multiple charges. There is a small amount of denaturing caused by the electrospray process as evidenced by ions corresponding to the single strands. It is assumed that these ions are caused by denaturing from the electrospray process and not the mobile phase conditions as there are no peaks corresponding to the single strands observed in the UV 260 nm chromatogram.

Samples of the siNA duplex spiked into urine were examined at various time points and their degradation monitored. The overlayed chromatograms in FIG. 11A show that by day 6, most of the sense strand has completely degraded whereas the antisense and the duplex exhibit little if any degradation. A detailed look at the sense strand reveals that degradation had begun at day 3 (FIG. 11B). The deconvoluted electrospray mass spectrum of the sense strand at day 3 displays a variety of nuclease produced breakdown species (FIG. 12A). The observed masses correspond to nuclease cleavage starting from the 5 prime end and working towards the 3 prime end. This degradation pattern is expected as the 5 prime end contains fewer chemical modifications designed to protected the oligonucleotide from nuclease activity. Most of the oligonucleotide fragments observed arise from cleavages on the 3 prime side of the phosphate linkage however, the N-4 (cleavage at the 4$^{th}$ ribophosphate linkage) fragment contains the phosphate linkage as evidenced by the 80 amu increase in mass. Interestingly, there are no fragments from the N-1, 2, or 3 oligonucleotides. It is thought that the inverted abasic prevents exonuclease attack at the end of the oligonucleotide and degradation therefore "jumps" inward from endonucleases.

A similar degradation profile is observed for the single stranded anitsense strand but beginning later at 6 days (FIG. 12B). A slower onset of degradation in the antisense strand is evidence of the nuclease protection given by the o-methyl groups. The antisense strand does not contain the inverted abasic modification at the 5 prime end so once nuclease activity starts it is able to proceed from the end and work inward. A slower decomposition of the antisense strand would be expected to be important as it is this half of the siNA duplex that is thought to interact with the RISC complex to cause RNA interference.

Figure 13:
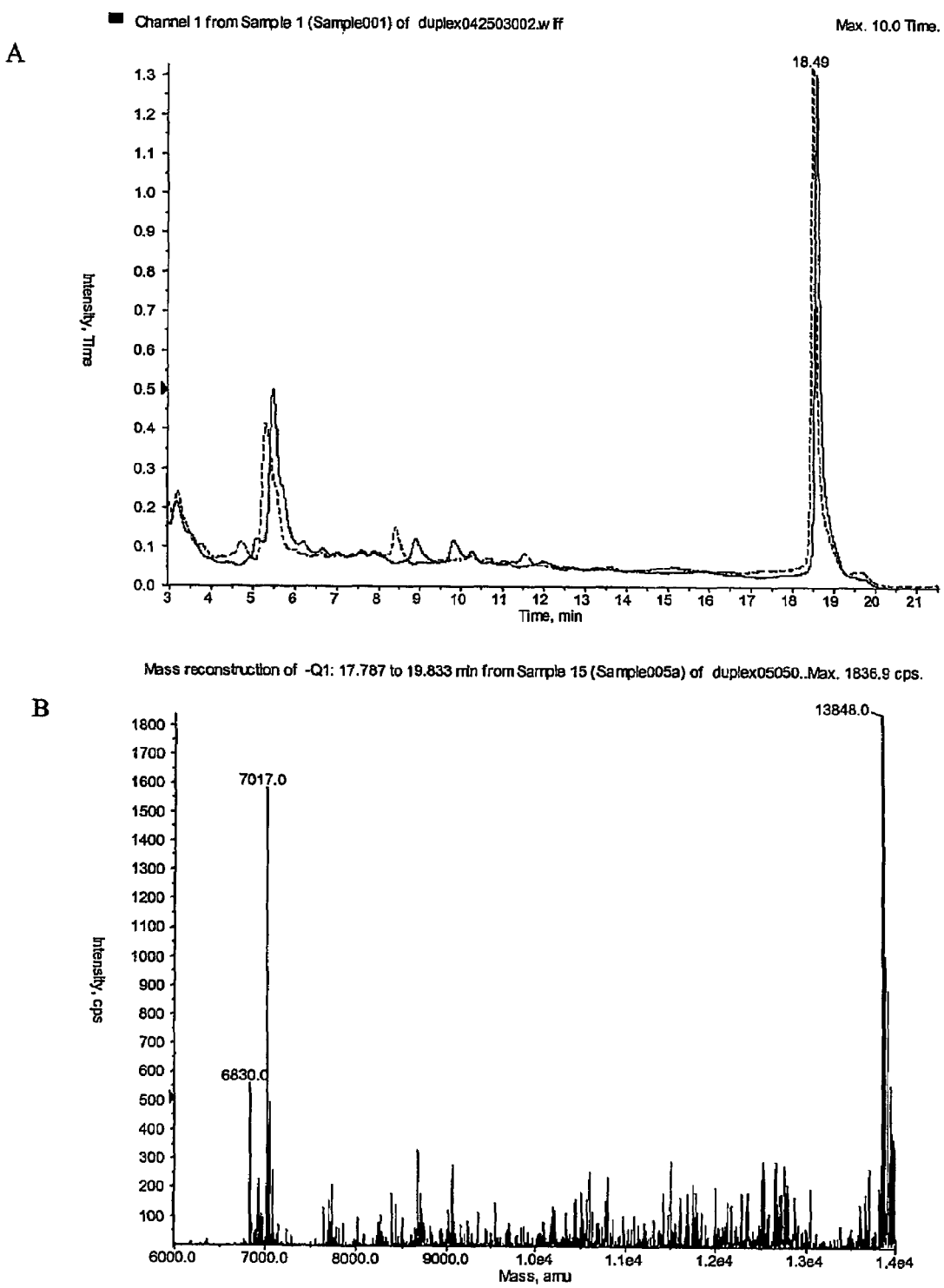
FIG. 13 shows a non-limiting example of the stablity of a siNA duplex when a siNA duplex spiked into urine was examined at various time points and their degradation monitored. (A) Chromatograms of the RNAi duplex at Day 0 (dotted line) and Day 11 eluting at 18 minutes. Duplex was spiked into urine at 5 µM and 10 µL injections were made on column. (B) The deconvoluted electrospray mass spectrum of the RNAi duplex eluting at 18 minutes at Day 11. The intact duplex is observed at 13,848 amu and the two single strands at 7017 and 6830 amu.
Figure 14:
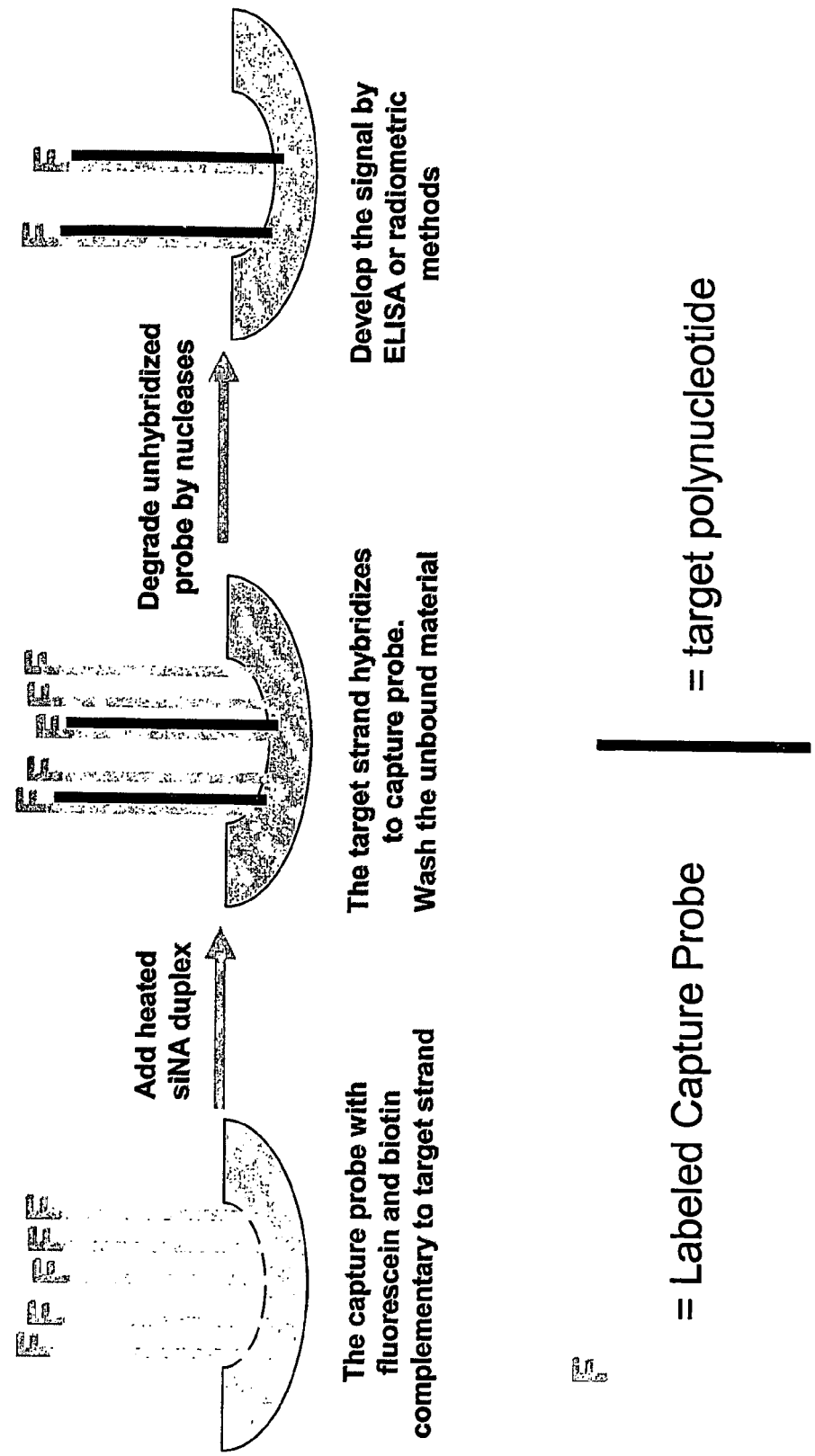
FIG. 14 shows a non-limiting example of a method of dection of a target polynucleotide of interest in which a dissociated siNA duplex (e.g., heated siNA sample) is added to a surface comprising an affixed labeled capture polynucleotide probe having sequence complementarity to the target polynucleotide of interest. The target polynucloetide hybridizes with the capture probe and the surface is washed to remove any non-hybridized material. The surface is then treated with a nuclease that cleaves only single stranded polynucleotide sequences. Treatment with the nuclease cleaves any non-hybridized capture polynucleotide (not hybridized with the target polynucleotide) from the surface. After washing the surface to remove any cleaved capture polynucleotide, the amount of signal is measured (e.g., by ELISA or radiometric methods) to determine the amount of target polynucleotide in the sample.

Unlike the single strands, the siNA duplex exhibits no degradation even after 11 days in urine (FIG. 13A). The chromatograms of the two time points overlap almost perfectly and the mass spectrum of Day 11 contains no degradation species. The deconvoluted mass spectrum does not contain any degradation species and shows the intact duplex and the two single strands (FIG. 13B). As mentioned earlier, there is some denaturing of the duplex caused by the electrospray process. Interestingly, even though the single strands are present in equal amounts, the antisense strand always has greater ion intensity.

As such, the ultility of a reverse phase LC-MS method for studying intact siNA polynucleotides has been demonstrated. Chromatographic separation of the duplex from the single strands and preservation of the siNA duplex in the electrospray was achieved using the hexafluoroisoproanol/triehthylamine buffer system. Degradation products observed in the model oligonucleotides were consistent with their chemical modifications. The ability to track enzymatic degradation products will be beneficial to studying the stability of various chemical modifications and tracking metabolites for pharmacokinetic studies of therapeutic RNAi compounds.

Example 7

Detection of Oligonucleotides in Cell/Tissue Samples

The method described in Examples 1-6 above can be applied to any tissue or cell sample, such as liver, lymphoid, heart, spleen, kidney, brain, intestinal, ovarian, breast, skin, lung, esophageal, epithelial, endothelial, optic or other tissue or cell sample. A sample is obtained from a subject by any suitable means (e.g. biopsy) and is processed under conditions suitable for analysis. Differing cell or tissue types can be isolated as described herein or otherwise as known in the art, to determine the concentration of oligonucleotides (e.g., siNA) in certain cell or tissue types. The method herein can be used to detect target oligonucleotide sequences in pre-clinical and clinical tissue or cell samples, such as in evaluating the toxicity, efficacy, pharmacokinetics, and pharmacodynamics of a clinical candiate oligonucleotide construct in pre-clinical animal experiments, during clinical trials of a siNA construct, or for monitoring in subjects after FDA approval.

Example 8

Detection of siNA in Blood/Serum Samples

The method described in Examples 1-6 above can be applied to any serum or blood sample, such as rodent, porcine, canine, primate, or human blood and/or plasma samples.

Similarly, the method described in Examples 1-6 can be applied to any sample of biological fluid, including blood, serum, urine, plasma, cerebrospinal fluid (CSF), optic fluid (vitrius), semen, milk, interstitial fluid, saliva, sputum and/or synovial fluid. A sample of the biological fluid is obtained from a subject by any suitable means (e.g. collection, blood draw, needle biopsy etc.) and is processed under conditions suitable for analysis. The method herein can be used to detect target oligonucleotide (e.g., siNA) sequences in pre-clinical and clinical fluid samples, such as in evaluating the toxicity, efficacy, clearance, pharmacokinetics, and pharmacodynamics of a clinical candiate siNA construct in pre-clinical animal experiments, during clinical trials of a siNA construct, or for monitoring in subjects after FDA approval.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifyng siNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markash groups or other grouping of alternatives, those skilled in the art will recognize that the invention is also thereby described in terms of any individual member or subgroup of members of the Markush group or other group.

TABLE I

Non-limiting examples of Stabilization Chemistries for chemically modified siNA constructs

| Chemistry | pyrimidine | Purine | cap | p = S | Strand |
|---|---|---|---|---|---|
| "Stab 00" | Ribo | Ribo | TT at 3'-ends | — | S/AS |
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | S/AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| "Stab 12" | 2'-fluoro | LNA | 5' and 3'-ends | — | Usually S |
| "Stab 13" | 2'-fluoro | LNA | — | 1 at 3'-end | Usually AS |
| "Stab 14" | 2'-fluoro | 2'-deoxy | — | 2 at 5'-end 1 at 3'-end | Usually AS |
| "Stab 15" | 2'-deoxy | 2'-deoxy | — | 2 at 5'-end 1 at 3'-end | Usually AS |
| "Stab 16" | Ribo | 2'-O-Methyl | 5' and 3'-ends | — | Usually S |

TABLE I-continued

Non-limiting examples of Stabilization Chemistries for chemically modified siNA constructs

| Chemistry | pyrimidine | Purine | cap | p = S | Strand |
|---|---|---|---|---|---|
| "Stab 17" | 2'-O-Methyl | 2'-O-Methyl | 5' and 3'-ends | | Usually S |
| "Stab 18" | 2'-fluoro | 2'-O-Methyl | 5' and 3'-ends | | Usually S |
| "Stab 19" | 2'-fluoro | 2'-O-Methyl | 3'-end | | S/AS |
| "Stab 20" | 2'-fluoro | 2'-deoxy | 3'-end | | Usually AS |
| "Stab 21" | 2'-fluoro | Ribo | 3'-end | | Usually AS |
| "Stab 22" | Ribo | Ribo | 3'-end | | Usually AS |
| "Stab 23" | 2'-fluoro* | 2'-deoxy* | 5' and 3'-ends | | Usually S |
| "Stab 24" | 2'-fluoro* | 2'-O-Methyl* | — | 1 at 3'-end | S/AS |
| "Stab 25" | 2'-fluoro* | 2'-O-Methyl* | — | 1 at 3'-end | S/AS |
| "Stab 26" | 2'-fluoro* | 2'-O-Methyl* | — | | S/AS |
| "Stab 27" | 2'-fluoro* | 2'-O-Methyl* | 3'-end | | S/AS |
| "Stab 28" | 2'-fluoro* | 2'-O-Methyl* | 3'-end | | S/AS |
| "Stab 29" | 2'-fluoro* | 2'-O-Methyl* | | 1 at 3'-end | S/AS |
| "Stab 30" | 2'-fluoro* | 2'-O-Methyl* | | | S/AS |
| "Stab 31" | 2'-fluoro* | 2'-O-Methyl* | 3'-end | | S/AS |
| "Stab 32" | 2'-fluoro | 2'-O-Methyl | | | S/AS |

CAP = any terminal cap, see for example FIG. 10.
All Stab 00-32 chemistries can comprise 3'-terminal thymidine (TT) residues
All Stab 00-32 chemistries typically comprise about 21 nucleotides, but can vary as described herein.
S = sense strand
AS = antisense strand
*Stab 23 has a single ribonucleotide adjacent to 3'-CAP
*Stab 24 and Stab 28 have a single ribonucleotide at 5'-terminus
*Stab 25, Stab 26, and Stab 27 have three ribonucleotides at 5'-terminus
*Stab 29, Stab 30, and Stab 31, any purine at first three nucleotide positions from 5'-terminus are ribonucleotides
p = phosphorothioate linkage

TABLE II

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument | | | | | |
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |
| B. 0.2 μmol Synthesis Cycle ABI 394 Instrument | | | | | |
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

TABLE II-continued

C. 0.2 µmol Synthesis Cycle 96 well Instrument

| Reagent | Equivalents: DNA/ 2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 µL | 60 sec | 180 sec | 360 sec |
| S-Ethyl Tetrazole | 70/105/210 | 40/60/120 µL | 60 sec | 180 min | 360 sec |
| Acetic Anhydride | 265/265/265 | 50/50/50 µL | 10 sec | 10 sec | 10 sec |
| N-Methyl Imidazole | 502/502/502 | 50/50/50 µL | 10 sec | 10 sec | 10 sec |
| TCA | 238/475/475 | 250/500/500 µL | 15 sec | 15 sec | 15 sec |
| Iodine | 6.8/6.8/6.8 | 80/80/80 µL | 30 sec | 30 sec | 30 sec |
| Beaucage | 34/51/51 | 80/120/120 | 100 sec | 200 sec | 200 sec |
| Acetonitrile | NA | 1150/1150/1150 µL | NA | NA | NA |

Wait time does not include contact time during delivery.
Tandem synthesis utilizes double coupling of linker molecule

TABLE III

Standard curve data for sense or antisense strand of siNA duplex in presence of tissue homogenates
Four Parameter Logistic Regression

| Standard Run ID | Line Equation | | | | Correlation Coefficient |
|---|---|---|---|---|---|
| SS107-118RCL | A = 0.008 | B = 1.036 | C = 1.176 | D = 3.620 | 1 |
| SA107-11SRCL | A = −0.002 | B = 1.006 | C = 0.941 | D = 2.951 | 1 |
| SS125-142RCL | A = 0.012 | B = 1.045 | C = 1.148 | D = 3.844 | 1 |
| SA125-142RCL | A = 0.012 | B = 1.007 | C = 1.187 | D = 3.164 | 1 |
| SS107-118VL | A = 0.028 | B = 1.111 | C = 0.935 | D = 3.830 | 1 |
| SS119-124VL | A = 0.0003 | B = 1.020 | C = 1.069 | D = 3.732 | 1 |
| SA107-118VL | A = 0.022 | B = 1.113 | C = 0.86 | D = 3.726 | 1 |
| SA119-124VL | A = −0.010 | B = 1.057 | C = 0.879 | D = 3.748 | 1 |
| SS125-142VL | A = −0.023 | B = 0.968 | C = 1.385 | D = 4.051 | 1 |
| SA125-142VL | A = −0.020 | B = 0.981 | C = 1.173 | D = 3.907 | 1 |
| SS107-118VR | A = −0.014 | B = 1.025 | C = 0.91 | D = 3.506 | 1 |
| SS119-124VR | A = −0.0001 | B = 0.977 | C = 1.544 | D = 3.528 | 1 |
| SA107-118VR | A = −0.013 | B = 1.047 | C = 0.841 | D = 3.495 | 1 |
| SA119-124VR | A = 0.0009 | B = 1.011 | C = 1.054 | D = 3.344 | 1 |
| SS125-142VR | A = −0.008 | B = 1.059 | C = 1.38 | D = 3.458 | 1 |
| SA125-142VR | A = −0.011 | B = 1.044 | C = 1.061 | D = 3.554 | 1 |
| SS142-125 P | A = 0.026 | B = 1.053 | C = 1.093 | D = 3.710 | 1 |
| SA142-125 P | A = 0.002 | B = 1.031 | C = 0.883 | D = 3.720 | 1 |
| | Average correlation coefficient | | | | 1 |

A Expected response at zero concentration.
B Slope factor.
C Expected concentration at midpoint (ED50).
D Expected response at infinite concentration.

TABLE IV

Back calculated calibration standard concentration (ng/mL) data for the sense strand of siNA duplex by hybridization-ELISA
Four Parameter Logistic Regression

| Sample ID | std 1 | std 2 | std 3 | std 4 | std 5 | std 6 | std 7 | std 8 | std 9 | std 10 | std 11 |
|---|---|---|---|---|---|---|---|---|---|---|---|
| SS107-118RCL | 14.78 | 6.89 | 3.62 | 1.74 | 0.87 | 0.44 | 0.23 | 0.11 | 0.056 | 0.028 | 0.013 |
| SS125-142RCL | 15.21 | 7.20 | 3.55 | 1.77 | 0.89 | 0.43 | 0.22 | 0.11 | 0.053 | 0.030 | 0.012 |
| SS107-118VL | 13.11 | 6.94 | 3.77 | 1.79 | 0.83 | 0.44 | 0.23 | 0.12 | 0.058 | 0.024 | 0.007 |
| SS119-124VL | 12.40 | 7.28 | 3.91 | 1.62 | 0.88 | 0.45 | 0.22 | 0.11 | 0.049 | 0.028 | 0.013 |
| SS125-142VL | 15.71 | 6.99 | 3.57 | 1.74 | 0.97 | 0.44 | 0.21 | 0.11 | 0.053 | 0.031 | 0.018 |
| SS107-118VR | 13.46 | 7.11 | 3.64 | 1.71 | 0.88 | 0.44 | 0.22 | 0.11 | 0.052 | 0.028 | 0.015 |
| SS119-124VR | 14.24 | 6.88 | 3.70 | 1.74 | 0.90 | 0.44 | 0.23 | 0.10 | 0.059 | 0.028 | 0.013 |
| SS125-142VR | 14.49 | 7.06 | 3.38 | 1.85 | 0.86 | 0.45 | 0.21 | 0.11 | 0.056 | 0.031 | 0.013 |
| SS142-125 P | 12.95 | 7.73 | 3.67 | 1.73 | 0.86 | 0.42 | 0.24 | 0.12 | 0.054 | 0.023 | 0.009 |
| N | 9 | 9 | 9 | 9 | 9 | 9 | 9 | 9 | 9 | 9 | 9 |
| Theoretical Concentration | 14 | 7.01 | 3.51 | 1.75 | 0.88 | 0.44 | 0.22 | 0.11 | 0.05 | 0.027 | 0.01 |
| Mean | 14.04 | 7.12 | 3.65 | 1.74 | 0.88 | 0.44 | 0.22 | 0.11 | 0.05 | 0.03 | 0.01 |
| SD | 1.12 | 0.27 | 0.15 | 0.06 | 0.04 | 0.01 | 0.01 | 0.01 | 0 | 0.003 | 0 |
| % C.V. | 7.97 | 3.74 | 4.03 | 3.54 | 4.42 | 1.79 | 3.89 | 4.78 | 5.71 | 10.4 | 6.3 |
| % Difference from theoretical | 0.08 | 1.51 | 3.95 | −0.6 | 0.58 | −0 | 2.13 | 0.33 | −1.24 | 0.588 | −10.4 |

TABLE V

Back calculated calibration standard concentration (ng/mL) data for the antisense strand of siNA duplex by hybridization-ELISA
Four Parameter Logistic Regression

| | Standard Run ID | | | | | | | | | | |
|---|---|---|---|---|---|---|---|---|---|---|---|
| | std 1 | std 2 | std 3 | std 4 | std 5 | std 6 | std 7 | std 8 | std 9 | std 10 | std 11 |
| SA107-118RCL | 16.90 | 6.65 | 3.47 | 1.61 | 0.86 | 0.41 | 0.20 | 0.11 | 0.055 | 0.030 | 0.009 |
| SA125-142RCL | 13.24 | 6.90 | 3.51 | 1.59 | 0.84 | 0.44 | 0.21 | 0.10 | 0.047 | 0.022 | 0.021 |
| SA107-118VL | 17.68 | 6.01 | 3.28 | 1.75 | 0.83 | 0.40 | 0.22 | 0.11 | 0.052 | 0.022 | 0.011 |
| SA119-124VL | 16.57 | 5.61 | 3.51 | 1.69 | 0.83 | 0.42 | 0.21 | 0.10 | 0.050 | 0.027 | 0.014 |
| SA125-142VL | 13.52 | 7.15 | 3.35 | 1.62 | 0.91 | 0.42 | 0.21 | 0.10 | 0.051 | 0.027 | 0.017 |
| SA107-118VR | 16.47 | 6.72 | 3.22 | 1.71 | 0.83 | 0.42 | 0.21 | 0.10 | 0.054 | 0.025 | 0.015 |
| SA119-124VR | 13.26 | 6.85 | 3.43 | 1.73 | 0.80 | 0.42 | 0.22 | 0.11 | 0.055 | 0.023 | 0.010 |
| SA125-142VR | 12.99 | 8.06 | 3.32 | 1.63 | 0.87 | 0.43 | 0.20 | 0.10 | 0.051 | 0.026 | 0.017 |
| SA142-125 P | 13.56 | 6.60 | 3.36 | 1.65 | 0.84 | 0.42 | 0.20 | 0.11 | 0.053 | 0.027 | 0.012 |
| N | 9 | 9 | 9 | 9 | 9 | 9 | 9 | 9 | 9 | 9 | 9 |
| Theoretical concentration | 13.3 | 6.7 | 3.3 | 1.7 | 0.8 | 0.4 | 0.2 | 0.1 | 0.05 | 0.03 | 0.01 |
| Mean | 14.91 | 6.73 | 3.38 | 1.66 | 0.85 | 0.42 | 0.21 | 0.11 | 0.05 | 0.03 | 0.01 |
| SD | 1.93 | 0.7 | 0.1 | 0.1 | 0 | 0 | 0 | 0 | 0 | 0 | 0 |
| % C.V. | 12.9 | 10 | 3.1 | 3.5 | 3.6 | 2.7 | 3.6 | 3.1 | 4.99 | 10.7 | 7.3 |
| % Difference from theoretical | 11.9 | 1 | 1.6 | −0 | 1.6 | 0.4 | −0.5 | 1.1 | −0.43 | −3.31 | 5.87 |

TABLE VI

Quality control (QC) data for antisense strand of siNA duplex
The QC samples were prepared similar to that of standards by two-fold dilution of siNA duplex in 1M GITC buffer in presence of tissue homogenates.

| Run ID | QC1 | QC2 | QC3 | QC4 |
|---|---|---|---|---|
| SA107-118RCL | 1.606 | 0.768 | | 0.189 |
| SA125-142RCL | 1.672 | 0.805 | | 0.181 |
| SA107-118VL | 1.604 | 0.797 | | 0.225 |
| SA119-124VL | 1.541 | 0.737 | | 0.183 |
| SA125-142VL | 1.879 | 0.977 | | 0.238 |
| SA107-118VR | 1.335 | 0.677 | | 0.183 |
| SA119-124VR | 1.831 | 0.760 | | 0.248 |
| SA125-142VR | 1.049 | 0.573 | | 0.167 |
| SA142-125 P | 1.521 | | 0.385 | |
| N | 9 | 8 | 1 | 8 |
| Theoretical value | 1.665 | 0.832 | 0.416 | 0.208 |
| Mean | 1.56 | 0.762 | | 0.202 |
| SD | 0.251 | 0.115 | | 0.030 |
| % C.V. | 16.12 | 15.12 | | 15.10 |
| % Difference from theoretical | −6.33 | −8.44 | | −3.00 |

TABLE VII

Quality control (QC) data for sense strand of siNA duplex
The QC samples were prepared similar to standards by two-fold dilution of siNA duplex in 1M GITC buffer in presence of tissue homogenates.

| Run ID | QC1 | QC2 | QC3 | QC4 |
|---|---|---|---|---|
| SS107-118RCL | 1.552 | 0.827 | | 0.222 |
| SS125-142RCL | 1.696 | 1.011 | | 0.226 |
| SS107-118VL | 1.473 | 0.732 | | 0.193 |
| SS119-124VL | 1.465 | 0.682 | | 0.154 |
| SS125-142VL | 1.873 | 0.976 | | 0.230 |
| SS107-118VR | 1.442 | 0.848 | | 0.361 |
| SS119-124VR | 1.818 | 0.819 | | 0.209 |
| SS125-142VR | 1.306 | 0.664 | | 0.169 |
| SS142-125 P | 1.752 | | 0.372 | |
| N | 9 | 8 | 1 | 8 |
| Theoretical value | 1.750 | 0.880 | 0.44 | 0.220 |
| Mean | 1.597 | 0.820 | | 0.221 |
| SD | 0.194 | 0.127 | | 0.063 |
| % C.V. | 12.17 | 15.48 | | 28.59 |
| % Difference from theoretical | −8.72 | −6.83 | | 0.227 |

TABLE VIII siNA duplex concentration data (vitreous from left eye)
The total concentrations of sense and antisense strands of siNA duplex found in vitreous from the left eye of rabbits administered single bilateral intravitreal injections of 0.5 mg/eye siNA duplex. The amount of duplex was estimated by doubling the smaller value for sense or antisense strand.

| | Time | | Concentration µg/mL | | Estimated duplex |
|---|---|---|---|---|---|
| Sample # | Days | Hours | Sense | Antisense | µg/mL |
| 107 | 13 | 0 | 0.006 | 0.007 | 0.0112 |
| 108 | 13 | 0 | 0.003 | 0.005 | 0.0064 |
| 109 | 13 | 0 | 0.001 | 0.002 | 0.0026 |
| 110 | 11 | 0 | 0.005 | 0.004 | 0.0094 |
| 111 | 11 | 0 | 0.002 | 0.002 | 0.004 |
| 112 | 11 | 0 | <0.001 | <0.001 | <0.002 |
| 113 | 9 | 0 | 0.104 | 0.170 | 0.2071 |
| 114 | 9 | 0 | 0.055 | 0.053 | 0.1068 |
| 115 | 9 | 0 | 0.109 | 0.186 | 0.2177 |
| 116 | 7 | 0 | 1.40 | 1.24 | 2.47 |
| 117 | 7 | 0 | 1.86 | 1.88 | 3.72 |
| 118 | 7 | 0 | 0.090 | 0.10 | 0.1757 |
| 119 | 5 | 0 | 9.1 | 14.2 | 18.27 |
| 120 | 5 | 0 | 7.4 | 8.1 | 14.8 |
| 121 | 5 | 0 | 12.9 | 14.9 | 25.89 |
| 122 | 4 | 0 | 23.5 | 34.2 | 46.96 |
| 123 | 4 | 0 | 18.2 | 23.5 | 36.37 |
| 124 | 4 | 0 | 21.7 | 35.5 | 43.43 |
| 125 | 3 | 0 | 64.7 | 60.5 | 120.9 |
| 126 | 3 | 0 | 69.8 | 61.7 | 123.3 |

TABLE VIII-continued siNA duplex concentration data (vitreous from left eye)
The total concentrations of sense and antisense strands of siNA duplex found in vitreous from the left eye of rabbits administered single bilateral intravitreal injections of 0.5 mg/eye siNA duplex. The amount of duplex was estimated by doubling the smaller value for sense or antisense strand.

| Sample # | Time Days | Time Hours | Concentration μg/mL Sense | Concentration μg/mL Antisense | Estimated duplex μg/mL |
|---|---|---|---|---|---|
| 127 | 3 | 0 | 78.5 | 70.2 | 140.4 |
| 128 | 2 | 0 | 125.4 | 117.0 | 234 |
| 129 | 2 | 0 | 134.0 | 135.9 | 267.9 |
| 130 | 2 | 0 | 128.7 | 128.6 | 257.1 |
| 131 | 1 | 0 | 205.8 | 201.0 | 402 |
| 132 | 1 | 0 | 184.2 | 191.3 | 368.4 |
| 133 | 1 | 0 | 227.6 | 250.2 | 455.1 |
| 134 | 0 | 8 | 278.9 | 311.4 | 557.7 |
| 135 | 0 | 8 | 359.0 | 374.6 | 717.9 |
| 136 | 0 | 8 | 290.3 | 336.3 | 580.5 |
| 137 | 0 | 4 | 260.3 | 246.5 | 492.9 |
| 138 | 0 | 4 | 255.2 | 250.1 | 500.1 |
| 139 | 0 | 4 | 288.6 | 289.5 | 577.2 |
| 171 | 0 | 4 | 265.8 | 300.6 | 531.6 |
| 140 | 0 | 1 | 256.4 | 241.1 | 482.1 |
| 141 | 0 | 1 | 282.6 | 264.5 | 528.9 |
| 142 | 0 | 1 | 283.2 | 276.2 | 552.3 |
| 172 | 0 | 1 | 253.0 | 239.8 | 479.7 |

TABLE IX siNA duplex concentration data (vitreous from right eye)
The total concentrations of sense and antisense strands of siNA duplex found in vitreous from the right eye of rabbits administered single bilateral intravitreal injections of 0.5 mg/eye siNA duplex. The amount of duplex was estimated by doubling the smaller value for sense or antisense strand.

| Sample # | Time Days | Time Hours | Concentration μg/mL Sense | Concentration μg/mL Antisense | Estimated duplex μg/mL |
|---|---|---|---|---|---|
| 107 | 13 | 0 | 0.0037 | 0.0044 | 0.0073 |
| 108 | 13 | 0 | 0.0017 | 0.0017 | 0.0033 |
| 109 | 13 | 0 | 0.0010 | 0.0012 | 0.002 |
| 110 | 11 | 0 | 0.0096 | 0.0090 | 0.018 |
| 111 | 11 | 0 | 0.0146 | 0.0192 | 0.0292 |
| 112 | 11 | 0 | 0.0013 | 0.0014 | 0.0026 |
| 113 | 9 | 0 | 0.0318 | 0.0310 | 0.062 |
| 114 | 9 | 0 | 0.1109 | 0.1326 | 0.2218 |
| 115 | 9 | 0 | 0.229 | 0.479 | 0.4581 |
| 116 | 7 | 0 | 1.43 | 1.30 | 2.59 |
| 117 | 7 | 0 | 2.43 | 1.23 | 2.46 |
| 118 | 7 | 0 | 0.20 | 0.16 | 0.3119 |
| 119 | 5 | 0 | 7.3 | 8.7 | 14.54 |
| 120 | 5 | 0 | 11.4 | 14.5 | 22.83 |
| 121 | 5 | 0 | 14.3 | 13.2 | 26.47 |
| 122 | 4 | 0 | 35.9 | 86.1 | 71.72 |
| 123 | 4 | 0 | 23.6 | 38.0 | 47.11 |
| 124 | 4 | 0 | 30.9 | 62.9 | 61.78 |
| 125 | 3 | 0 | 52.2 | 57.3 | 104.4 |
| 126 | 3 | 0 | 61.2 | 62.4 | 122.4 |
| 127 | 3 | 0 | 60.5 | 56.6 | 113.1 |
| 128 | 2 | 0 | 107.1 | 104.0 | 207.9 |
| 129 | 2 | 0 | 97.8 | 99.3 | 195.6 |
| 130 | 2 | 0 | 93.2 | 90.3 | 180.6 |
| 131 | 1 | 0 | 125.6 | 119.3 | 238.5 |
| 132 | 1 | 0 | 48.9 | 46.4 | 92.7 |
| 133 | 1 | 0 | 155.9 | 149.0 | 297.9 |
| 134 | 0 | 8 | 183.6 | 165.6 | 331.2 |
| 135 | 0 | 8 | 202.5 | 188.7 | 377.4 |
| 136 | 0 | 8 | 183.3 | 183.6 | 366.6 |
| 137 | 0 | 4 | 187.5 | 197.4 | 375.0 |
| 138 | 0 | 4 | 212.0 | 198.9 | 397.8 |
| 139 | 0 | 4 | 213.3 | 179.4 | 358.8 |

TABLE IX-continued siNA duplex concentration data (vitreous from right eye)
The total concentrations of sense and antisense strands of siNA duplex found in vitreous from the right eye of rabbits administered single bilateral intravitreal injections of 0.5 mg/eye siNA duplex. The amount of duplex was estimated by doubling the smaller value for sense or antisense strand.

| Sample # | Time Days | Time Hours | Concentration μg/mL Sense | Concentration μg/mL Antisense | Estimated duplex μg/mL |
|---|---|---|---|---|---|
| 171 | 0 | 4 | 177.15 | 144.9 | 289.8 |
| 140 | 0 | 1 | 183.3 | 169.4 | 338.7 |
| 141 | 0 | 1 | 190.2 | 168.6 | 337.2 |
| 142 | 0 | 1 | 179.4 | 140.7 | 281.4 |
| 172 | 0 | 1 | 162.15 | 134.9 | 269.7 |

TABLE X siNA duplex concentration data (retina-choroid from left eye)
The total concentrations of sense and antisense strands of siNA duplex found in retina-choroid from left eye of rabbits administered single bilateral intravitreal injections of 0.5 mg/eye siNA duplex. The amount of duplex was estimated by doubling the smaller value for sense or antisense strand.

| Sample # | Time Days | Time Hours | Concentration ng/mg Sense | Concentration ng/mg Antisense | Estimated duplex ng/mg |
|---|---|---|---|---|---|
| 107 | 13 | 0 | <0.015 | <0.015 | <0.030 |
| 108 | 13 | 0 | <0.015 | <0.015 | <0.031 |
| 109 | 13 | 0 | <0.015 | <0.015 | <0.032 |
| 110 | 11 | 0 | <0.015 | <0.015 | <0.033 |
| 111 | 11 | 0 | <0.015 | <0.015 | <0.034 |
| 112 | 11 | 0 | <0.015 | <0.015 | <0.035 |
| 113 | 9 | 0 | 0.0340 | 0.0280 | 0.056 |
| 114 | 9 | 0 | 0.0080 | 0.0020 | 0.004 |
| 115 | 9 | 0 | 0.036 | 0.027 | 0.053 |
| 116 | 7 | 0 | 0.35 | 0.23 | 0.46 |
| 117 | 7 | 0 | 0.60 | 0.56 | 1.115 |
| 118 | 7 | 0 | 0.06 | 0.04 | 0.076 |
| 119 | 5 | 0 | 2.5 | 2.0 | 4.05 |
| 120 | 5 | 0 | 1.8 | 1.2 | 2.43 |
| 121 | 5 | 0 | 3.6 | 3.0 | 6.01 |
| 122 | 4 | 0 | 5.8 | 5.5 | 11.04 |
| 123 | 4 | 0 | 4.2 | 3.6 | 7.22 |
| 124 | 4 | 0 | 7.4 | 7.7 | 14.80 |
| 125 | 3 | 0 | 19.4 | 17.2 | 34.3 |
| 126 | 3 | 0 | 17.4 | 11.8 | 23.6 |
| 127 | 3 | 0 | 15.9 | 12.4 | 24.7 |
| 128 | 2 | 0 | 25.1 | 21.4 | 42.8 |
| 129 | 2 | 0 | 30.3 | 33.5 | 60.5 |
| 130 | 2 | 0 | 25.4 | 26.4 | 50.7 |
| 131 | 1 | 0 | 44.2 | 54.0 | 88.4 |
| 132 | 1 | 0 | 35.9 | 48.5 | 71.7 |
| 133 | 1 | 0 | 37.9 | 46.5 | 75.8 |
| 134 | 0 | 8 | 94.6 | 135.0 | 189.1 |
| 135 | 0 | 8 | 63.3 | 78.4 | 126.6 |
| 136 | 0 | 8 | 103.6 | 128.6 | 207.1 |
| 137 | 0 | 4 | 47.2 | 47.5 | 94.4 |
| 138 | 0 | 4 | 55.6 | 47.4 | 94.8 |
| 139 | 0 | 4 | 98.8 | 111.0 | 197.6 |
| 140 | 0 | 1 | 53.9 | 53.0 | 106.0 |
| 141 | 0 | 1 | 76.4 | 79.4 | 152.7 |
| 142 | 0 | 1 | 82.4 | 83.0 | 164.8 |

TABLE XI siNA duplex and assay polynucleotide sequences

| Name | Compound Number | Sequence | SEQ ID NO: |
|---|---|---|---|
| Sense Strand | 31270 | B CUGAGUUUAAAAGGCACCCTT B | 19 |
| Antisense strand | 31273 | GGGUGCCUUUUAAACUCAGTsT | 20 |
| Capture probe for Sense strand #31270 | 33041 | 5' cuuuuaaacucag b | 21 |
| Reporter probe for Sense strand #31270 | 33042 | 5' F aagggugcc | 22 |
| Capture probe for Antisense strand #31273 | 34015 | 5' b uacugaguuuaaaa | 23 |
| Reporter probe for Antisense strand #31273 | 34016 | 5' ggcaccca F | 24 |

B = inverted deoxyabasic
S = phosphorothioate
Upper case (A, G, C, U) = ribonucleotide
Lower case (a, g, c, u) = 2'-O-methyl
b = biotin
F = fluorescein

---

What we claim is:

1. A method for determining the concentration of a double stranded nucleic acid molecule in a biological sample, comprising:
   (a) obtaining a biological sample from a subject;
   (b) assaying a first portion of the sample for the concentration of any unhybridized single stranded component of the double stranded nucleic acid molecule under conditions suitable to determine the concentration of the unhybridized single stranded component in the sample;
   (c) processing a second portion of the sample under conditions suitable for any double stranded nucleic acid molecule present in the sample to disassociate into one or more single stranded components;
   (d) assaying the second portion for the concentration of any disassociated single stranded component of the double stranded nucleic acid molecule under conditions suitable to determine the concentration of the disassociated single stranded component in the sample; and
   (e) comparing the concentration of the unhybridized single stranded component to the concentration of the disassociated single stranded component under conditions suitable to determine the concentration of the double stranded nucleic acid molecule in the sample.

2. The method of claim 1, wherein the processing in (c) comprises heating the second portion at about 85 to about 95 degrees C. for about 5 to about 30 minutes.

3. The method of claim 1, wherein the assaying in (b) comprises:
   (i) combining the first portion of the sample with a capture oligonucleotide affixed to a surface under conditions suitable for the capture oligonucleotide to specifically hybridize with a first portion of the unhybridized single stranded component;
   (ii) washing the surface under conditions suitable to remove any unbound portion of the double stranded nucleic acid molecule;
   (iii) adding a detection oligonucleotide to the surface of (ii) under conditions suitable for the detection oligonucleotide to specifically hybridize with a second portion of the unhybridized single stranded component;
(iv) washing the surface under conditions suitable to remove any unbound detection oligonucleotide;
(v) adding a reporter molecule to the surface of (iv);
(vi) washing the surface under conditions suitable to remove any unbound or unreacted reporter molecule;
(vii) measuring the amount of the bound or reacted reporter molecule; and
(viii) determining the concentration of the unhybridized single stranded component by comparing the amount of the reporter molecule with a standard curve.

4. The method of claim 1, wherein the assaying in (b) comprises:
(i) combining the first portion of the sample with a detection oligonucleotide under conditions suitable for the detection oligonucleotide to specifically hybridize with a first portion of the unhybridized single stranded component;
(ii) combining the product of (i) with a capture oligonucleotide affixed to a surface under conditions suitable for the capture oligonucleotide to specifically hybridize with a second portion of the unhybridized single stranded component;
(iii) washing the surface under conditions suitable to remove any unbound detection oligonucleotide complex;
(iv) adding a reporter molecule to the surface of (iii);
(v) washing the surface under conditions suitable to remove any unbound or unreacted reporter molecule;
(vi) measuring the amount of the bound or reacted reporter molecule; and
(vii) determining the concentration of the unhybridized single stranded by comparing the amount of the reporter molecule with a standard curve.

5. The method of claim 1, wherein the assaying in (d) comprises:
(i) combining the second portion of the sample with a capture oligonucleotide affixed to a surface under conditions suitable for the capture oligonucleotide to specifically hybridize with a first portion of the disassociated single stranded component;
(ii) washing the surface under conditions suitable to remove any unbound portion of the double stranded nucleic acid molecule;
(iii) adding a detection oligonucleotide to the surface of (ii) under conditions suitable for the detection oligonucleotide to specifically hybridize with a second portion of the disassociated single stranded component;
(iv) washing the surface under conditions suitable to remove any unbound detection oligonucleotide;
(v) adding a reporter molecule to the surface of (iv);
(vi) washing the surface under conditions suitable to remove any unbound or unreacted reporter molecule;
(vii) measuring the amount of the bound or reacted reporter molecule; and
(viii) determining the concentration of the disassociated single stranded component by comparing the amount of the reporter molecule with a standard curve.

6. The method of claim 1, wherein the assaying in (d) comprises:
(i) combining the second portion of the sample with a detection oligonucleotide under conditions suitable for the detection oligonucleotide to specifically hybridize with a first portion of the disassociated single stranded component;
(ii) combining the product of (i) with a capture oligonucleotide affixed to a surface under conditions suitable for the capture oligonucleotide to specifically hybridize with a second portion of the disassociated single stranded component;
(iii) washing the surface under conditions suitable to remove any unbound detection oligonucleotide complex;
(iv) adding a reporter molecule to the surface of (iii);
(v) washing the surface under conditions suitable to remove any unbound or unreacted reporter molecule;
(vi) measuring the amount of the bound or reacted reporter molecule; and
(vii) determining the concentration of the disassociated single stranded component by comparing the amount of the reporter molecule with a standard curve.

7. The method of claim 1, wherein (c) further comprises removing any single stranded component of the double stranded nucleic acid molecule from the sample that can competitively bind to the other single stranded component of the double stranded nucleic acid molecule.

8. The method of claim 7, wherein (c) comprises:
(i) heating the sample to about 90 degrees C. for about 10 minutes;
(ii) treating the sample with a streptavidin conjugated complementary oligonucleotide sequence that binds to the single stranded component; and
(iii) removing the single stranded component from the assay.

9. The method of claim 1, wherein the double stranded nucleic acid molecule comprises a nucleic acid molecule that mediates RNA interference.

10. The method of claim 3, wherein the nucleic acid molecule that mediates RNA interference is a short interfering nucleic acid molecule (siNA).

11. The method of claim 9, wherein the double stranded nucleic acid molecule comprises a nucleic acid molecule that mediates RNA interference against VEGF RNA.

12. The method of claim 9, wherein the double stranded nucleic acid molecule comprises a nucleic acid molecule that mediates RNA interference against VEGFR1 RNA.

13. The method of claim 9, wherein the double stranded nucleic acid molecule comprises a nucleic acid molecule that mediates RNA interference against VEGFR2 RNA.

14. The method of claim 9, wherein the double stranded nucleic acid molecule comprises a nucleic acid molecule that mediates RNA interference against Hepatitis C Virus (HCV) RNA.

15. The method of claim 9, wherein the double stranded nucleic acid molecule comprises a nucleic acid molecule that mediates RNA interference against Hepatitis C Virus (HBV) RNA.

16. The method of claim 9, wherein the double stranded nucleic acid molecule comprises a nucleic acid molecule that mediates RNA interference against HIV RNA.

17. The method of claim 10, wherein the siNA comprises one or more 2'-deoxy-2'-fluoro nucleotides.

18. The method of claim 10, wherein the siNA comprises one or more 2'-O-methyl nucleotides.

19. The method of claim 10, wherein the siNA comprises one or more inverted deoxyabasic moieties.

20. The method of claim 10, wherein the siNA comprises one or more 2'-deoxy nucleotides.

* * * * *

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: siNA sense
      region
<220> FEATURE:
<221> NAME/KEY: misc_feature
<222> LOCATION: (1)..(1)
<223> OTHER INFORMATION: 5'-3 attached terminal deoxyabasic moeity
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (7)..(10)
<223> OTHER INFORMATION: 2'-deoxy-2'-fluoro
<220> FEATURE:
<221> NAME/KEY: misc_feature
<222> LOCATION: (12)..(15)
<223> OTHER INFORMATION: 2'-deoxy-2'-fluoro
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moeity

<400> SEQUENCE: 1
ugugcacuuc gcuucaccut t                                              21

```
<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:
      Chol-7/siNA sense region
<220> FEATURE:
<221> NAME/KEY: misc_feature
<222> LOCATION: (1)..(1)
<223> OTHER INFORMATION: 5'bifunctional cholesterol conjugate
<220> FEATURE:
<221> NAME/KEY: misc_feature
<222> LOCATION: (3)..(3)
<223> OTHER INFORMATION: inverted deoxyabasic moeity
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (9)..(12)
<223> OTHER INFORMATION: 2'-deoxy-2'-fluoro
<220> FEATURE:
<221> NAME/KEY: misc_feature
<222> LOCATION: (14)..(17)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-deoxy-2'-fluoro
<220> FEATURE:
<221> NAME/KEY: misc_feature
<222> LOCATION: (1)..(21)
<223> OTHER INFORMATION: ribonucleotide modified as described
<220> FEATURE:
<221> NAME/KEY: misc_feature
<222> LOCATION: (23)..(23)
<223> OTHER INFORMATION: 3'-3 attached terminal deoxyabasic moeity

<400> SEQUENCE: 2
taugugcacu ucgcuucacc utt                                          23

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:
      Chol-trigal 7/siNA sense region
<220> FEATURE:
<221> NAME/KEY: misc_feature
<222> LOCATION: (1)..(1)
<223> OTHER INFORMATION: 5'bifunctional cholesterol conjugate
<220> FEATURE:
<221> NAME/KEY: misc_feature
<222> LOCATION: (3)..(3)
<223> OTHER INFORMATION: inverted deoxyabasic moeity
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
```

```
<222> LOCATION: (7)..(7)
<223> OTHER INFORMATION: 2'-deoxy-2'-fluoro
<220> FEATURE:
<221> NAME/KEY: misc_feature
<222> LOCATION: (9)..(12)
<223> OTHER INFORMATION: 2'-deoxy-2'-fluoro
<220> FEATURE:
<221> NAME/KEY: misc_feature
<222> LOCATION: (14)..(17)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-deoxy-2'-fluoro
<220> FEATURE:
<221> NAME/KEY: misc_feature
<222> LOCATION: (23)..(23)
<223> OTHER INFORMATION: 3' inverted deoxyabasic moeity
<220> FEATURE:
<221> NAME/KEY: misc_feature
<222> LOCATION: (24)..(24)
<223> OTHER INFORMATION: 2'-deoxy-2'-fluoro
<220> FEATURE:
<221> NAME/KEY: misc_feature
<222> LOCATION: (2)..(21)
<223> OTHER INFORMATION: ribonucleotide modified as described
<220> FEATURE:
<221> NAME/KEY: misc_feature
<222> LOCATION: (24)..(24)
<223> OTHER INFORMATION: ribonucleotide modified as described
<220> FEATURE:
<221> NAME/KEY: misc_feature
<222> LOCATION: (25)..(25)
<223> OTHER INFORMATION: 3' tri-N-acetyl galactosamine conjugate
<220> FEATURE:
<221> NAME/KEY: misc_feature
<222> LOCATION: (25)..(25)
<223> OTHER INFORMATION: 3'-3 attached terminal deoxyabasic moeity

<400> SEQUENCE: 3
taugugcacu ucgcuucacc uttat                                           25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:  siNA
      antisense region
<220> FEATURE:
<221> NAME/KEY: misc_feature
<222> LOCATION: (1)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
```

```
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 4
aggugaagcg aagugcacat t                                              21

<210> SEQ ID NO 5
<211> LENGTH: 10
<212> TYPE: RNA
<213> ORGANISM: Artificial Sequence
<220> FEATURE:
<223> OTHER INFORMATION: Description of Artificial Sequence: Biotinyl
      capture oligo/siNA sense region
<220> FEATURE:
<221> NAME/KEY: misc_feature
<222> LOCATION: (1)..(1)
<223> OTHER INFORMATION: 5' attached terminal Biotin
<220> FEATURE:
<221> NAME/KEY: misc_feature
<222> LOCATION: (1)..(10)
<223> OTHER INFORMATION: 2'-O-methyl

<400> SEQUENCE: 5
aggugaagcg                                                           10

<210> SEQ ID NO 6
<211> LENGTH: 10
<212> TYPE: RNA
<213> ORGANISM: Artificial Sequence
<220> FEATURE:
<223> OTHER INFORMATION: Description of Artificial Sequence: Biotinyl
      capture oligo/siNA antisense region
<220> FEATURE:
<221> NAME/KEY: misc_feature
<222> LOCATION: (1)..(1)
<223> OTHER INFORMATION: 5'attached terminal Biotin
<220> FEATURE:
<221> NAME/KEY: misc_feature
<222> LOCATION: (1)..(10)
<223> OTHER INFORMATION: 2'-O-methyl

<400> SEQUENCE: 6
ugugcacuuc                                                           10

<210> SEQ ID NO 7
<211> LENGTH: 11
<212> TYPE: RNA
<213> ORGANISM: Artificial Sequence
<220> FEATURE:
<223> OTHER INFORMATION: Description of Artificial Sequence: FITC
      labeled reporter oligo/siNA sense region
```

```
<220> FEATURE:
<221> NAME/KEY: misc_feature
<222> LOCATION: (1)..(11)
<223> OTHER INFORMATION: 2'-O-methyl
<220> FEATURE:
<221> NAME/KEY: misc_feature
<222> LOCATION: (11)..(11)
<223> OTHER INFORMATION: 3' attached terminal Fluorescein

<400> SEQUENCE: 7
aagugcacau u                                                              11

<210> SEQ ID NO 8
<211> LENGTH: 11
<212> TYPE: RNA
<213> ORGANISM: Artificial Sequence
<220> FEATURE:
<223> OTHER INFORMATION: Description of Artificial Sequence:  FITC
      labeled reporter oligo/siNA antisense region
<220> FEATURE:
<221> NAME/KEY: misc_feature
<222> LOCATION: (1)..(11)
<223> OTHER INFORMATION: 2'-O-methyl
<220> FEATURE:
<221> NAME/KEY: misc_feature
<222> LOCATION: (11)..(11)
<223> OTHER INFORMATION: 3' attached terminal Fluorescein

<400> SEQUENCE: 8
gcuucaccuu u                                                              11

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:  siNA sense
      region
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (6)..(9)
<223> OTHER INFORMATION: 2'-deoxy-2'-fluoro
<220> FEATURE:
<221> NAME/KEY: misc_feature
<222> LOCATION: (11)..(14)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: 2'-deoxy-2'-fluoro
<220> FEATURE:
<221> NAME/KEY: misc_feature
<222> LOCATION: (1)..(18)
<223> OTHER INFORMATION: ribonucleotide modified as described
<220> FEATURE:
<221> NAME/KEY: misc_feature
<222> LOCATION: (20)..(20)
<223> OTHER INFORMATION: 3'-3 attached terminal deoxyabasic moeity

<400> SEQUENCE: 9
gugcacuucg cuucaccutt                                                     20

<210> SEQ ID NO 10
<211> LENGTH: 19
<212> TYPE: DNA
```

```
<213> ORGANISM: Artificial Sequence
<220> FEATURE:
<223> OTHER INFORMATION: Description of Artificial Sequence:  siNA sense
      region
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(8)
<223> OTHER INFORMATION: 2'-deoxy-2'-fluoro
<220> FEATURE:
<221> NAME/KEY: misc_feature
<222> LOCATION: (10)..(13)
<223> OTHER INFORMATION: 2'-deoxy-2'-fluoro
<220> FEATURE:
<221> NAME/KEY: misc_feature
<222> LOCATION: (15)..(17)
<223> OTHER INFORMATION: 2'-deoxy-2'-fluoro
<220> FEATURE:
<221> NAME/KEY: misc_feature
<222> LOCATION: (1)..(17)
<223> OTHER INFORMATION: ribonucleotide modified as described
<220> FEATURE:
<221> NAME/KEY: misc_feature
<222> LOCATION: (19)..(19)
<223> OTHER INFORMATION: 3'-3 attached terminal deoxyabasic moeity

<400> SEQUENCE: 10
ugcacuucgc uucaccutt                                                    19

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:  siNA sense
      region
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(6)
<223> OTHER INFORMATION: 2'-deoxy-2'-fluoro
<220> FEATURE:
<221> NAME/KEY: misc_feature
<222> LOCATION: (8)..(11)
<223> OTHER INFORMATION: 2'-deoxy-2'-fluoro
<220> FEATURE:
<221> NAME/KEY: misc_feature
<222> LOCATION: (13)..(15)
<223> OTHER INFORMATION: 2'-deoxy-2'-fluoro
<220> FEATURE:
<221> NAME/KEY: misc_feature
<222> LOCATION: (1)..(15)
<223> OTHER INFORMATION: ribonucleotide modified as described
<220> FEATURE:
<221> NAME/KEY: misc_feature
<222> LOCATION: (17)..(17)
<223> OTHER INFORMATION: 3'-3 attached terminal deoxyabasic moeity

<400> SEQUENCE: 11
cacuucgcuu caccutt                                                      17

<210> SEQ ID NO 12
<211> LENGTH: 13
<212> TYPE: DNA
<213> ORGANISM: Artificial Sequence
```

```
<220> FEATURE:
<223> OTHER INFORMATION: Description of Artificial Sequence:  siNA sense
      region
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (4)..(7)
<223> OTHER INFORMATION: 2'-deoxy-2'-fluoro
<220> FEATURE:
<221> NAME/KEY: misc_feature
<222> LOCATION: (9)..(11)
<223> OTHER INFORMATION: 2'-deoxy-2'-fluoro
<220> FEATURE:
<221> NAME/KEY: misc_feature
<222> LOCATION: (1)..(11)
<223> OTHER INFORMATION: ribonucleotide modified as described
<220> FEATURE:
<221> NAME/KEY: misc_feature
<222> LOCATION: (13)..(13)
<223> OTHER INFORMATION: 3'-3 attached terminal deoxyabasic moeity

<400> SEQUENCE: 12
ucgcuucacc utt                                                          13

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:  siNA
      antisense region
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: Phosphorothioate 3'-Internucleotide Linkage
<220> FEATURE:
<221> NAME/KEY: misc_feature
<222> LOCATION: (1)..(18)
<223> OTHER INFORMATION: ribonucleotide modified as described

<400> SEQUENCE: 13
ggugaagcga agugcacatt                                                   20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:  siNA
      antisense region
<220> FEATURE:
<221> NAME/KEY: misc_feature
```

```
<222> LOCATION: (2)..(2)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: Phosphorothioate 3'-Internucleotide Linkage
<220> FEATURE:
<221> NAME/KEY: misc_feature
<222> LOCATION: (1)..(17)
<223> OTHER INFORMATION: ribonucleotide modified as described

<400> SEQUENCE: 14
gugaagcgaa gugcacatt                                                  19

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:  siNA
      antisense region
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: Phosphorothioate 3'-Internucleotide Linkage
<220> FEATURE:
<221> NAME/KEY: misc_feature
<222> LOCATION: (1)..(17)
<223> OTHER INFORMATION: ribonucleotide modified as described

<400> SEQUENCE: 15
gaagcgaagu gcacatt                                                    17

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence:  siNA
      antisense region
<220> FEATURE:
<221> NAME/KEY: misc_feature
<222> LOCATION: (3)..(3)
```

<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: Phosphorothioate 3'-Internucleotide Linkage
<220> FEATURE:
<221> NAME/KEY: misc_feature
<222> LOCATION: (1)..(13)
<223> OTHER INFORMATION: ribonucleotide modified as described

<400> SEQUENCE: 16
agcgaagugc acatt                                                       15

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:  siNA sense
      region
<220> FEATURE:
<221> NAME/KEY: misc_feature
<222> LOCATION: (1)..(1)
<223> OTHER INFORMATION: 5'-3 attached terminal deoxyabasic moeity
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-deoxy
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy
<220> FEATURE:

```
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moeity

<400> SEQUENCE: 17
ugugcacuuc gcuucaccut t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:  siNA
      antisense region
<220> FEATURE:
<221> NAME/KEY: misc_feature
<222> LOCATION: (1)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 18
```
aggugaagcg aaguagcacat t                                    21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:  siNA sense
      region
<220> FEATURE:
<221> NAME/KEY: misc_feature
<222> LOCATION: (1)..(1)
<223> OTHER INFORMATION: 5'-3 attached terminal deoxyabasic moeity
<220> FEATURE:
<221> NAME/KEY: misc_feature
<222> LOCATION: (1)..(19)
<223> OTHER INFORMATION: ribonucleotide modified as described
<220> FEATURE:
<221> NAME/KEY: misc_feature
<222> LOCATION: (21)..(21)
<223> OTHER INFORMATION: 3'-3 attached terminal deoxyabasic moeity

<400> SEQUENCE: 19
cugaguuuaa aaggcaccct t                                     21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:  siNA
      antisense region
<220> FEATURE:
<221> NAME/KEY: misc_feature
<222> LOCATION: (20)..(20)
<223> OTHER INFORMATION: Phosphorothioate 3'-Internucleotide Linkage
<220> FEATURE:
<221> NAME/KEY: misc_feature
<222> LOCATION: (1)..(19)
<223> OTHER INFORMATION: ribonucleotide modified as described

<400> SEQUENCE: 20
gggugccuuu uaaacucagt t                                     21

<210> SEQ ID NO 21
<211> LENGTH: 13
<212> TYPE: RNA
<213> ORGANISM: Artificial Sequence
<220> FEATURE:
<223> OTHER INFORMATION: Description of Artificial Sequence:  Capture
      probe/siNA sense region
<220> FEATURE:
<221> NAME/KEY: misc_feature
<222> LOCATION: (1)..(13)
<223> OTHER INFORMATION: 2'-O-methyl
<220> FEATURE:
<221> NAME/KEY: misc_feature
<222> LOCATION: (13)..(13)
<223> OTHER INFORMATION: 3' attached terminal Biotin

<400> SEQUENCE: 21
cuuuuaaacu cag                                              13

<210> SEQ ID NO 22
<211> LENGTH: 9
<212> TYPE: RNA
<213> ORGANISM: Artificial Sequence
<220> FEATURE:
<223> OTHER INFORMATION: Description of Artificial Sequence:  Reporter
      probe/siNA sense region
<220> FEATURE:
<221> NAME/KEY: misc_feature

```
<222> LOCATION: (1)..(1)
<223> OTHER INFORMATION: 5' attached terminal Fluorescein
<220> FEATURE:
<221> NAME/KEY: misc_feature
<222> LOCATION: (1)..(9)
<223> OTHER INFORMATION: 2'-O-methyl

<400> SEQUENCE: 22 aagggugcc                                                                 9

<210> SEQ ID NO 23
<211> LENGTH: 14
<212> TYPE: RNA
<213> ORGANISM: Artificial Sequence
<220> FEATURE:
<223> OTHER INFORMATION: Description of Artificial Sequence:  Capture
      probe/siNA antisense region
<220> FEATURE:
<221> NAME/KEY: misc_feature
<222> LOCATION: (1)..(1)
<223> OTHER INFORMATION: 5' attached terminal Biotin
<220> FEATURE:
<221> NAME/KEY: misc_feature
<222> LOCATION: (1)..(14)
<223> OTHER INFORMATION: 2'-O-methyl

<400> SEQUENCE: 23
uacugaguuu aaaa                                                          14

<210> SEQ ID NO 24
<211> LENGTH: 8
<212> TYPE: RNA
<213> ORGANISM: Artificial Sequence
<220> FEATURE:
<223> OTHER INFORMATION: Description of Artificial Sequence:  Reporter
      probe/siNA antisense region
<220> FEATURE:
<221> NAME/KEY: misc_feature
<222> LOCATION: (1)..(8)
<223> OTHER INFORMATION: 2'-O-methyl
<220> FEATURE:
<221> NAME/KEY: misc_feature
<222> LOCATION: (8)..(8)
<223> OTHER INFORMATION: 3' attached terminal Fluorescein

<400> SEQUENCE: 24 ggcaccca                                                                  8
```